United States Patent [19]

Moedritzer et al.

[11] Patent Number: 5,185,025
[45] Date of Patent: Feb. 9, 1993

[54] SUBSTITUTED PYRAZOLES AND THEIR USE AS HERBICIDES

[75] Inventors: Kurt Moedritzer, Webster Groves; Michael D. Rogers, Maryland Heights, both of Mo.

[73] Assignee: Monsanto Company, St. Louis, Mo.

[21] Appl. No.: 418,791

[22] Filed: Oct. 13, 1989

Related U.S. Application Data

[63] Continuation-in-part of Ser. No. 273,534, Nov. 21, 1988, abandoned.

[51] Int. Cl.⁵ .................... C07D 231/20; A01N 43/56
[52] U.S. Cl. .................... 504/282; 548/367.1; 548/366.4; 548/370.4; 548/370.1; 548/366.1; 548/364.1; 548/364.7; 548/365.1; 548/365.7; 548/312.4; 548/306.1; 504/223; 504/244; 504/248; 504/249; 504/275; 504/276; 504/197; 504/193; 504/180; 504/196; 504/181; 504/219; 504/270; 504/221; 504/225; 504/235; 504/239; 504/281
[58] Field of Search .................... 71/92; 548/375, 376, 548/377

[56] References Cited

U.S. PATENT DOCUMENTS 4,298,749  11/1981  Plath et al. .................... 548/377

*Primary Examiner*—John M. Ford
*Attorney, Agent, or Firm*—Jon H. Beusen; Howard C. Stanley

[57] ABSTRACT

The present invention relates to certain novel substituted 3-phenoxypyrazoles and their use as herbicides.

3 Claims, No Drawings

SUBSTITUTED PYRAZOLES AND THEIR USE AS HERBICIDES

RELATED APPLICATION

This application is a continuation-in-part of application Ser. No. 07/273,534, filed Nov. 21, 1988, now abandoned.

FIELD OF THE INVENTION

The present invention relates to certain novel substituted 3-phenoxypyrazoles and their use as herbicides.

BACKGROUND OF THE INVENTION

Uncontrolled weed growth continues to be a problem in our environment. In growing crops, uncontrolled weed growth normally results in lower crop yield and reduced crop quality inasmuch as weeds compete with crops for light, water and soil nutrients. Herbicides have been developed to control weed growth. However, many herbicides injure adjacent useful plants at herbicide application rates necessary to control weed growth. Further, many non-selective herbicides have environmental problems.

Plath et al U.S. Pat. 4,298,749 discloses certain substituted pyrazole ether derivatives including pyrazole phenyl ethers as having herbicidal activity. However, there still is a need in the art for herbicides which have the advantages of being safe on crops and efficacious at low application rates for cost savings and lower pesticide load on the environment.

SUMMARY OF THE INVENTION

The present invention relates to a novel class of substituted 3-phenoxypyrazoles, herbicidal compositions thereof, and their use as herbicides. Applicants have discovered that certain 3-phenoxy-pyrazole herbicides having a unique substitution pattern have herbicidal activity and that many of them have exceptionally high herbicidal activity. The unique substitution pattern includes importantly specific substituents in the 4-position of the pyrazole ring. The unique substitution pattern also provides for specific substituents in the 1- and 5-positions of the pyrazole ring. The phenyl ring has a para halo substituent or a para cyano substituent (cyano as a pseudo halogen). The phenyl ring also has in one meta position a substituent which is (i) a hydrido radical or, preferably (ii) a substituent other than hydrido having a molecular weight up to about 300. It has been found that it is the unique combination of the para substituent on the phenyl ring and substituents in the 1-, 4- and 5-positions of the pyrazole ring which provide the class of compounds with herbicidal activity and that the nature of the meta substituent (if any) on the phenyl ring is not critical for the presence of herbicidal activity.

The class of unique compounds is defined as 3-phenoxypyrazoles and agronomically acceptable salts thereof wherein (a) the pyrazole ring has a methyl, ethyl, halomethyl or haloethyl substituent in the 1-position; a halo or methyl substituent in the 4-position and a chloro, cyano, halomethyl, haloethyl, methylthio, ethylthio, methylsulfinyl, ethylsulfinyl, methylsulfonyl ethylsulfonyl or methoxymethyl substituent in the 5-position and (b) the phenyl ring has a para halo or para cyano substituent and a meta substituent having a molecular weight of up to about 300 and consisting of one or more atoms selected from the group consisting of H, C, Cl, F, Br, I, N, S, O, Si and P. The meta substituent is preferably an organic radical having up to about 10 and preferably up to about 8 carbon atoms; preferably having a molecular weight of up to about 300, preferably up to about 250, more preferably up to about 200 and having one or more atoms selected from the group consisting of H, C, Cl, F, Br, I, N, S, O, Si and P. More preferably the organic radical has one or more atoms selected from the group consisting of H, C, Cl, F, Br, N, S and O. Preferably the pyrazole ring has a halo substituent in the 4-position, preferably Cl or Br. Preferably the pyrazole ring has a halomethyl, haloethyl, methylsulfinyl, ethylsulfinyl, methylsulfonyl, or ethylsulfonyl substituent in the 5-position, more preferably a halomethyl or methylsulfonyl substituent in the 5-position.

The meta organic radical normally will comprise a saturated or unsaturated carbon chain having up to about 10 (preferably up to about 8) carbon atoms which may be linear, branched or cyclic and optionally substituted by a variety of substituents such as halo, nitro, cyano, hydroxy, and the like. The radical has a molecular weight of up to about 300 and preferably up to about 250 (most preferably up to about 200). The carbon chain may be bonded directly to the phenyl ring or through one or more difunctional substituents selected from (i) substituents comprising (or consisting of) one or more heteroatoms selected from the group consisting of N, S, O and P (preferably O and N) and (ii) substituents comprising one or more atoms selected from C and S which are bonded to one or more of said heteroatoms (preferably carbonyl). The carbon chain is optionally interrupted or terminated with one or more substituents selected from (i) substituents comprising one or more heteroatoms selected from the group consisting of N, S, O and P (preferably O, N and S) and (ii) substituents comprising one or more atoms selected from C and S which are bonded to one or more of said heteroatoms (preferably carbonyl or sulfonyl). The heteroatom may optionally be substituted with substituents such as alkyl, alkoxy or the like. The carbon chain may also be optionally substituted with (i) aryl, preferably phenyl or phenylalkyl optionally substituted with substituents such as halo, nitro, cyano, alkoxy, haloalkyl, amino, hydroxy or the like or (ii) a 3 to 7 membered, saturated or unsaturated heterocyclic radical having 1 to 3 heteroatoms selected from the group consisting of N, O and S.

The utility of the compounds of this invention as an active ingredient in herbicidal compositions formulated therewith and the method of use thereof will be described below.

DETAILED DESCRIPTION OF THE INVENTION

A preferred embodiment of the unique class of the 3-phenoxypyrazoles of the present invention are compounds represented by the Formula I and agronomically acceptable salts thereof:

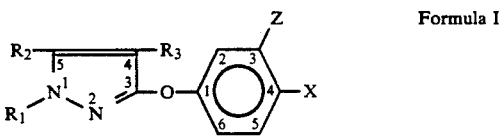

Formula I wherein:
R₁ is methyl, ethyl, halomethyl or haloethyl;

$R_2$ is chloro, cyano, halomethyl, haloethyl, methylthio, ethylthio, methylsulfinyl, ethylsulfinyl, methylsulfonyl, ethylsulfonyl or methoxymethyl;

$R_3$ is halo or methyl;

X is halo or cyano; and

Z is $R_a$;

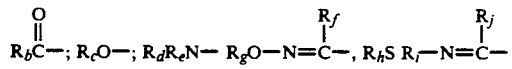

or $R_k$— wherein:

$R_a$ is selected from hydrido, hydroxy, halo, cyano; alkyl, alkenyl, alkynyl, unsubstituted or substituted with one or more hydroxy, halo, cyano, alkoxy, amino, alkylamino, alkylthio, phenyl, hydroxycarbonyl, alkylcarbonyl, alkoxycarbonyl, aminocarbonyl, alkylaminocarbonyl, alkylcarbonyloxy, di(alkoxy)carbonyl, di(alkoxycarbonyl), alkoxyalkylaminocarbonyl, alkylsulfinyl, alkylsulfonyl, alkoxycarbonylalkylsulfonyl, phosphonyl and alkylphosphinyl;

$R_b$ is selected from hydroxy, hydrido, halo, alkyl, alkoxy, alkenyloxy, alkynyloxy, phenoxy, benzyloxy, hydrazino, alkylhydrazino, oximino, phenylamino, phenylthio, alkylthio, amino, alkylamino, alkenylamino, alkynylamino, di-, tri- or tetra(alkoxy), di(alkylamino), alkylaminoalkoxy, alkoxyalkylamino, hydroxycarbonyl, alkylaminooxy, alkoxyamino, alkylthioalkoxy, alkylthioalkyl, alkoxyalkyl, alkylsufonylalkoxy, alkylsufinylalkyloxy, alkylsulfonylamino, alkylsulfonylalkylamino, hydroxycarbonylalkylamino, alkoxycarbonylalkyl, alkylcarbonylalkoxy, alkoxycarbonylalkenyloxy, alkoxycarbonylalkoxy, alkoxycarbonylalkylthio, alkylcarbonylamino, aminocarbonylalkylamino, di(alkoxycarbonyl)alkoxy, alkylaminocarbonylalkoxy, hydroxycarbonylalkylamino, alkoxycarbonylalkylamino, alkylcarbonyloxyalkoxy; alkylcarbonyloxydi(alkoxy); alkylcarbonyloxyalkylamino, alkoxycarbonyloxyalkoxy; alkoxyalylcarbonyloxyalkoxy; alkoxycarbonylaminoalkoxy, alkoxycarbonylalkoxyamino, alkoxycarbonylalkylcarbonyloxyalkoxy, alkenylaminothiocarbonylamino, alkoxycarbonyloximino, alkoxyoximino, alkylcarbonyloximino, and alkylphosphonylalkoxy;

$R_c$ is hydrido, alkyl, benzyl, alkenyl, alkynyl, alkoxycarbonyl, alkylcarbonyl, alkylsulfonyl, alkylimino, alkoxyimino, alkoxycarbonylimino, $R_x$-alkyl or $R_x$-alkenyl wherein $R_x$ is halo, hydroxy, cyano, mono, di-, tri- or tetra(alkoxy), alkynyloxy, alkylamino, alkylthio, alkylsulfinyl, alkylsulfonyl, alkylphosphonyl, alkylphosphinyl, halocarbonyl, alkylcarbonyl, hydroxycarbonyl, alkoxycarbonyl, alkenyloxycarbonyl, benzyloxycarbonyl, phenoxycarbonyl, phenylaminocarbonyl, alkylhydrazinocarbonyl, aminocarbonyl, alkenylaminocarbonyl, alkylaminocarbonyl, benzylaminocarbonyl, thiocarbonyl, phenylthiocarbonyl, alkylthiocarbonyl, alkoxyalkylthiocarbonyl, di(alkoxycarbonyl), alkylcarbonylalkoxycarbonyl, alkylsulfinylalkoxycarbonyl, alkoxycarbonylalkylcarbonyl, alkoxycarbonylalkylaminocarbonyl, hydroxycarbonylalkylaminocarbonyl, di, tri, tetra(alkoxy) carbonyl, alkoxyalkenyloxycarbonyl, alkylthioalkoxycarbonyl, alkylaminoalkoxycarbonyl, di(alkylamino)carbonyl, alkoxyalkylaminocarbonyl, alkoxyaminocarbonyl, alkylsulfonylaminocarbonyl, phenylsulfonylaminocarbonyl, alkoxycarbonylcarbonyloxy, alkoxycarbonylalkylcarbonyloxy, alkoxycarbonylamino, alkoxycarbonylalkylthio, alkoxycarbonylalkylaminocarbonyl, alkylcarbonylaminocarbonyl, alkylcarbonyloxydi(alkoxy)carbonyl, alkoxyalkylcarbonyloxydi(alkoxy)carbonyl, alkoxycarbonylcarbonyloxydi(alkoxy)carbonyl, alkoxycarbonylalkylcarbonyloxybis(alkoxy)carbonyl, alkoxy-carbonylaminoalkoxycarbonyl, alkylsulfonylalkoxycarbonyl, alkylsulfonylaminocarbonyl, alkylphosphonylalkoxycarbonyl, alkoxycarbonyloximinocarbonyl, alkoxyoximinocarbonyl, or alkyloximinocarbonyl;

$R_d$, and $R_e$ are independently selected from hydrido, alkyl, alkenyl, alkynyl, benzyl, phenyl, alkoxy, alkenyloxy, benzyloxy, hydridocarbonyl, alkylcarbonyl, phenylcarbonyl, alkylsulfonyl, aminocarbonyl, alkoxycarbonyl, alkoxyalkyl, alkylthioalkyl, alkylaminoalkyl, alkylsulfonylalkyl, halocarbonylalkyl, hydroxycarbonylalkyl, alkoxycarbonylalkyl, di-, tri-(alkoxy), phenylthioalkyl, di(alkylamino)alkyl, alkylphosphonyl alkyl or alkysilylalkyl; or $R_d$ is hydrido or alkyl and $R_e$ is amino, alkylamino, phenylamino or alkoxycarbonylalkylamino; or $R_d$ and $R_e$ together are a cycloalkyl chain having 2 to 6 carbon atoms;

$R_g$ is selected from hydrido, alkyl, hydroxycarbonylalkyl, alkoxycarbonylalkyl, alkylaminocarbonylalkyl, alkylthiocarbonylalkyl, di(alkoxy)carbonylalkyl, and di(alkoxycarbonyl)alkyl;

$R_f$ is selected from hydrido, alkyl, and alkoxyalkyl;

$R_h$ is hydrido, halo, alkyl, alkenyl, alkoxy, alkylamino, phenoxy, alkylaminocarbonyl, alkoxycarbonyl, hydroxycarbonylalkyl, alkoxycarbonylalkyl, alkylthio, alkoxycarbonylalkylthio and alkylsilylalkoxycarbonylalkyl or alkylsulfinylamino;

$R_i$ and $R_j$ are independently selected from hydrido, alkyl, alkoxy and alkylamino;

$R_k$ is alkylphosphonyl, alkylaminoimino, alkylsulfinyl, alkylsulfonyl, alkylaminosulfonyl or halosulfonyl.

$R_a$ through $R_j$ can also comprise a heterocyclic substituent selected from triazolyl, morpholinyl, piperidyl, indolyl, piperazinyl, pyrrolidinyl, pyrazolyl, pyrrolinyl, azetidinyl, thienyl, imidazolyl, pyrimidinyl, furyl, pyridyl, tetrahydro-2H-pyranyl, pyridinyl, pyrrolidinonyl, indazolyl, furanyl, dioxolanyl, 5,6-dihydro-1,4,2-dioxazinyl, tetrahydrofuranyl, tetrahydro-2-oxofuranyl, 4,5-dihydro-4-oxofuranyl, benzimidazolyl, 4,5-dihydrooxazolyl, benzoxazolyl, piperidinyl, aziridinyl, 1H-2,5-dihydropyrrolyl, 1H-isoindole-1,3(2H)-dionyl, furanonyl, thiomorpholinyl, azepinyl or oxocyloalkyl, oxocycloalkenyl.

Preferred compounds of the present invention include compounds wherein $R_1$ is methyl; compounds wherein $R_2$ is halomethyl, methylsulfinyl or methylsulfonyl and most preferably where $R_2$ is halomethyl, especially difluoromethyl or trifluoromethyl; compounds wherein $R_3$ is halo especially chloro and bromo and compounds wherein X is halo especially chloro.

Preferred compounds of the present invention have a Z which is

and most preferably $R_cO$ wherein $R_b$, $R_c$, $R_d$, $R_e$, $R_f$ and $R_g$ are as defined hereinabove. Z is preferably selected from alkoxy, haloalkoxy, bis(alkoxy), alkoxycarbonyl, alkoxycarbonylalkoxy, aminocarbonylalkoxy, alkylaminocarbonylalkoxy, alkylsulfonylaminocarbonylalkoxy, alkylamino, hydroxyalkylamino, alkoxyamino, alkoxyalkylamino, hydroxycarbonylalkylamino, and alkoxycarbonylalkyloxyimino.

The nature of the Z substituent is not critical to the presence of herbicidal activity for the unique class of compounds of the present invention provided dimers and polymers of the compounds are not optimum. Compounds with other types of Z substituents are as follows:

(a) compounds according the Formula I with a Z substituent as defined above wherein substituents for $R_a$ through $R_k$ are selected from the collective group of substituents recited above for $R_a$ through $R_k$; and (b) compounds according to Formula I with a Z substituent as defined above wherein $R_a$ through $R_k$ are substituents which comprise one or more radicals selected from carbonyl, oxy, amino, thio, carbonyloxy, carbonylamino, imino, oximino, sulfonyl, sulfinyl, thiocarbonyl, phosphinyl, phosphonyl, hydrazino, and the like.

The phenyl ring can be optionally substituted in the other ring positions by one or more substituents known to those skilled in the art such as ortho halo (6' fluoro) which do not unacceptably diminish the herbicidal activity. Compounds having such substituents are contemplated as equivalents of the compounds claimed herein.

The pyrazole ring can also be substituted in the 1-, 4- and 5-position by other substituents such as 4-nitro and 5-halo which do not unacceptably interfere with the herbicidal activity of the molecule. These compounds should also be contemplated as equivalents of those claimed herein.

The terms "di-, tri- and tetra-" mean that the referenced groups are polymeric such as di(methoxy) means $CH_3-O-CH_2-O-$.

The term "alkyl" means herein a straight, branched and cyclic radical having 1 to 12 carbon atoms, preferably 1 to 5 carbon atoms and includes, but is not limited to, ethyl, methyl, 2-propyl, 1-ethylpropyl, 1-methylpropyl, n-butyl, 1,1-dimethylethyl, 2,2-dimethylpropyl, pentyl, 2-methylpropyl, 1-methylethyl and dodecyl. The cyclic alkyl radicals include cycloalkylalkyl radicals and alkylcycloalkyl radicals wherein the cyclic group of the radical has from 3 to 6 carbon atoms. Examples of cycloalkyl radicals are cyclopropyl, cyclopropylmethyl, methylcyclopropyl, cyclobutyl and cyclohexyl.

The terms "alkenyl" and "alkynyl" herein mean a straight, branched or cyclic group having 2 to 6 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methyl-ethenyl, and the like. Examples of such alkynyl groups include ethynyl, 1-propynyl, 2-propynyl, and so forth. The term "halo" is intended to mean fluoro, chloro, bromo or iodo.

The term "haloalkyl" is intended to mean an alkyl radical substituted with one or more halogen atoms preferably selected from bromo, chloro or fluoro. The term "alkoxycarbonyl" is intended to mean

wherein $R_1$ is alkyl which may be substituted by a variety of substituents such as halo, hydroxy, nitro, cyano or the like. The term "alkylamino" is intended to mean $R_1R_mN-$ wherein $R_m$ is hydrido or lower alkyl wherein alkyl may also be substituted with a variety of substituents. The term "alkoxycarbonylalkyl" is intended to mean

The term "alkylthio" is intended to mean $R_1S-$ and the term "alkylthiocarbonyl" is intended to mean

The term "oximino" is intended to mean

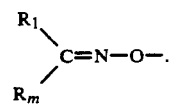

The term "alkylphosphonyl" and "alkylphosphinyl" are intended to mean, respectively

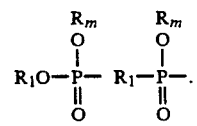

The term "alkylsulfonyl" is intended to mean

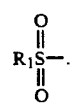

The term "alkylsulfinyl" means

The term "imino" is intended to mean $-C=N-$.

Agriculturally acceptable salts of the present invention include alkali, alkaline earth, acid addition, base addition and alkylation salts. Generally, the salts will have suitable cations which include alkali metals such as sodium, potassium, and lithium; alkaline earth metals such as calcium, organic ammoniums and ammonium salts, sulfonium, phosphonium salts, and other salt complexes. Alkylation salts are generally formed by alkylation of nitrogen or sulfur atoms in the molecule.

The 5-phenoxypyrazole regioisomers of the compounds of the present invention may exhibit herbicidal activity. However, the 3-phenoxypyrazoles of the present invention are substantially more herbicidally active than their corresponding 5-phenoxypyrazole regioisomers. A 3-phenoxypyrazole regioisomer is structurally identical to its corresponding 5-phenoxypyrazole regioisomer except for the location of the substituent on the pyrazole nitrogen.

The alkyl, alkenyl, alkynyl, phenyl and phenylalkyl radicals in the compounds of the present invention represented by Formula I can in turn be substituted by a variety of substituents which will not interfere with the biological activity of the compound in addition to those substituents which are specifically exemplified herein.

Suitable substituents include for example substituents such as halo, cyano, nitro, amino, hydroxy, haloalkyl, alkoxy, alkylthio, alkylsilyl, sulfonyl, phosphonyl and the like and such radicals in the compounds of the present invention with these substituents are intended to be within the scope of the claims of the present invention. Such substitution will normally only be mono, di or tri substitution ("mono/polysubstitution") on such radicals provided, however, in the case of halo and hydroxy, a greater degree of substitution may be suitable. Further, many of the compounds of the present invention may have more than one possible stereoisomer and structures illustrated are intended to include all such stereoisomers.

The procedures described below depict suitable methods whereby the compounds of this invention may be prepared by known chemical procedures from compounds which are known in the art and/or are readily available commercially. These procedures described below are merely illustrative and those skilled in the art will know a variety of other procedures suitable for use in making the compounds of the present invention.

Compounds of the present invention can generally be prepared by two procedures, Procedure I or Procedure II. Certain of the compounds of the present invention, such as those having a para halo substituent on the phenyl ring, can be prepared by Procedure I from the corresponding 3-phenoxypyrazole compound having a para-nitro substituent on the phenyl ring rather than the para halo or para cyano substit-uent of the invention compounds (hereinafter referred to as "Nitro Precursors"). The Nitro Precursors are converted into the compounds of the present invention by a three step process involving sequential reduction, diazonium salt formation and Sandmeyer replacement reaction. The meta Z substituent on the phenyl ring and the substituents in the 1,4 and 5 position on the pyrazole ring are carried over from the Nitro Precursor into the invention compound.

Other compounds of the present invention, such as those having a para cyano or a para fluoro substituent on the phenyl ring, can be prepared by Procedure II by reacting a 3-hydroxypyrazole intermediate with a fluorobenzene intermediate having one of the following structures:

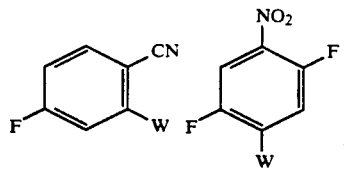

W can be selected from a variety of substituents such as the desired substituent in the invention compound or a displaceable substituent such as fluoro which can be subsequently displaced from the phenoxypyrazole with the desired substituent. The nitro group is removed by diazonium salt formation and reduction. Other methods for making compounds of the present invention will be known to those skilled in the art.

The Nitro Precursors can generally be prepared by two procedures, Procedure A or Procedure B. Certain Nitro Precursors are prepared by Procedure A in a two-step reaction as follows: (i) reacting 2,4-dichloronitrobenzene with at least two equivalents of the appropriately substituted 3-hydroxypyrazole intermediate in a suitable solvent such as DMSO or DMF with potassium carbonate under nitrogen at an elevated temperature, and (ii) reacting the product of (i) with an appropriate nucleophilic reactant in a suitable coordination solvent such as glyme generally in the presence of a base. Suitable nucleophilic reactants include hydroxides, organic oxide salts, enolates, thiolates, ammonia, and primary and secondary amines and hydrazines. Suitable nucleophilic reactants are hydroxy, alkyoxy, thio, alkylthio, amino, alkylamino, hydrazino, alkylhydrazine, alkoxyamino, and alkylamino-oxy which are unsubstituted or substituted with one or more substituents selected from alkoxy, alkylamino, alkylthio, alkoxyalkyl, alkylaminoalkyl, alkylthioalkyl, halo and nitro. Other Nitro Precursors can be prepared from these compounds using known chemical procedures.

Nitro Precursors can also be prepared by Procedure B which is similar to Procedure II.

The 3-hydroxypyrazole intermediates can be conveniently prepared by the processes discussed below. A 5-haloalkyl-3-hydroxy-1-methylpyrazole intermediate may be halogenated to form the 5-haloalkyl-4-halo-3-hydroxy-1-methylpyrazole intermediate.

The 5-trifluoromethyl-3-hydroxy-1-methyl pyrazole intermediate is conveniently prepared by reacting an alkylhydrazine with an alkyl 3-haloalkylpropynoate which is in turn prepared generally in accordance with procedures set forth in Huang et al. Scientia Sinica 25, 21 (1982). The Huang phosphorane intermediate can be prepared by reacting (carbethoxymethyl)triphenylphosphonium bromide with trifluoroacetic anhydride in the presence of triethylamine and tetrahydrofuran.

The 5-trifluoromethyl-3-hydroxy-1-methylpyrazole intermediate may also be conveniently prepared by reacting ethyl 4,4,4-trifluoro-2-butynoate with methylhydrazine in a suitable solvent such as methylene chloride or methanol/water at a low temperature from about $-78°$ C. to about $-20°$ C. The reaction at higher temperatures will result in a mixture of the 3-hydroxy and 5-hydroxypyrazole isomers. It is believed that reduced temperatures and more polar solvents provide greater amounts of the desired 3-hydroxy isomer of the pyrazole. Prior to reacting the pyrazole intermediate with the appropriate nitrobenzene to form the Nitro Precursor, it is generally preferred to purify the pyrazole to separate out the 5-hydroxypyrazole isomer. This purification can be easily accomplished by stirring the isomer mixture product in an aqueous solution of sodium bicarbonate. The 5-hydroxy isomer is dissolved into solution while the 3-hydroxy isomer remains in suspension and is readily separated.

An alternative method of forming 5-trifluoromethyl-3-hydroxy-1-methylpyrazole involves reacting ethyl 4,4,4-trifluoroacetoacetate in acetone with preferably triethylmethylammonium methylsulfate and with dimethyl sulfate in the presence of anhydrous potassium carbonate to form 3-methoxy-4,4,4-trifluoro-2-butenoic acid ethyl ester. This ester is then reacted directly with methylhydrazine to form the 3- and 5-hydroxy isomer mixture of the intermediate pyrazole. The desired isomer can be separated as described above. Alternatively, alkyl, 2,4,4 tri-fluoroacetoacetate can be reacted in a like manner to give 1-methyl-3-hydroxy-4-fluoro-5-difluoromethylpyrazole.

Another method of making the 3-hydroxy-pyrazole involves reacting the ethyl 4,4,4-trifluoroacetoacetate directly with the methylhydrazine in ether to form a mixture of intermediates, 5-hydroxypyrazolidin-3-one and 3-hydroxypyrazolidin-5-one and dehydration of these intermediates by the addition of sulfuric acid in chloroform to form a mixture of the 3- and 5-hydroxypyrazoles. The desired isomer can be separated as described above.

Referring to procedure below, a preferred process for making 3-hydroxypyrazole intermediates comprises reacting 3-(amino or substituted amino)-2-alkenoic acid or acid derivative with an alkyl substituted hydrazine. Suitable alkenoic acid derivatives included esters, thioesters and amides. In the procedure below, Y is hydrido or halo, preferably fluoro and R is hydrido, alkyl or phenyl, preferably hydrido. The alkenoic acid can also have a halo substituent in the 2-position.

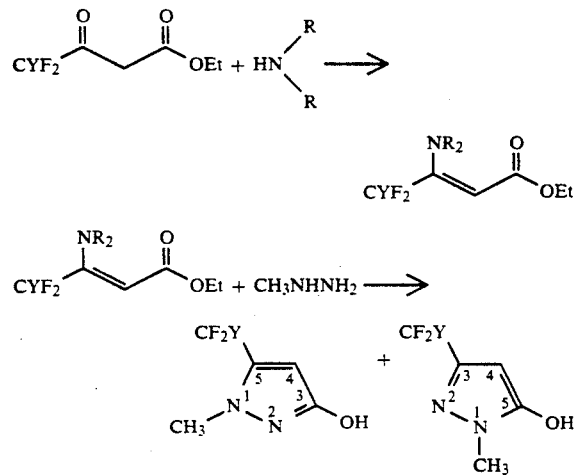

A preferred method of forming the 5-trifluoromethyl-3-hydroxy-1-methylpyrazole involves bubbling ammonia gas through ethyl 4,4,4-trifluoroacetoacetate at an elevated temperature while removing water to form 3-amino-4,4,4-trifluoro-2-butenoic acid ethyl ester. This ester is then reacted directly with methylhydrazine to form the 3- and 5-hydroxy isomer mixture of the intermediate pyrazole. The desired isomer can be separated as described above.

Pyrazole intermediates having a 5-alkylthio (e.g., methylthio) and a 4-halo (e.g., chloro) substituent can be made by reacting methylhydrazine with alkyl 3-methylthio-2,3-dichloroacrylate and potassium carbonate in a suitable solvent. The corresponding Nitro Precursor can be made by reacting the pyrazole with a 4-halonitrobenzene according to Procedure B.

The Nitro Precursor having either a 5-alkylsulfinyl or a 5-alkylsulfonyl substituent can be made by oxidation of the corresponding 5-alkylthiophenoxypyrazole with appropriate amounts of a suitable oxidizing agent such as m-chloroperbenzoic acid in a suitable solvent such as dichloromethane.

Except as described below, other pyrazole intermediates can be prepared generally in accordance with these procedures. The 1-ethylpyrazoles are also prepared generally in accordance with these procedures. The ethylhydrazine is conveniently liberated from its oxalate salt in situ with a suitable base (e.g., triethylamine or sodium methoxide) during the reaction. Phenoxypyrazoles having N-bromodifluoromethyl or N-difluoromethyl substituents are made by reacting dibromodifluoromethane or chlorodifluoromethane, respectively, with a phenoxypyrazole having N-hydrido substituent which is made from the corresponding N-tetrahydropyranylpyrazole. Phenoxypyrazoles having N-trifluoromethyl substituents are made by reacting a N-bromodifluoromethylphenoxypyrazole with AgBF$_4$.

The 5-haloalkyl-3-hydroxypyrazole intermediates can be chlorinated or brominated to form the corresponding 5-haloalkyl-4-halo-3-hydroxypyrazole intermediate. Suitable chlorinating/brominating agents include bromine, chlorine, sulfuryl chloride and sulfuryl bromide. Preferred chlorinating/brominating agents are 1,3-dichloro-5,5-dimethylhydantoin and 1,3-dibromo-5,5-dimethylhydantoin in a solvent such as diethyl ether.

The 5-haloalkylpyrazole can, in some cases, be chlorinated or brominated after the phenoxypyrazole is formed by reaction with sulfuryl halide or 1,3-dihalo-5,5-dimethylhydantoin in a suitable solvent such as acetonitrile. Phenoxypyrazoles having Z as R$_c$O may experience some side reactions.

The 5-haloalkylpyrazole intermediates having a 4-fluoro, a 4-iodo, a 4-methyl, a 5-fluoromethyl or a 5-trichloromethyl substituent are made in a different manner. The pyrazole intermediate having a 4-fluoro substituent is made by reacting ethyl trifluoroacetate with ethyl fluoroacetate neat and a strong base, such as sodium hydride, to give ethyl 2,4,4,4-tetrafluoroacetoacetate which is sequentially reacted with (i) dimethylsulfate in the presence of potassium carbonate and (ii) methylhydrazine to form the corresponding 4-fluoropyrazole. The 4-iodopyrazole is formed from the corresponding 4-bromopyrazole using lithiation chemistry. In order to protect the 3-hydroxy group the 4-bromopyrazole is reacted with trialkylsilylchloride and a base. The resulting 3-trialkylsiloxy-4-bromopyrazole is then sequentially reacted with (i) n-butyl lithium at −78° C. in THF; (ii) iodine and (iii) aqueous HF in acetonitrile to form the 4-iodopyrazole intermediate. The 4-methyl pyrazole is made in a similar manner except the iodine reactant is replaced with a methyl iodide reactant. Pyrazole intermediates with a 5-fluoromethyl substituent are made from the corresponding 5-methoxycarbonylpyrazole which is in turn prepared by reacting dimethyl acetylenedicarboxylate with methylhydrazine in ether. The 5-methoxycarbonylpyrazole is sequentially reduced with lithium aluminum hydride and fluorinated with dimethylaminosulfur trifluoride (DAST) to form the 5-fluoromethylpyrazole intermediate. The 5-trichloromethylpyrazole can be made by suitable processes known to those skilled in the art such as by chlorination. The 4,5-dichloro-3-hydroxy-1-methylpyrazole intermediate is prepared from methyl 2,3,3,-trichloroacrylate and methylhydrazine. The 5-methoxymethyl-4-chloro-1-methylpyrazole intermediate is made by reacting the 5-lithio-4-chloro-3-trialkylsiloxy-1-methylpyrazole and bromomethyl methyl ether with subsequent desilylation.

Nitro Precursors having a 5-cyano substituent on the pyrazole ring are made from phenoxypyrazoles having a 5-hydrocarbonyl substituent. The compounds having the 5-hydrocarbonyl are made via lithiation chemistry as noted above by reaction with dimethylformamide. The 5-hydrocarbonyl phenoxypyrazole is then reacted with hydroxylamine and acetic anhydride to give the corresponding 5-cyano. The 4-methyl-3-hydroxypyrazoles having a 5-methylthio substituent are made by (i) reacting 4-bromo-3-trialkylsiloxypyrazole sequentially with lithium tetramethylpiperidine and dimethylsulfide and (ii) alkylation of the product of (i) with methyliodide.

Those skilled in the art will appreciate that the 3-hydroxypyrazoles may exist in either of their tautomeric structures (the 3-hydroxypyrazole or the pyrazolidin-3-one) and the 3-hydroxypyrazole structure used herein is intended to mean both tautomeric structures.

Nitrobenzene Intermediates

The intermediate 2-(alkoxy or alkoxycarbonylalkoxy)-4-fluoronitrobenzenes are prepared from 2-hydroxy-4-fluoronitrobenzenes which are either commercially available or are prepared by reacting 2,4-difluoronitrobenzene with sodium hydroxide in DMSO and extracting the product from water with hexane. To form intermediate nitrobenzenes having an alkoxy or a haloalkoxy W substituent, the 2-hydroxy-4-fluoronitrobenzene is reacted with an appropriate alkylating agent (e.g., alkyl iodide, chlorodifluoromethane or alkylsulfonate) in a suitable solvent (e.g., acetone, acetonitrile, dimethylformamide (DMF) or dimethylsulfoxide (DMSO) in the presence of a base (e.g., potassium carbonate or sodium hydroxide) for an extended period (e.g., 2 to 3 days). The reaction can be run at room temperature or at higher temperatures. An alternative procedure for making a nitrobenzene intermediate having an alkoxy or alkylthio W substituent is to react 2,4-difluoronitrobenzene with sodium alkoxide or sodium alkylthiolate in a suitable solvent. The intermediate nitrobenzene is then isolated by standard laboratory techniques.

The intermediate nitrobenzenes with the alkoxycarbonylalkoxy W substituent are formed from 2-hydroxy-4-fluoronitrobenzene. 2-Hydroxy-4-fluoronitrobenzene is reacted with a haloalkylcarboxylate (e.g., ethyl 2-bromopropionate) in a suitable solvent (e.g., acetone, acetonitrile, DMF, or DMSO) in the presence of a base (e.g., potassium carbonate) for an extended period (e.g., 3 days). The intermediate nitrobenzene is then isolated by standard laboratory techniques.

A procedure for making a nitrobenzene intermediate having an alkoxycarbonyl W substituent is to esterify the corresponding commercially available 5-chloro-2-nitrobenzoic acid.

The intermediate 4-fluoro-2-alkylaminonitrobenzenes are prepared by reacting the 2,4-difluoronitrobenzene with the appropriate amine in a suitable solvent such as methanol with triethylamine. The desired isomer is separated by standard laboratory procedures. 4-Fluoronitrobenzene intermediates with an alkoxyamino substituent are made by reaction with the appropriate hydrogen chloride alkoxyamine salt in base. The 4-fluoro-2-hydrazinonitrobenzenes are made in a similar fashion.

INVENTION COMPOUNDS - GENERAL PROCEDURE

The compounds of the present invention are conveniently prepared by Procedure I or II. Procedure I generally involves preparing invention compounds (such as those having a para-halo substituent) from their corresponding Nitro Precursors by sequential reduction, diazonium salt formation and Sandmeyer replacement reaction. Invention compounds having a meta substituent which interferes or interacts with reduction, diazonium salt formation or Sandmeyer replacement reaction are made by protecting and deprotecting the meta substituent by known chemical procedures such as acetylation for amine substituents.

Compounds of the present invention are formed from the Nitro Precursors in three steps. In the first step, the para-nitro substituent of the Nitro Precursors is reduced by standard hydrogenation techniques using a suitable catalyst such as palladium on carbon. The second step involves diazonium salt formation. Conveniently the product of step 1 is mixed with sodium nitrite and a mineral acid in a suitable solvent such as water or acetonitrile. The third step involves Sandmeyer replacement of the diazonium with a halo or cyano substituent. The diazonium salt from step 2 is reacted with a suitable Sandmeyer replacement reactant (CuCN, CuCl or KI) in a suitable neutral solution to form the compounds of the present invention.

In an alternative procedure, the diazonium salt formation and Sandmeyer replacement can be performed together in situ. The reduced Precursor from step 1 can be mixed with t-butyl nitrite and a Sandmeyer replacement reactant (e.g., CuBr$_2$) in a suitable solvent such as acetonitrite.

The reaction for Procedure II for making invention compounds is generally similar to Procedure B for making Nitro Precursors.

Procedure II involves reacting an appropriate pyrazole intermediate with an appropriate halobenzonitrile intermediate to give the desired product generally as follows:

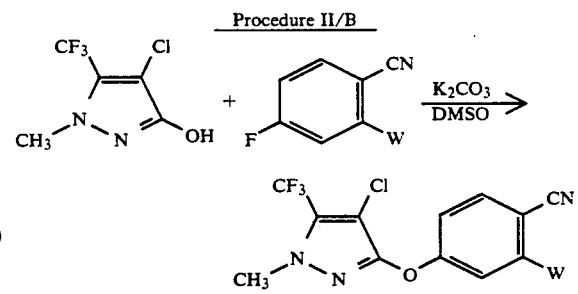

Procedure II/B

The pyrazole and halobenzonitrile are mixed together in the presence of a base such as potassium carbonate or potassium hydroxide in a suitable solvent such as DMSO, DMF or sulfolane at an elevated temperature. The product is then isolated by standard laboratory procedures. However, for Procedure II, the product is conveniently isolated by (i) crystallization from isopropanol and (ii) extraction of the oil filtrate with hexane.

A. Nitro Precursors having R$_c$O as a Z Substituent

Nitro Precursors having an R$_c$O such as an alkoxy Z substituent in the meta position of the phenyl ring can be formed by reacting an alkali alkoxide such as sodium methoxide with the corresponding 2,4-bis(pyrazolyloxy)nitrobenzene in accordance with Procedure A. Nitro Precursors having an R$_c$O such as alkoxy or alkoxycarbonylalkoxy as a Z substituent on the phenyl ring can be prepared by reacting the appropriate pyrazole intermediate with a halonitrobenzene intermediate having either an alkoxy or alkoxycarbonylalkoxy W substituent generally in accordance with Procedure B. Lastly, Nitro Precursors having an R$_c$O as Z generally can be prepared by reacting the appropriate R$_c$OH with the corresponding phenoxypyrazole having a Z fluoro substituent or $R_cX$ (where X is (i) halo selected from Cl, I or Br or (ii) X is $CH_3SO_2O$—) with the corresponding phenoxypyrazole having a Z hydroxy substituent.

Nitro Precursors having a hydroxy Z substituent are made by (a) reacting 2-methoxy-4-fluoronitrobenzene in accordance with Procedure B followed with demethylation with boron tribromide or (b) sequentially reacting the appropriate pyrazole with 2-(methylcarbonyloxy)-4-chloronitrobenzene in accordance with Procedure B and then hydrolysis by standard laboratory procedures. Nitro Precursors having alkoxycarbonylalkoxy as Z can also be made by reacting a haloacetate with a phenoxypyrazole having Z as a hydroxy. Nitro Precursors having Z as alkylaminoalkoxy can be made by reacting a phenoxypyrazole having Z as fluoro with a tertiary amine having a hydroxyalkyl substituent. Compounds having Z as alkylthioalkoxy, alkylsulfonylalkoxy and alkylphosphinylalkoxy are made in a like manner. A great variety of Nitro Precursors can be made by standard esterification of the corresponding acid chloride where Z is —O—CH(R)(CH$_2$)$_n$-COCl. Nitro Precursors of the present invention having an alkylcarbonylalkoxy as a Z substituent are formed by reacting an appropriate pyrazole intermediate with a nitrobenzene which has a corresponding ketal radical as a W substituent to protect the alkylcarbonylalkoxy group during the reaction. After forming the phenoxypyrazole product, acid is added to the reaction mixture to hydrolyze the ketal to give the corresponding alkylcarbonylalkoxy radical as a Z substituent. Nitro Precursors having Z as alkenyloxy can be made by dehydrobromination of the corresponding haloalkoxy compound which can be prepared by Procedure A. Nitro Precursors having Z as an alkylimino are made by reacting a phenoxy pyrazoles having a meta fluoro with ketoxime. Nitro Precursors having a phosphinyl Z substituent are made by the sequential reactions of (i) reacting a phosphonite with an aldehyde, (ii) reacting the product of (i) with trifluoromethanesulfonic anhydride (iii) reacting the product of (ii) with 2-hydroxy-4-fluoronitrobenzene and (iv) reacting the product of (iii) according to Procedure B.

B. Nitro Precursors having

as a Z Substituent

Nitro Precursors an alkoxycarbonyl as a Z substituent on the phenyl ring are made by reacting the appropriate pyrazole with a 4-halonitrobenzene having an alkoxycarbonyl W substituent generally in accordance with Procedure B.

Nitro Precursors of the present invention having the alkoxycarbonyl as a Z substituent are then converted into other types of Nitro Precursors which have derivative substituents of the alkoxycarbonyl substituent by transesterification or by hydrolysis of the alkoxycarbonyl substituent to form the corresponding carboxylic acid which can be (i) converted to other esters by esterification by standard laboratory procedures by forming the acid chloride and reacting it with the appropriate alcohol provided that hindered alcohols may require reaction with the sodium salt of the alcohol (e.g., alkenyloxycarbonyl substituents) or (ii) converted into aminocarbonyl compounds by sequential formation of the acid chloride and amination by standard laboratory procedures (e.g., alkylaminocarbonyl Z substituents); or (iii) converted into the thioesters by esterification of the acid chloride by standard laboratory procedures (e.g., alkylthiocarbonyl Z substituents); or (iv) converted into sulfonylaminocarbonyl compounds by sequential formation of the acid chloride and amination with a sulfonamide, neat, by standard laboratory procedures (e.g., alkylsulfonylaminocarbonyl as Z substituent) which can be N-alkylated by reaction with methyliodide and potassium carbonate in acetone; or (v) converted into oximinocarbonyl compounds by sequential formation of the acid chloride and reaction with a ketoxime (e.g., oximinocarbonyl as the E substituent).

Nitro Precursors wherein $R_b$ is alkyl are made by reacting a 4-fluoronitrobenzene intermediate having a 2-alkylcarbonyl substituent in accordance with Procedure B. Nitro Precursors where $R_b$ is an alkoxyalkyl are made in the same manner wherein the nitrobenzene intermediate is made by reacting alkoxyalkylnitrile with 3-fluorophenyl magnesium bromide with subsequent nitration. Nitro Precursors wherein $R_b$ is an oximino are prepared by reacting the corresponding acid chloride with N-hydroxyethyl acetimidate. Compounds wherein $R_b$ is hydroxycarbonyl can be made by oxidizing the corresponding phenoxypyrazole having a Z methylcarbonyl substituent with selenium dioxide. Nitro Precursors wherein $R_b$ is poly(alkoxy) are made by reacting the corresponding phenoxypyrazole with a bromoether or bromopolyether compound.

C. Nitro Precursors with $R_a$ as Z Substituent

Nitro Precursors having a $R_a$ alkyl substituent can be made by reducing a phenoxy pyrazole with Z as chlorocarbonyl with sodium borohydride to the corresponding benzyl alcohol which, in turn, can be reacted with appropriate reactants to form other Nitro Precursors having various types of substituted methyl radicals as Z. For example, the benzyl alcohol can be oxidized to the benzaldehyde. The Z iodomethyl compound is formed by sequentially reacting the benzyl alcohol with (i) methanesulfonyl chloride and (ii) sodium iodide. The compounds where E is alkylaminoalkyl are made by reacting Z as iodomethyl with the appropriate amine. The Z-bromomethyl and chloromethyl compound can be made by reacting the corresponding alcohol with either phosphorus tribromide or thionyl chloride, respectively, in a suitable solvent. Nitro Precursors having a —CX$_2$H as a Z substituent are conveniently made by halogenating the benzaldehyde with a suitable agent such as diethylaminosulfur trifluoride (DAST) or thionyl chloride. The procedure for making other substituted methyl radicals as Z will be known to those skilled in the art.

Nitro Precursors having a methyl or trifluoromethyl substituent as a Z substituent on the phenyl ring are made by reacting the appropriate pyrazole intermediate with either 2-methyl-4-halonitrobenzene or 2-trifluoromethyl-4-halonitrobenzene, respectively, in accordance with the Procedure B.

Other Nitro Precursors having an $R_a$ substituent can be made by sequentially reacting the corresponding benzyl alcohol with methanesulfonyl chloride and then with appropriate nucleophiles such as alkoxides, amines or mercaptans in a base. Nitro Precursors having alkylcarbonyloxymethyl as a Z substituent can be made by reacting the corresponding benzyl alcohol with the appropriate acid chloride. Nitro Precursors having an alkoxycarbonylmethyl Z substituent are prepared by reacting the appropriate pyrazole with 2-alkoxycarbonylmethyl-4-fluoronitrobenzene generally in accordance with Procedure B. The corresponding acid, ester and amide derivatives can then be made by standard laboratory procedures. Nitro Precursors having Z as alkoxycarbonylethyl can be made by reacting the compound with Z amino sequentially with (i) t-butyl nitrite and (ii) with methyl acrylate and $CuCl_2$. Nitro Precursors having alkenyl substituents can be made from the corresponding Z aldehyde compound generally in accordance with the Wittig reaction. Nitro Precursors having an alkynyl Z substituent can be made by reacting the corresponding Z hydroxy compound with trimethylsilylacetylene and bis(triphenylphosphine)palladium chloride. Nitro Precursors having Z cyanoalkyl or cyanoalkenyl substituents are made by reacting the corresponding aldehyde with cyanoacetic acid. Nitro Precursors having a Z cyano substituent are made from the corresponding 2-nitro-5-halo benzonitrile according to Procedure B. Compounds having a Z methylthiomethyl substituent can be made by reacting the methanesulfonate of the benzyl alcohol with sodium methyl mercaptan.

D. Nitro Precursors Having an $R_dR_eN$ as a Z Substituent

Nitro Precursors having an amino or hydrazino Z substituent are prepared by reacting the appropriate amino or hydrazino nucleophilic reactant with (a) 2,4 bis(pyrazolyloxy)nitrobenzene generally in accordance with Procedure A or (b) with 2,4-difluoronitrobenzene to prepare the corresponding 2-amino or 2-hydrazino-4-fluoronitrobenzene or with the corresponding phenoxypyrazole having a Z fluoro substituent generally in accordance with the above displacement procedures. Nitro Precursors having an aminocarbonylamino Z substituent can be made by reacting a phenoxypyrazole having Z amino with chlorosulfonylisocyanate. Nitro Precursors having an alkylphosphonylalkylamino Z substituent can be made by reacting the corresponding phenoxypyrazole with Z fluoro with diethyl 2-aminoalkylphosphonate.

E. Nitro Precursors Having an

Substituent

Nitro Precursors having an

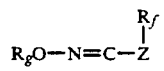

Z substituent can be prepared by two methods. The first method involves reacting a phenoxypyrazole having a methylcarbonyl Z substituent with 2-aminoxyacetic acid. The resulting carboxylic acid can be esterified by refluxing in a suitable alcohol in the presence of an acid catalyst such as toluenesulfonic acid. The acid may also be converted to amides and thioesters through the acid chloride.

These nitro precursors can also be prepared by reacting the phenoxypyrazole having a loweralkylcarbonyl Z substituent with hydroxylamine hydrochloride and alkylation of the resulting oxime. Suitable methods for alkylation include treating the intermediate oxime with an alkyl halide (e.g., methyl iodide or methyl bromoacetate) and potassium carbonate in acetonitrile. The oxime can also be alkylated under standard phase transfer conditions.

F. Nitro Precursors having $R_hS$ as a Z Substituent

Nitro Precursors having $R_hS$ as a Z substituent are made generally following the same procedures used for making compounds having amino Z substituents. Nitro Precursors having $R_h$ as alkyl are made by reacting the Z fluorophenoxypyrazole with a mercaptan and the resulting 2 alkylthio-4-fluoronitrobenzene according to Procedure B. Nitro Precursors having Z as alkylaminothio, alkoxythio or the like are made by sequentially reacting the corresponding phenoxypyrazole having a Z-fluoro substituent with (i) $Na_2S_2$ to form the disulfide (which can be reduced to Z as HS—), (ii) $Cl_2$ in $CH_2Cl_2$ (to form Z as SCl) and (iii) appropriate thiolate nucleophile such as mercaptans or the like with a base. Nitro Precursors having Z as alkylaminosulfonyl are formed in a similar manner except they are chlorinated in aqueous acetic acid. Nitro Precursors having Z as alkylaminocarbonylthio are made by reacting the phenoxypyrazole having a Z as HS-substituent with an isocyanate.

G. Nitro Precursors having an

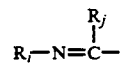

as a Z Substituent

Nitro Precursors having an imino Z substituent are prepared by reacting the phenoxypyrazole having a Z aldehyde group with an appropriate amine.

H. Nitro Precursors having an $R_k$ as a Z Substituent

Nitro Precursors having an $R_k$ as a Z substituent can be made by a variety of methods known to those skilled in the art. Suitable methods are as follows. Thiocarbonyl compounds such as amino(thiocarbonyl) as Z can be made by reacting the corresponding carbonyl compound with phosphorus pentasulfide. Nitro Precursors having Z as an alkylsulfinyl and alkylsulfonyl can be made by oxidizing the corresponding alkylthio compound with m-chloroperbenzoic acid. Z imino compounds can be made by reacting compounds with Z amino with corresponding carbonyl.

The following Examples 1-6 are detailed descriptions of methods of preparation of certain compounds of the present invention. These detailed preparations fall within the scope of, and serve to exemplify, the more generally described methods of preparation set forth above. These Examples are presented for illustrative purposes only and are not intended as a restriction on the scope of the invention. All parts are by weight unless otherwise indicated.

EXAMPLE 1

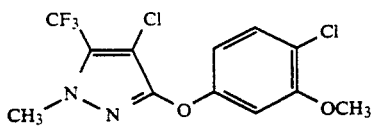

5-Trifluoromethyl-4-chloro-3-(3'-methoxy-4'-chlorophenoxy)-1-methylpyrazole (a) A 22-liter flask is charged with 2000 ml of DMSO and 2322 g of anhydrous potassium carbonate. The mixture is heated to 80° C. and both 3267 g (16.3 mol) of 5-trifluoromethyl-4-chloro-3-hydroxy-1 methyl pyrazole in 2000 ml of DMSO and 1564 g (7.81 mol) of 2,4 dichloronitrobenzene in 2000 ml of DMSO are added to the mixture. The mixture was stirred at 80° C. for 2½ hours and at 120° C. overnight. The mixture is cooled to room temperature and 10 l of water is added over 2 hours with cooling to 40° C. The mixture is stirred, filtered, washed and dried (air then vacuum) to give a solid.

(b) 3800 g of the product of step (a) is mixed with 9750 ml of t-butylalcohol at 60° C. under nitrogen to form a solution. 1500 ml of 5 molar potassium hydroxide in methanol is added dropwise over 3 hours. After two hours 5 l of the alcohol is stripped at 50° C. 60 torr and 10 l of water is added. The mixture is cooled to 10° C., stirred for ½ hour, filtered and washed with cold water. The solid is dried to give 2300 g of product.

(c) 52.7 g (0.15 mol) of the product of step (b) and 0.75 g of 5% palladium on carbon were added to 500 ml ethanol and the mixture was hydrogenated on a Parr hydrogenator at 40 psi until hydrogen uptake stopped (0.45 mol $H_2$). The mixture was filtered and solvent removed to give gray solid. Crystallization from 500 ml of hexane gave 40.0 g of a tan solid m.p. 64°–65° C.

(d) 2.58 g (0.019 mol) of cupric chloride was stirred in 50 ml of anhydrous acetonitrile under nitrogen at 55°–60° C. and 2.48 g (0.024 mole) of t-butyl nitrite was added. Then 5.15 g (0.016 mol) of the product of step (c) in 15 ml of acetonitrile was added dropwise. The mixture was stirred for 30 minutes, cooled and poured into 200 ml of ether. The ether was washed with 200 ml of 10% HCl, water, 200 ml of 1.5% sodium bicarbonate, water, brine and then dried over magnesium sulfate with carbon. The solution was filtered and evaporated to give 3.8 g of an dark oil which was purified by high pressure liquid chromatography (HPLC) (9% ethyl acetate in hexane) to give 2.6 g of a white solid (48%) m.p. 68°–69° C.

| Elemental Analysis For $C_{12}H_9F_3Cl_2N_2O_2$ | | | |
|---|---|---|---|
| | C | H | N |
| Calculated | 42.25 | 2.66 | 8.21 |
| Found | 42.34 | 2.69 | 8.17 |

EXAMPLE 2

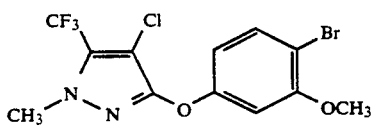

5-Trifluoromethyl-4-chloro-3-(3'methoxy-4'-bromophenoxy)-1-methylpyrazole (a) 4.3 g (0.019 mol) of anhydrous copper II bromide was stirred in 50 ml of anhydrous acetonitrile at 60° C. and 2.9 ml (0.22 mol) of t-butyl nitrite was added. To this mixture, 4.87 g (0.015 mol) of the product of Example 1(c) in 15 ml of acetonitrile was added dropwise with stirring. After one half hour, the product was isolated by ether extraction and purified by high pressure liquid chromatography (5% ethyl acetate in hexane) to give a yellow oil which solidified to give 2.9 g of a yellow solid (50% yield) m.p. 73.5°–75.5° C.

| Elemental Analysis For $C_{12}H_9F_3BrClN_2O_2$ | | | |
|---|---|---|---|
| | C | H | N |
| Calculated | 37.38 | 2.35 | 7.27 |
| Found | 37.48 | 2.39 | 7.23 |

EXAMPLE 3

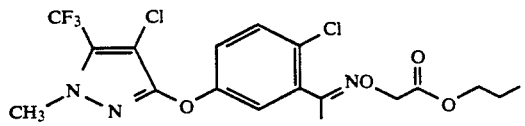

Acetic acid, [[[1-[2-chloro-5-[[4-chloro-1-methyl-5-(trifluoromethyl)-1H-pyrazol-3-yl]oxy]phenyl]ethylidene]amino]oxy]-, propyl ester (a) 18.2 g (0.05 mole) of 5-trifluoromethyl-4-chloro-3-(3'-methylcarbonyl-4-nitrophenoxy)-1-methylpyrazole was mixed with 0.5 g of 5% palladium on carbon in 125 ml of ethanol and hydrogenated on a Parr hydrogenator. The mixture was then filtered and evaporated to give a yellow-tan solid. The solid was crystallized from hexane to give 16.5 g (99%) of a yellow solid M.P. 90°–92° C.

(b) 6.72 g (0.05 mol) of cupric chloride was stirred in 125 ml of anhydrous acetonitrile under nitrogen at 50° C. and 7.1 ml of t-butyl nitrite was added. Then 13.34 g (0.04 mol) of the product of step (a) in 15 ml of acetonitrile was added dropwise. The mixture was stirred for 15 minutes, cooled and poured into 200 ml of ether. The ether was washed with 200 ml of 10% HCl, water, 200 ml of 1.5% sodium bicarbonate, water, brine and then dried over magnesium sulfate with carbon. The solution was filtered and evaporated to give 13.0 g of an orange solid which was purified by HPLC to give 11.9 g of a yellow solid (78%) m.p. 47°–48.5° C.

(c) 11.9 g (0.0337 mol) of the product of step (b) was combined with 8.74 g (0.04 mol) of aminoxyacetic acid hemihydrochloride and 3.28 g of sodium acetate were combined in 90 ml of methanol and heated under reflux for 1 hour. The mixture was filtered and evaporated. The residue was stirred in ether and water. The ether solution was washed with water, stirred with magnesium sulfate, filtered and evaporated to give 13.6 g of a yellow oil (refractive index at 25° C. is 1.5337) which crystalizes in about 1 month to a solid m.p. 72°–74° C.

(d) 2.74 g (0.0063 mol) of product of step (c) was combined with 50 ml of 1-propanol and 0.2 g of para toluene sulfonic acid and heated under reflux with a 3° A molecular sieve between the pot and condenser.

After 1 hour, the solvent was removed and the residue dissolved in ether and washed with 5% sodium bicarbonate, stirred with magnesium sulfate, filter and evaporated to give 2.9 g of a yellow oil (98% yield) (R.I. at 25° C. 1.5131.)

| Elemental Analysis For $C_{18}H_{18}F_3Cl_3N_3O_4$ | | | |
|---|---|---|---|
| | C | H | N |
| Calculated | 46.17 | 3.87 | 8.97 |
| Found | 46.26 | 3.87 | 8.95 |

EXAMPLE 4

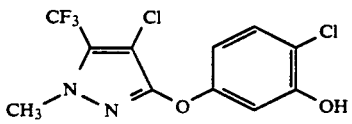

5-Trifluoromethyl-4-chloro-3-(3'hydroxy-4'-chlorophenoxy)-1-methylpyrazole 2 g (0.006 mol) of 5-trifluoromethyl-4-chloro-3-(3'-ethoxy-4-chlorophenoxy)-1-methylpyrazole was combined with 2 ml of HBr and 0.16 g of methyl tricapryl ammonium chloride and refluxed with stirring for 20 hours after removing aqueous forerun. The mixture was poured into water and extracted with ether. The ether layer was washed with water and brine, stirred with MgSO$_4$, filtered and evaporated to a solid which was purified by chromatography to give 0.9 g of a white solid m.p. 106°–108° C.

EXAMPLE 5

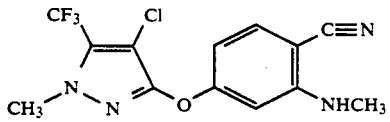

5-Trifluoromethyl-4-chloro-3-(3'-methylamino-4'-cyanophenoxy)-1-methylpyrazole (a) 16.5 g (0.1187 mol) of 2,4 difluorobenzonitrile, 24.2 ml of methylamine and 12.12 g (0.12 mol) of triethylamine were mixed in 100 ml of THF and stirred for 3 days. The reaction mixture was concentrated and added to 400 ml of ether. The ether was washed with water and brine, dried over magnesium sulfate and evaporated to give a colorless solid. The solid was crystallized from ether/cyclohexane, frozen, filtered, chromatographed with hexane and ethyl acetate to give 3.68 g of solid mp 115°–116° C.

(b) 1.5 g (0.01 mol) of the product of step (a) was combined with 2.2 g (0.011 mol) of 5-trifluoromethyl-4-chloro-3-hydroxy-1-methylpyrazole, 1.5 g of potassium carbonate in 20 ml of DMSO and heated under nitrogen at 100° C. for 16 hours and 120° C. for 24 hours. The mixture was diluted with 450 ml of water and extracted with ether. The ether layer was washed with water and brine and dried over MgSO$_4$. The solvent was removed and compound purified by chromatography (hexane/ethylacetate) to give 0.9 g (27%) of colorless solid m.p. 115°–117° C.

| Elemental Analysis For $C_{13}H_{10}ClF_3N_4O$ | | | |
|---|---|---|---|
| | C | H | N |
| Calculated | 47.22 | 3.05 | 16.94 |
| Found | 47.15 | 3.09 | 16.89 |

EXAMPLE 6

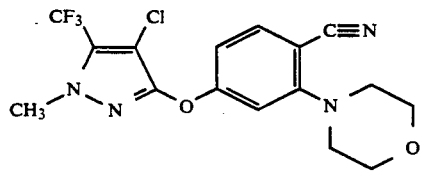

5-Trifluoromethyl-4-chloro-3-(3'-morpholinyl-4'-cyano)-1-methylpyrazole (a) 12 g (0.0863 mol) of 2,4-difluorobenzonitrile, 7.51 g (0.0863 mol) of morpholine; 8.76 g of triethylamine in 100 ml of THF were stirred for 5 days. The mixture was then concentrated, and mixed with methylene chloride. The methylene chloride was then washed with water and brine, dried over magnesium sulfate, concentrated and chromatographed (ethylacetate/hexane) to give 1.7 g of a clear liquid.

(b) 7.7 g (0.008 mol) of the product of step (a) was combined with 1.76 g (0.0088 mol) of 5-trifluoromethyl-4-chloro-3-hydroxy-1-methylpyrazole, 1.21 g of potassium carbonate and 45 ml of DMSO and heated at 150° C. for about 20 hours. The mixture was poured into 200 ml of water and extracted with methylene chloride. The methylene chloride was washed with water and brine, dried over magnesium sulfate, filtered, concentrated and chromatographed to give 2 g (65%) of solid M.P. 78°–80° C.

| Elemental Analysis For $C_{16}H_{14}ClF_3N_4O_2$ | | | |
|---|---|---|---|
| | C | H | N |
| Calculated | 49.64 | 3.64 | 14.48 |
| Found | 49.51 | 3.78 | 14.34 |

Using procedures similar to those set out in detail above, further compounds of the present invention were prepared and are shown in the following Table 1. Compounds without melting points are oils and refractive index are at room temperature.

| Ex CP # | Name | Structure |
|---|---|---|
| 7 | 1H-pyrazole, 4-chloro-3-(4-chlorophenoxy)-1-methyl-5-(trifluoromethyl)- MP: 70.0–72.5 nD: | 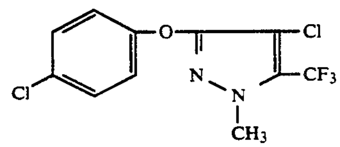 |
| 8 | acetic acid, [[[1-[2-chloro-5-[[4-chloro-1-methyl-5-(trifluoromethyl)-1H-pyrazol-3-yl]oxy]-phenyl]-ethylidene]amino]oxy]- MP: nD: 1.5337 | 80% E 20% Z ISOMER |
| 9 | ethanone, 1-[5-[[4-bromo-5-(difluoromethyl)-1-methyl-1H-pyrazol-3-yl]oxy]-2-chlorophenyl]- MP: 49.0–52.0 nD: | 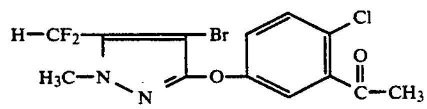 |
| 10 | ethanone, 1-[5-[[4-chloro-1-methyl-5-(trifluoromethyl)-1H-pyrazole-3-yl]oxy]-2-chlorophenyl]- MP: 47.5–50.0 nD: | 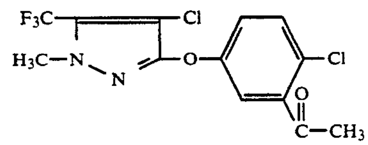 |
| 11 | 1H-pyrazole, 4-chloro-3-(4-chloro-2-fluoro-3-methoxyphenoxy)-1-methyl-5-(trifluoromethyl)-MP: nD: 1.5070 | 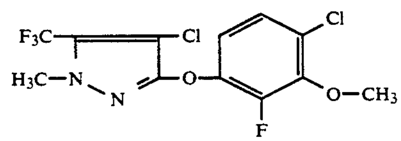 |
| 12 | 1H-pyrazole, 4-chloro-3-(4-chloro-3-ethoxy-phenoxy)-1-methyl-5-(trifluoromethyl)- MP: 37.5–39.0 nD: | 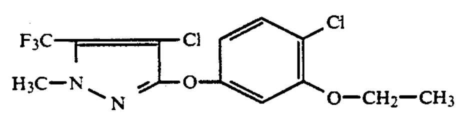 |
| 13 | 1H-pyrazole, 4-chloro-3-[4-chloro-3-(2-propenyloxy)phenyl]-1-methyl-5-(trifluoromethyl)- MP: nD: 1.5249 | 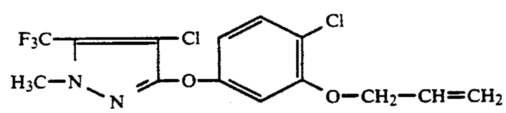 |
| 14 | propanamide, 2-[2-chloro-5-[[4-chloro-1-methyl-5-(trifluoromethyl)-1H-pyrazol-3-yl]oxy]-phenoxy]-N,N-dimethyl- MP: nD: 1.5246 | 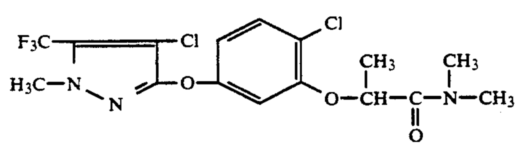 |
| 15 | 1H-pyrazole, 4-chloro-3-[4-chloro-3-(methylthio)-phenoxy]-5-(difluoromethyl)-1-methyl- MP: 53.5–55.0 nD: | 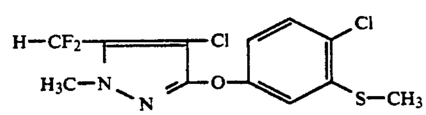 |
| 16 | 1H-pyrazole,-4-chloro-3-[4-chloro-3-(methylsulfinyl)phenoxy]-5-(difluoromethyl)-1-methyl- MP: 105.0–107.5 nD: | 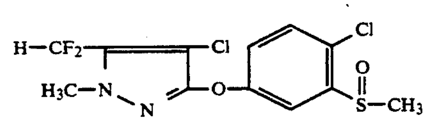 |
| 17 | 1H-pyrazole,-4-chloro-3-[4-chloro-3-(methylsulfonyl)phenoxy]-5-(difluoromethyl)-1-methyl- MP: 124.0–124.5 nD: | 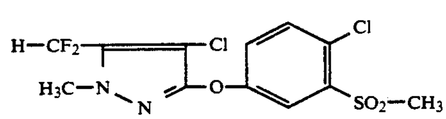 |

-continued

| Ex CP # | Name | Structure |
|---|---|---|
| 18 | 1H-pyrazole, 4-chloro-3-(4-chloro-2-fluoro-5-methoxyphenoxy)-1-methyl-5-(trifluoromethyl)- MP: 56.0–58.0 nD: | 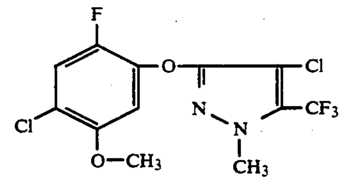 |
| 19 | 1H-pyrazole, 4-chloro-3-[4-chloro-2-fluoro-3-(2-propynyloxy)-phenoxy]-1-methyl-5-(trifluoromethyl)- MP: 83.0–85.0 nD: | 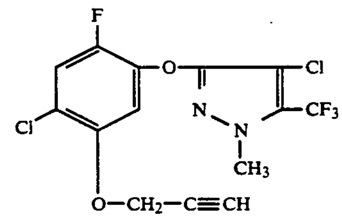 |
| 20 | propanoic acid, 2-[2-chloro-5-[[4-chloro-1-methyl-5-(trifluoromethyl)-1H-pyrazol-3-yl]oxy]-4-fluorophenoxy]-, ethyl ester MP: nD: | 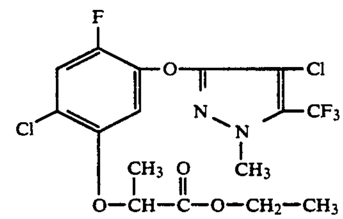 |
| 21 | 1H-pyrazole, 3-(4-bromophenoxy)-4-chloro-1-methyl-5-(trifluoromethyl)- MP: 71.5–72.5 nD: | 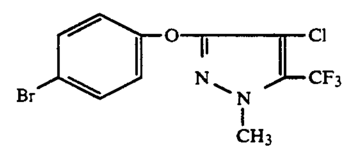 |
| 22 | benzoic acid, 2-bromo-5-[[4-chloro-1-methyl-5-(methylsulfonyl)-1H-pyrazol-3-yl]oxy]-, methyl ester MP: 111.5–114.5 nD: | 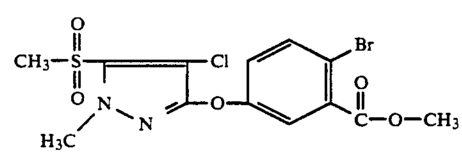 |
| 23 | 1H-pyrazole, 3-(4-bromo-3-ethoxyphenoxy)-4-chloro-1-methyl-5-(trifluoromethyl)- MP: 42.0–45.0 nD: | 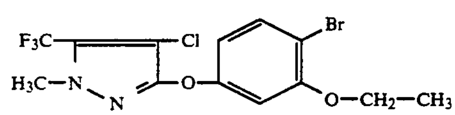 |
| 24 | 1H-pyrazole, 4-chloro-3-(4-iodo-3-methoxyphenoxy)-5-(trifluoromethyl)- MP: 70.5–72.0 nD: | 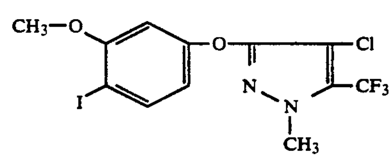 |
| 25 | 1H-pyrazole, 4-chloro-3-(3-ethoxy-4-iodophenoxy)-1-methyl-5-(trifluoromethyl)- MP: 59.5–61.5 nD: | 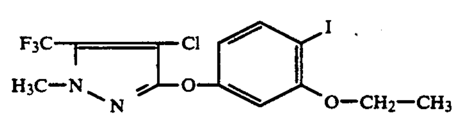 |
| 26 | propanamide, 2-[5-[[4-chloro-1-methyl-5-(trifluoromethyl)-1H-pyrazol-3-yl]oxy]-2-iodophenoxy]-N,N-dimethyl- MP: 97.0–100.0 nD: | 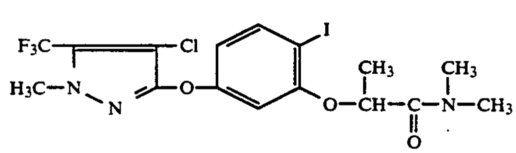 |

| Ex CP # | Name | Structure |
|---|---|---|
| 27 | 1H-pyrazole, 3-(4-fluorophenoxy)-1-methyl-5-(trifluoromethyl)-<br>MP:<br>nD: 1.4783 | 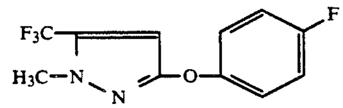 |
| 28 | benzenecarbonitrile, 4-[[4-chloro-1-methyl-5-(trifluoromethyl)-1H-pyrazol-3-yl]oxy]-<br>MP: 86.0–88.0<br>nD: | 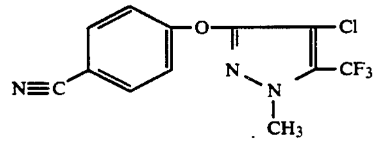 |
| 29 | benzonitrile, 4-[[4-chloro-1-methyl-5-(trifluoromethyl)-1H-pyrazol-3-yl]oxy]-2-methyl-<br>MP: 39.0–41.0<br>nD: | 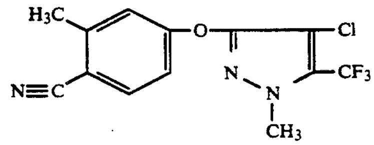 |
| 30 | benzonitrile, 4-[[4-chloro-1-methyl-5-(trifluoromethyl)-1H-pyrazol-3-yl]oxy]-2-(ethylamino)-<br>MP: 73.0–75.0<br>nD: | 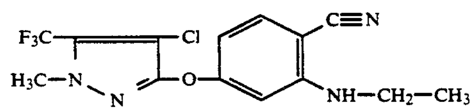 |
| 31 | benzonitrile, 4-[[4-chloro-1-methyl-5-(trifluoromethyl)-1H-pyrazol-3-yl]oxy]-2-(dimethylamino)-<br>MP: 82.0–84.0<br>nD: | 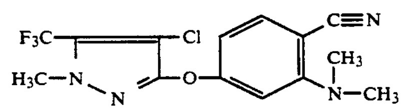 |
| 32 | benzonitrile, 4-[[4-chloro-1-methyl-5-(trifluoromethyl)-1H-pyrazol-3-yl]oxy]-2-(1-piperidinyl)-<br>MP:<br>nD: 1.5492 | 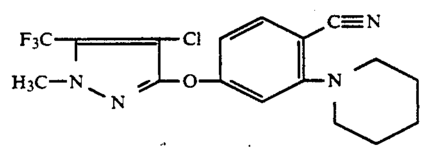 |
| 33 | benzonitrile, 4-[[4-chloro-1-methyl-5-(trifluoromethyl)-1H-pyrazol-3-yl]oxy]-2-methoxy-<br>MP: 45.0–50.0<br>nD: | 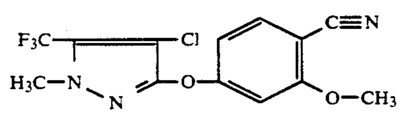 |
| 34 | benzonitrile, 5-[[4-chloro-1-methyl-5-(trifluoromethyl)-1H-pyrazol-3-yl]oxy]-2-ethoxy-<br>MP: 49.0–51.0<br>nD: | 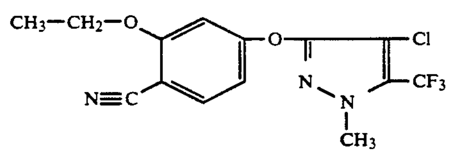 |
| 35 | benzonitrile, 4-[[4-chloro-1-methyl-5-(trifluoromethyl)-1H-pyrazol-3-yl]oxy]-2-propoxy-<br>MP: 55.0–56.0<br>nD: | 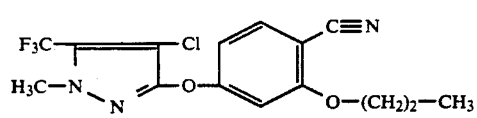 |
| 36 | benzonitrile, 2-butoxy-4-[[4-chloro-1-methyl-5-(trifluoromethyl)-1H-pyrazol-3-yl]oxy]-<br>MP:<br>nD: 1.5164 | 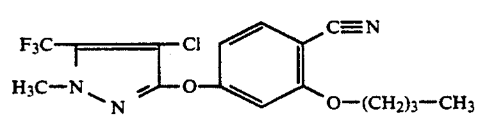 |
| 37 | benzonitrile, 4-[[4-chloro-1-methyl-5-(trifluoromethyl)-1H-pyrazol-3-yl]oxy]-2-(2-methylpropyl)-<br>MP:<br>nD: 1.5138 | 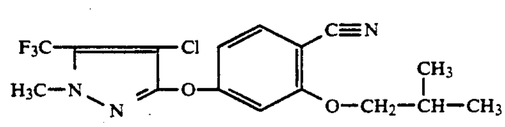 |

-continued

| Ex CP # | Name | Structure |
|---|---|---|
| 38 | benzonitrile, 4-[[4-chloro-1-methyl-5-(trifluoromethyl)-1H-pyrazol-3-yl]oxy]-2-(methylthio)- MP: 95.0–97.0 nD: | 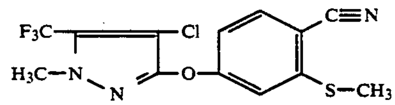 |
| 39 | 1H-pyrazol,- 4-chloro-3-[4-chloro-3-(2-propynyloxy)phenoxy]-1-methyl-5-(trifluoromethyl)- MP: nD: 1.5313 | 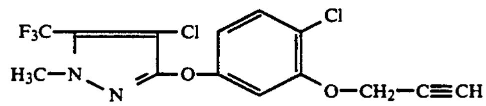 |
| 40 | pyridine, 4-[[2-chloro-5-[[4-chloro-1-methyl-5-(trifluoromethyl)-1H-pyrazol-3-yl]oxy]phenoxy]methyl]- MP: 83.0–85.0 nD: | 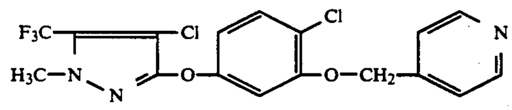 |
| 41 | acetic acid, [[[1-[5-[[4-bromo-5-(difluoromethyl)-1-methyl-1H-pyrazol-3-yl]oxy]-2-chlorophenyl]ethylidene]amino]oxy]-, propyl ester MP: nD: 1.5000 | 82% E 18% Z ISOMER |
| 42 | benzenamine, -2-chloro-5-[[4-chloro-1-methyl-5-(trifluoromethyl)-1H-pyrazol-3-yl]oxy]-N,N-dimethyl- MP: nD: 1.5326 | 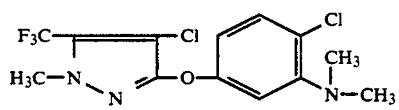 |
| 43 | benzenamine, 5[[4-chloro-1-methyl-5-(trifluoromethyl)-1H-pyrazol-3-yl]oxy]-2-iodo-N,N-dimethyl- MP: nD: 1.5652 | 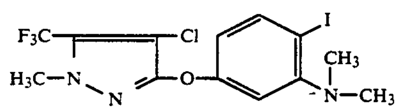 |
| 44 | 1H-pyrazole, 4-chloro-3-[4-chloro-3-[(trimethylsilyl)methoxy]-phenoxy]-1-methyl-5-(trifluoromethyl)- MP: nD: 1.5066 | 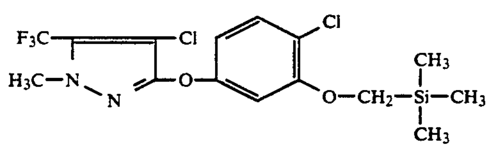 |
| 45 | propanoic acid, 2-[2-chloro-5-[[4-chloro-1-methyl-5-(trifluoromethyl)-1H-pyrazol-3-yl]oxy]phenoxy]- MP: 117.0–118.0 nD: | 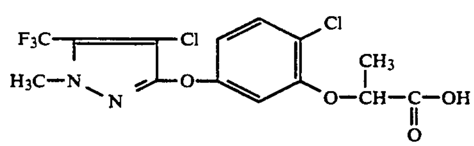 |
| 46 | propanamide, 2-[2-chloro-5-[[4-chloro-1-methyl-5-(trifluoromethyl)-1H-pyrazol-3-yl]oxy]phenoxy]-N-methyl- MP: 101.0–104.0 nD: | 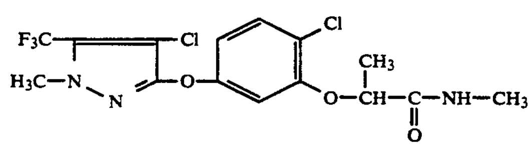 |
| 47 | 1H-pyrazole, 4-chloro-3-[4-chloro-3-(methoxymethoxy)-phenoxy]-1-methyl-5-(trifluoromethyl)- MP: nD: 1.5128 | 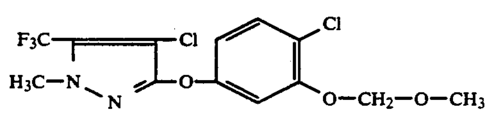 |
| 48 | 1H-pyrazole,- 3-[3-(2-bromoethoxy)-4-chlorophenoxy]-4-chloro-1-methyl-5-(trifluoromethyl)- MP: nD: 1.5412 | 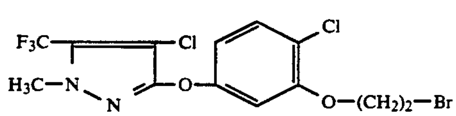 |

| Ex CP # | Name | Structure |
|---|---|---|
| 49 | 1H-pyrazole, 4-chloro-3-[4-chloro-3-(2-methoxyethoxy)-phenoxy]-1-methyl-5-(trifluoromethyl)- MP: 104.0 nD: | 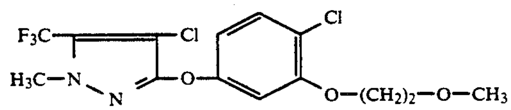 |
| 50 | 1H-pyrazole, 4-chloro-3-[4-chloro-3-(ethenyloxy)-phenoxy]-1-methyl-5-(trifluoromethyl)- MP: nD: 1.5280 | 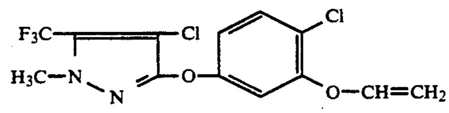 |
| 51 | 1H-pyrazole,- 4-chloro-3-[4-chloro-3-(2-phenylethoxy)phenoxy]-1-methyl-5-(trifluoromethyl)- MP: nD: 1.5500 | 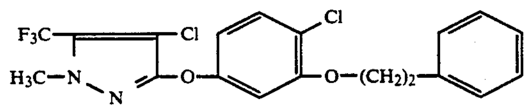 |
| 52 | propanamide, 2-[2-chloro-5-[[4-chloro-1-methyl-5-(trifluoromethyl)-1H-pyrazol-3-yl]oxy]phenoxy]-N-(methylsulfonyl)- MP: 118.0–121.0 nD: — | 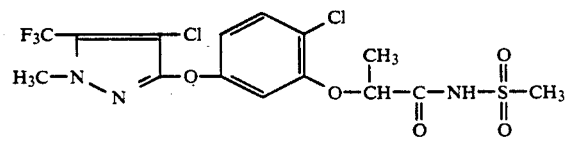 |
| 53 | benzonitrile, 4-[[4-chloro-1-methyl-5-(trifluoromethyl)-1H-pyrazol-3-yl]oxy]-2-[(3-hydroxypropyl)amino]- MP: 53.0–57.0 nD: | 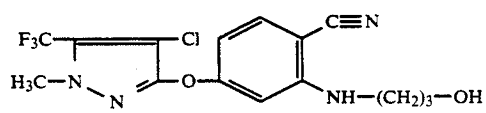 |
| 54 | benzonitrile, 4-[[4-chloro-1-methyl-5-(trifluoromethyl)-1H-pyrazol-3-yl]oxy]-2-(ethylthio)- MP: 57.0–60.0 nD: | 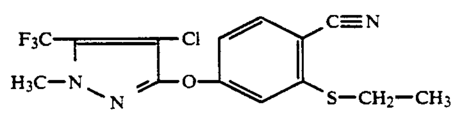 |
| 55 | benzonitrile, 4-[[4-chloro-1-methyl-5-(trifluoromethyl)-1H-pyrazol-3-yl]oxy]-2-(methylsulfinyl)- MP: 84.0–86.0 nD: | 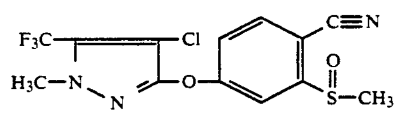 |
| 56 | benzonitrile, 4-[[4-chloro-1-methyl-5-(trifluoromethyl)-1H-pyrazol-3-yl]oxy]-2-(methylsulfonyl)- MP: 121.0–123.0 nD: | 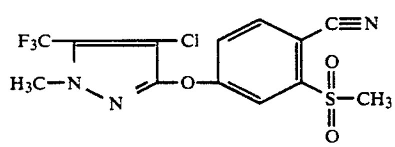 |
| 57 | acetonitrile, [2-chloro-5-[[4-chloro-1-methyl-5-(trifluoromethyl)-1H-pyrazol-3-yl]oxy]phenoxy]- MP: 72.0–73.0 nD: | 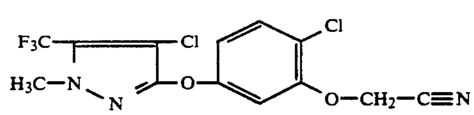 |
| 58 | 1H-pyrazole, 4-chloro-3-(4-fluorophenoxy)-1-methyl-5-(trifluoromethyl)- MP: nD: 1.4929 | 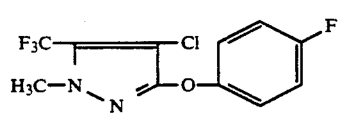 |
| 59 | 1H-pyrazole, 4-chloro-3-(4-fluoro-3-methylphenoxy)-1-methyl-5-(trifluoromethyl)- MP: nD: 1.4953 | 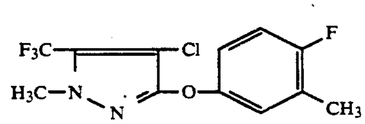 |
| 60 | 1H-pyrazole, 4-chloro-3-(4-fluorophenoxy)-1-methyl-5-(methylthio)- MP: 57.0–58.0 nD: — | 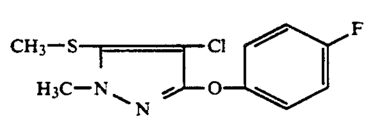 |

| Ex CP # | Name | Structure |
|---|---|---|
| 61 | 1H-pyrazole, 4-chloro-3-(4-fluorophenoxy)-1-methyl-5-(methylsulfinyl)- MP: 75.0–77.0 nD: — | 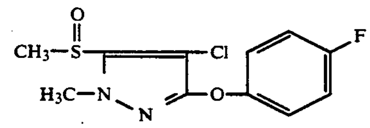 |
| 62 | 1H-pyrazole, 4-chloro-3-(4-fluorophenoxy)-1-methyl-5-(methylsulfonyl)- MP: 108.0–109.0 nD: — | 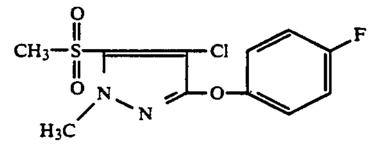 |
| 63 | 1H-pyrazole, 4-chloro-3-(4-chloro-3-methyl-phenoxy)-1-methyl-5-(trifluoromethyl)- MP: nD: 1.5185 | 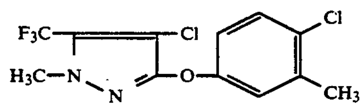 |
| 64 | 1H-pyrazole, 4-chloro-3-[4-chloro-3-[2-(ethylthio)-ethoxy]phenoxy]-1-methyl-5-(trifluoromethyl)- MP: nD: 1.5338 | 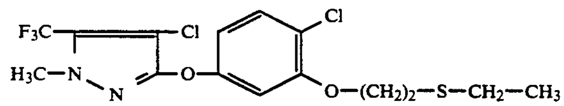 |
| 65 | 1H-pyrazole, 4-chloro-3-[4-chloro-3-[2-(ethylsulfinyl)-ethoxy]phenoxy]-1-methyl-5-(trifluoromethyl)- MP: 77.0–80.0 nD: — | 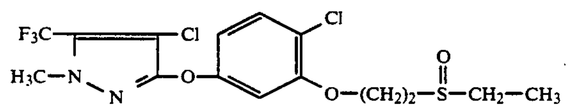 |
| 66 | 1H-pyrazole, 4-chloro-3-[4-chloro-3-[2-(ethylsulfonyl)-ethoxy]phenoxy]-1-methyl-5-(trifluoromethyl)- MP: 91.0–94.0 nD: — | 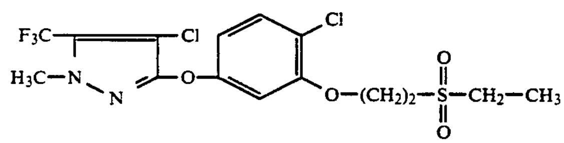 |
| 67 | propanamide, 2-[2-chloro-5-[[4-chloro-1-methyl-5-(trifluoromethyl)-1H-pyrazol-3-yl]oxy]phenoxy]-N-phenyl- MP: 87.0–90.0 nD: — | 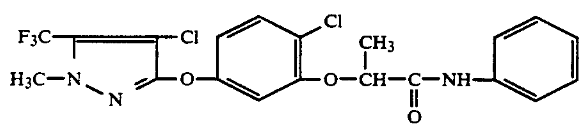 |
| 68 | propanoic acid, 2-[2-chloro-5-[[4-chloro-1-methyl-5-(trifluoromethyl)-1H-pyrazol-3-yl]oxy]phenoxy]-, methyl ester MP: nD: 1.5115 | 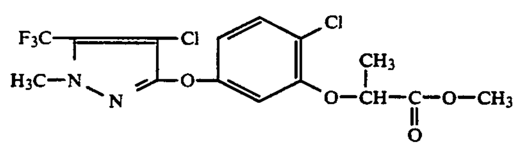 |
| 69 | propanoic acid, 2-[2-[2-chloro-5-[[4-chloro-1-methyl-5-(trifluoromethyl)-1H-pyrazol-3-yl]oxy]phenoxy]-1-oxopropoxy]-, methyl ester, (R)- MP: nD: 1.5030 | R ISOMER |
| 70 | propanoic acid, 2-[2-[2-chloro-5-[[4-chloro-1-methyl-5-(trifluoromethyl)-1H-pyrazol-3-yl]oxy]phenoxy]-1-oxopropoxy]-, methyl ester, (S)- MP: nD: 1.5030 | S ISOMER |

| Ex CP # | Name | Structure |
|---|---|---|
| 71 | propanethioic acid, 2-[2-chloro-5-[[4-chloro-1-methyl-5-(trifluoromethyl)-1H-pyrazol-3-yl]oxy]phenoxy]-, S-butyl ester<br>MP:<br>nD: 1.5248 | 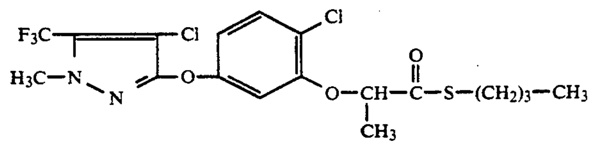 |
| 72 | butanamide, 2-[2-chloro-5-[[4-chloro-1-methyl-5-(trifluoromethyl)-1H-pyrazol-3-yl]oxy]phenoxy]-N-methyl-<br>MP: 93.0–94.0<br>nD: — | 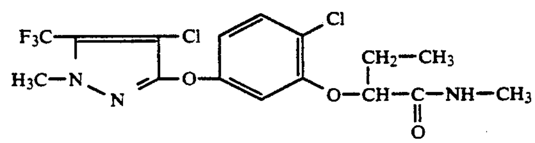 |
| 73 | butanoic acid, 2-[2-chloro-5-[[4-chloro-1-methyl-5-(trifluoromethyl)-1H-pyrazol-3-yl]oxy]phenoxy]-, 2,2-dimethylhydrazide<br>MP: 101.0–102.5<br>nD: — | 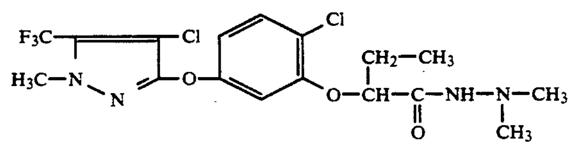 |
| 74 | butanoic acid, 2-[2-chloro-5-[[4-chloro-1-methyl-5-(trifluoromethyl)-1H-pyrazol-3-yl]oxy]phenoxy]-, ethyl ester<br>MP:<br>nD: 1.5036 | 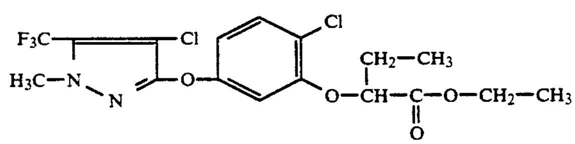 |
| 75 | 1H-pyrazole, 4-chloro-3-[4-chloro-3-(cyclopropylmethoxy)phenoxy]-1-methyl-5-(trifluoromethyl)-<br>MP:<br>nD: 1.5263 | 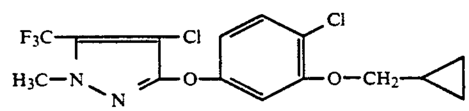 |
| 76 | 1H-pyrazole, 4-chloro-3-[4-chloro-3-(1,3-dioxolan-2-ylmethoxy)phenoxy]-1-methyl-5-(trifluoromethyl)-<br>MP:<br>nD: 1.5256 | 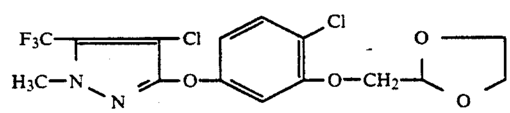 |
| 77 | 1H-pyrazole, 4-chloro-3-[4-chloro-3-(1-naphthalenylmethoxy)phenoxy]-1-methyl-5-(trifluoromethyl)-<br>MP: 101.0–104.0<br>nD: — | 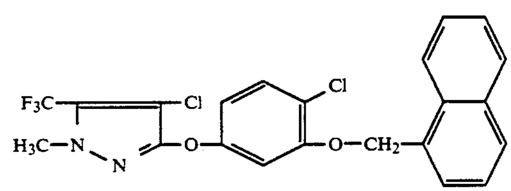 |
| 78 | 1H-pyrazole, 4-chloro-3-(4-iodo-3-methylphenoxy)-1-methyl-5-(trifluoromethyl)-<br>MP: 32.0–34.0<br>nD: — | 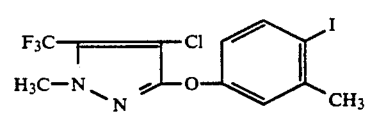 |
| 79 | benzoic acid, 5-[[4-chloro-1-methyl-5-(trifluoromethyl)-1H-pyrazol-3-yl]oxy]-2-iodo-, methyl ester<br>MP:<br>nD: 1.5250 | 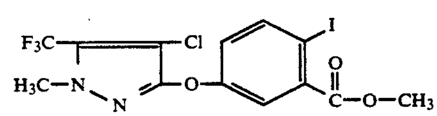 |
| 80 | benzonitrile, 4-[[4-chloro-1-methyl-5-(trifluoromethyl)-1H-pyrazol-3-yl]oxy]-2-fluoro-<br>MP: 46.0–60.0<br>nD: — | 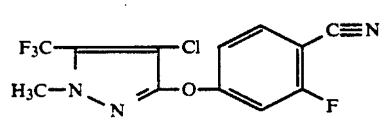 |
| 81 | benzonitrile, 4-[[4-chloro-1-methyl-5-(trifluoromethyl)-1H-pyrazol-3-yl]oxy]-2-(1-pyrrolidinyl)-<br>MP: 60.0–64.0<br>nD: — | 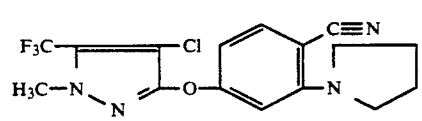 |

-continued

| Ex CP # | Name | Structure |
|---|---|---|
| 82 | benzonitrile, 4-[[4-chloro-1-methyl-5-(trifluoromethyl)-1H-pyrazol-3-yl]oxy]-2-hydroxy- MP: 147.0-148.0 nD: — | 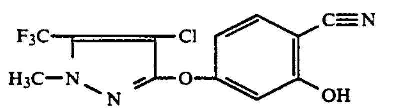 |
| 83 | benzonitrile, 2,4-bis[[4-chloro-1-methyl-5-(trifluoromethyl)-1H-pyrazol-3-yl]oxy]- MP: 96.0-97.0 nD: — | 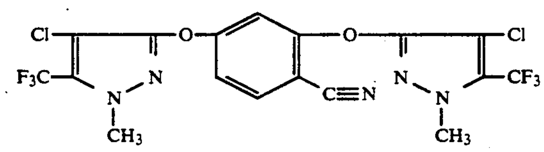 |
| 84 | benzonitrile 2-(butylthio)-4-[[4-chloro-1-methyl-5-(trifluoromethyl)-1H-pyrazol-3-yl]oxy]- MP: nD: 1.5443 | 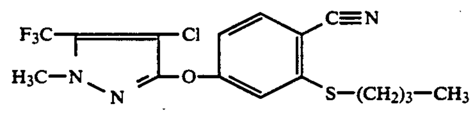 |
| 85 | benzonitrile, 4-[[4-chloro-1-methyl-5-(methylthio)-1H-pyrazol-3-yl]oxy]-2-(1-pyrrolidinyl)- MP: 84.0-86.0 nD: — | 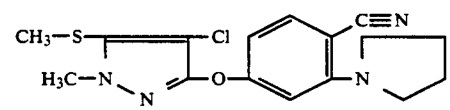 |
| 86 | benzonitrile, 4-[[4-chloro-1-methyl-5-(methylthio)-1H-pyrazol-3-yl]oxy]-2-(1-piperidinyl)- MP: 75.0-77.0 nD: — | 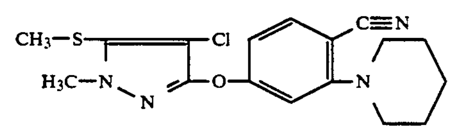 |

PRE-EMERGENT ACTIVITY ON WEEDS

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amount of active ingredient was equivalent to an application rate of 11.2 kg/ha. After treatment, the pans were moved to a greenhouse bench where they were watered as needed to give adequate moisture for germination and growth.

Approximately 10–14 days (usually 14 days) after planting and treating, the pans were observed and the results recorded.

The plant species usually regarded as weeds which were utilized in one set of pre-emergent activity tests, the data for which are shown in Table A, are identified by letter headings printed diagonally above the columns according to the following legend:

CATH—Canada thistle*
RHQG—Quackgrass*
COBU—Cocklebur
RHJG—Rhizome Johnsongrass*
VELE—Velvetleaf
DOBR—Downy Brome
MOGL—Morningglory
BYGR—Barnyardgrass
COLQ—Common Lambsquarters
ANBG—Annual Bluegrass
PESW—Pennsylvania Smartweed
SEJG—Seedling Johnsongrass
YENS—Yellow Nutsedge*
INMU—Indian Mustard
WIBW—Wild Buckwheat
*Grown from vegetative propagules In Table A, the first column is the application rate of the compound being tested in

PRE-EMERGENT HERBICIDE EXAMPLES

As noted above, compounds of this invention have been found to be effective as herbicides, particularly pre-emergent herbicides. Table A summarizes results of tests conducted to determine the pre-emergent herbicidal activity of the compounds of this invention. The herbicidal ratings used in Table A was assigned according to a scale based on the percent inhibition of each plant species. The herbicide rating symbols in Table A is defined as follows:

| % Inhibition | Rating |
|---|---|
| 0-24 | 0 |
| 25-49 | 1 |
| 50-74 | 2 |
| 75-100 | 3 |
| Not planted | — or a blank |
| Species planted No data | N |

Footnotes are shown at the end of the table.

For some compounds of this invention data were originally recorded as percent inhibition (or control) in ten percent increments. Where this system was used, the percentages have been mathematically converted to the above equivalent system using the correlation table above.

TABLE A

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 2 | 11.2100 | 2 | | | 3 | 3 | 3 | 2 | 3 | | | 1 | 3 | 3 | 3 | 0 |
| 1 | 11.2100 | 3 | | | 3 | 3 | 3 | 3 | 3 | | | 3 | 3 | 3 | 3 | 2 |
| 3 | 11.2100 | 0 | 0 | 3 | 3 | 3 | 3 | 2 | 3 | 2 | 3 | | | | | |
| 4 | 11.2100 | 0 | 0 | 0 | 1 | 1 | 2 | 0 | 3 | 0 | 3 | | | | | |
| 5 | 11.2100 | 0 | 3 | 3 | 3 | 3 | 3 | 1 | 3 | 3 | 3 | | | | | |
| 7 | 11.2100 | 2 | | | 3 | 3 | 3 | 1 | 3 | | | 3 | 3 | 3 | 3 | 3 |
| 8 | 11.2100 | 0 | 0 | 3 | 3 | 3 | 3 | 3 | 3 | 2 | 3 | | | | | |
| 10 | 11.2100 | 0 | 3 | 3 | 3 | 3 | 3 | 2 | 3 | 3 | 3 | | | | | |
| 11 | 11.2100 | 0 | 3 | 3 | 3 | 0 | 0 | 0 | 1 | 0 | 3 | | | | | |
| 12 | 11.2100 | 1 | 3 | 3 | 3 | 3 | 3 | 2 | 3 | 3 | 3 | | | | | |
| 13 | 11.2100 | 0 | 3 | 3 | 3 | 3 | 2 | 0 | 3 | 3 | 3 | | | | | |
| 15 | 11.2100 | 1 | 3 | 3 | 3 | 3 | 3 | 1 | 3 | 3 | 3 | | | | | |
| 16 | 11.2100 | 2 | 3 | 3 | 3 | 3 | 3 | 0 | 3 | 3 | 3 | | | | | |
| 18 | 11.2100 | 1 | 3 | 3 | 3 | 3 | 3 | 1 | 3 | 3 | 3 | | | | | |
| 19 | 11.2100 | 0 | 3 | 3 | 3 | 3 | 3 | 0 | 3 | 3 | 3 | | | | | |
| 20 | 11.2100 | 1 | 3 | 3 | 3 | 3 | 3 | 3 | 3 | 3 | 3 | | | | | |
| 21 | 11.2100 | 0 | | | 3 | 3 | 3 | 0 | 3 | | | 1 | 3 | 3 | 2 | 3 |
| 22 | 11.2100 | 0 | 3 | 2 | 2 | 3 | 3 | 0 | 3 | 3 | 3 | | | | | |
| 23 | 11.2100 | 0 | 3 | 3 | 3 | 3 | 3 | 2 | 3 | 3 | 3 | | | | | |
| 24 | 11.2100 | 1 | | | 3 | 3 | 3 | 0 | 3 | | | 1 | 3 | 3 | 3 | 0 |
| 25 | 11.2100 | 0 | 3 | 3 | 3 | 3 | 2 | 1 | 3 | 2 | 3 | | | | | |
| 26 | 11.2100 | 0 | 3 | 3 | 3 | 3 | 3 | 2 | 3 | 3 | 3 | | | | | |
| 28 | 11.2100 | 1 | | | 3 | 3 | 3 | 0 | 3 | | | 1 | 3 | 3 | 2 | 1 |
| 29 | 11.2100 | 1 | 3 | 3 | 3 | 3 | 3 | 1 | 3 | 3 | 3 | | | | | |
| 30 | 11.2100 | 0 | 3 | 3 | 3 | 3 | 3 | 0 | 3 | 3 | 3 | | | | | |
| 33 | 11.2100 | 3 | 3 | 3 | 3 | 3 | 3 | 2 | 3 | 3 | 3 | | | | | |
| 34 | 11.2100 | 1 | 3 | 3 | 3 | 3 | 3 | 3 | 3 | 3 | 3 | | | | | |
| 35 | 11.2100 | 0 | 3 | 3 | 3 | 3 | 3 | 0 | 3 | 3 | 3 | | | | | |
| 36 | 11.2100 | 2 | 3 | 3 | 3 | 3 | 2 | 2 | 2 | 0 | 3 | | | | | |
| 37 | 11.2100 | 0 | 3 | 3 | 3 | 3 | 2 | 0 | 2 | 0 | 3 | | | | | |
| 38 | 11.2100 | 0 | 3 | 3 | 3 | 3 | 3 | 0 | 3 | 3 | 3 | | | | | |
| 39 | 11.2100 | 0 | 3 | 3 | 3 | 3 | 3 | 2 | 3 | 3 | 3 | | | | | |
| 40 | 11.2100 | 0 | 2 | 2 | 2 | 3 | 1 | 0 | 2 | 2 | 3 | | | | | |
| 41 | 11.2100 | 0 | 0 | 3 | 3 | 3 | 3 | 3 | 3 | 3 | 3 | | | | | |
| 42 | 11.2100 | 0 | 3 | 3 | 3 | 3 | 3 | 2 | 3 | 3 | 3 | | | | | |
| 43 | 11.2100 | 0 | 3 | 3 | 3 | 3 | 3 | 0 | 3 | 3 | 3 | | | | | |
| 44 | 11.2100 | 0 | 3 | 3 | 3 | 3 | 2 | 0 | 0 | 0 | 3 | | | | | |
| 45 | 11.2100 | 2 | 0 | 2 | 1 | 3 | 3 | 3 | 3 | 0 | 3 | | | | | |
| 46 | 11.2100 | 2 | 3 | 3 | 3 | 3 | 3 | 2 | 3 | 3 | 3 | | | | | |
| 47 | 11.2100 | 2 | 3 | 3 | 3 | 3 | 3 | 3 | 3 | 3 | 3 | | | | | |
| 48 | 11.2100 | 0 | 3 | 3 | 3 | 3 | 3 | 3 | 3 | 3 | 3 | | | | | |
| 49 | 11.2100 | 0 | 3 | 3 | 3 | 3 | 3 | 2 | 3 | 3 | 3 | | | | | |
| 50 | 11.2100 | 0 | 3 | 3 | 3 | 3 | 3 | 3 | 3 | 3 | 3 | | | | | |
| 51 | 11.2100 | 0 | 2 | 3 | 1 | 3 | 2 | 0 | 2 | 1 | 2 | | | | | |
| 52 | 11.2100 | 1 | 0 | 2 | 0 | 3 | 3 | 2 | 3 | 3 | 3 | | | | | |
| 53 | 11.2100 | 0 | 2 | 1 | 0 | 3 | 3 | 2 | 3 | 0 | 3 | | | | | |
| 54 | 11.2100 | 0 | 3 | 3 | 3 | 3 | 3 | 0 | 3 | 2 | 3 | | | | | |
| 55 | 11.2100 | 2 | 2 | 3 | 2 | 3 | 3 | 0 | 3 | 3 | 3 | | | | | |
| 56 | 11.2100 | 2 | 2 | 3 | 1 | 3 | 3 | 0 | 3 | 3 | 3 | | | | | |
| 57 | 11.2100 | 3 | 2 | 3 | 1 | 3 | 3 | 3 | 3 | 3 | 3 | | | | | |
| 58 | 11.2100 | 0 | 2 | 3 | 2 | 2 | 3 | 1 | 3 | 1 | 3 | | | | | |
| 59 | 11.2100 | 0 | 1 | 3 | 2 | 3 | 3 | 0 | 3 | 3 | 3 | | | | | |
| 60 | 11.2100 | 1 | 3 | 3 | 3 | 3 | 3 | 0 | 3 | 3 | 3 | | | | | |
| 61 | 11.2100 | 2 | 2 | 3 | 3 | 3 | 3 | 1 | 3 | 3 | 3 | | | | | |
| 62 | 11.2100 | 2 | 3 | 3 | 3 | 3 | 3 | 2 | 3 | 3 | 3 | | | | | |
| 63 | 11.2100 | 2 | 3 | 3 | 3 | 3 | 3 | 3 | 3 | 3 | 3 | | | | | |
| 64 | 11.2100 | 2 | 3 | 3 | 3 | 3 | 3 | 2 | 3 | 3 | 3 | | | | | |
| 65 | 11.2100 | 1 | 2 | 2 | 2 | 3 | 3 | 2 | 3 | 3 | 3 | | | | | |
| 66 | 11/2100 | 2 | 2 | 3 | 2 | 3 | 3 | 2 | 3 | 2 | 3 | | | | | |
| 67 | 11.2100 | 2 | 0 | 2 | 1 | 3 | 3 | 2 | 3 | 2 | 2 | | | | | |
| 68 | 11.2100 | 3 | 0 | 3 | 3 | 3 | 3 | 3 | 3 | 3 | 3 | | | | | |
| 69 | 11.2100 | 2 | 0 | 3 | 2 | 3 | 3 | 3 | 3 | 3 | 3 | | | | | |
| 70 | 11.2100 | 2 | 1 | 3 | 2 | 3 | 3 | 3 | 3 | 3 | 3 | | | | | |
| 71 | 11.2100 | 1 | 0 | 3 | 3 | 3 | 3 | 3 | 3 | 3 | 3 | | | | | |
| 72 | 11.2100 | 2 | 3 | 3 | 3 | 3 | 3 | 3 | 3 | 3 | 3 | | | | | |
| 73 | 11.2100 | 1 | 3 | 3 | 3 | 3 | 2 | 2 | 3 | 3 | 3 | | | | | |
| 74 | 11.2100 | 2 | 2 | 3 | 3 | 3 | 3 | 3 | 3 | 3 | 3 | | | | | |
| 75 | 11.2100 | 1 | 3 | 3 | 3 | 3 | 3 | 2 | 3 | 2 | 3 | | | | | |
| 76 | 11.2100 | 1 | 3 | 3 | 3 | 3 | 3 | 2 | 3 | 3 | 3 | | | | | |
| 77 | 11.2100 | 0 | 3 | 3 | 3 | 3 | 3 | 0 | 3 | 2 | 3 | | | | | |
| 78 | 11.2100 | 0 | 3 | 3 | 3 | 3 | 3 | 2 | 3 | 3 | 3 | | | | | |
| 79 | 11.2100 | 2 | 3 | 3 | 3 | 3 | 3 | 1 | 3 | 3 | 3 | | | | | |
| 80 | 11.2100 | 1 | 3 | 3 | 3 | 3 | 3 | 3 | 3 | 1 | 3 | | | | | |
| 81 | 11.2100 | 0 | 0 | 0 | 0 | 0 | 0 | 0 | 0 | 0 | 0 | | | | | |
| 82 | 11.2100 | 0 | | | 0 | 0 | 0 | 0 | 0 | | | 0 | 0 | 0 | 0 | N |

TABLE A-continued

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 83 | 11.2100 | 0 | 3 | 3 | 3 | 3 | 2 | 0 | 2 | 0 | 1 | | | | | |
| 84 | 11.2100 | 0 | 2 | 3 | 2 | 2 | 3 | 0 | 1 | 2 | 3 | | | | | |
| 85 | 11.2100 | 0 | 3 | 3 | 2 | 3 | 2 | 0 | 3 | 3 | 3 | | | | | |
| 86 | 11.2100 | 0 | 0 | 0 | 0 | 0 | 0 | 0 | 0 | 0 | 0 | | | | | |

POST-EMERGENT HERBICIDE EXAMPLES

The post-emergence herbicidal activity of compounds of this invention was demonstrated by greenhouse testing, and the results are shown in the following Table B. The post-emergent herbicidal activity index used in Table B is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |
| Species not planted | — or a blank |
| Species planted, no data | N |

Where appropriate, footnotes are shown at the end of the table.

As was the case with the pre-emergence data, some of the compounds initially received ratings for plant response directly as percent inhibition in ten percent increments. Where this is the case, the percentage have generally been converted according to the scale above.

POST-EMERGENCE ACTIVITY ON WEEDS

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (9–16 days), each pan (except the control pans) was removed to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/Ha (200 gallons/acre). The pans were returned to the greenhouse and watered as before and the injury to the plants as compared to those in control pans was observed at approximately 10–14 days (usually 14 days) and in some instances observed again at 24–28 days (usually 28 days) after spraying. These latter observations are designated by a "pound" sign (#) following the column of example numbers in the Table. The plant species used in this set of tests were the same as those used in the first set of pre-emergence tests, and the plant identifying codes are the same as those shown for Table A.

TABLE B

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 2 | 11.2100 | 0 | | | 1 | 3 | 3 | 2 | 3 | | | 0 | 4 | 3 | 0 | 0 |
| 1 | 11.2100 | 1 | | | 2 | 3 | 4 | 3 | 4 | | | 4 | 4 | 4 | 1 | 0 |
| 3 | 11.2100 | 0 | 3 | 3 | 3 | 4 | 4 | 4 | 4 | 4 | 4 | | | | | |
| 4 | 11.2100 | 0 | 1 | 3 | 1 | 2 | 2 | 1 | 4 | 1 | 4 | | | | | |
| 5 | 11.2100 | 1 | 1 | 3 | 0 | 3 | 3 | 0 | 3 | 2 | 4 | | | | | |
| 7 | 11.2100 | 0 | | | 0 | 0 | 1 | 0 | 0 | | | 0 | 1 | 1 | 0 | 0 |
| 8 | 11.2100 | 0 | 2 | 3 | 3 | 3 | 4 | 4 | 4 | 3 | 3 | | | | | |
| 10 | 11.2100 | 0 | 1 | 3 | 3 | 3 | 3 | 0 | 3 | 1 | 4 | | | | | |
| 11 | 11.2100 | 0 | 0 | 0 | 0 | 1 | 1 | 1 | 1 | 1 | 1 | | | | | |
| 12 | 11.2100 | 0 | 4 | 4 | 4 | 3 | 4 | 2 | 4 | 3 | 4 | | | | | |
| 13 | 11.2100 | 0 | 4 | 4 | 4 | 4 | 3 | 2 | 4 | 2 | 4 | | | | | |
| 15 | 11.2100 | 0 | 3 | 4 | 4 | 4 | 4 | 3 | 4 | 3 | 4 | | | | | |
| 16 | 11.2100 | 0 | 2 | 3 | 2 | 3 | 4 | 2 | 4 | 3 | 4 | | | | | |
| 18 | 11.2100 | 2 | 4 | 4 | 4 | 4 | 3 | 2 | 4 | 4 | 4 | | | | | |
| 19 | 11.2100 | 0 | 4 | 4 | 4 | 4 | 3 | 2 | 4 | 3 | 4 | | | | | |
| 20 | 11.2100 | 2 | 4 | 4 | 4 | 4 | 4 | 4 | 4 | 4 | 4 | | | | | |
| 21 | 11.2100 | 0 | | | 0 | 0 | 1 | 0 | 1 | | | — | 1 | 1 | 0 | 1 |
| 22 | 11.2100 | 0 | 0 | 0 | 3 | 3 | 4 | 3 | 4 | 3 | 4 | | | | | |
| 23 | 11.2100 | 0 | 3 | 4 | 4 | 4 | 3 | 2 | 4 | 2 | 4 | | | | | |
| 24 | 11.2100 | 1 | | | 2 | 3 | 3 | 1 | 4 | | | 1 | 4 | 4 | 1 | 1 |
| 25 | 11.2100 | 0 | 4 | 4 | 4 | 4 | 3 | 1 | 4 | 2 | 4 | | | | | |
| 26 | 11.2100 | 0 | 3 | 4 | 4 | 3 | 3 | 1 | 4 | 2 | 2 | | | | | |
| 28 | 11.2100 | 0 | | | 0 | 1 | 2 | 0 | 2 | | | 0 | 1 | 2 | 0 | 0 |
| 29 | 11.2100 | 1 | 0 | 0 | 0 | 2 | 2 | 0 | 3 | 1 | N | | | | | |
| 30 | 11.2100 | 1 | 2 | 3 | 3 | 3 | 4 | 1 | 4 | 2 | N | | | | | |
| 33 | 11.2100 | 1 | 4 | 4 | 4 | 4 | 4 | 2 | 4 | 3 | 4 | | | | | |
| 34 | 11.2100 | 0 | 0 | 0 | 0 | 2 | 1 | 0 | 3 | 1 | 4 | | | | | |
| 35 | 11.2100 | 0 | 4 | 4 | 4 | 4 | 3 | 2 | 4 | 1 | 4 | | | | | |
| 36 | 11.2100 | 0 | 3 | 4 | 4 | 4 | 3 | 2 | 4 | 0 | 4 | | | | | |
| 37 | 11.2100 | 0 | 3 | 4 | 4 | 4 | 3 | 2 | 4 | 0 | 4 | | | | | |
| 38 | 11.2100 | 0 | 3 | 4 | 3 | 4 | 3 | 2 | 4 | 1 | 4 | | | | | |
| 39 | 11.2100 | 0 | 2 | 3 | 3 | 4 | 3 | 2 | 4 | 1 | 4 | | | | | |
| 40 | 11.2100 | 0 | 0 | 0 | 0 | 2 | 1 | 1 | 1 | 0 | 3 | | | | | |
| 41 | 11.2100 | 0 | 1 | 3 | 2 | 4 | 3 | 4 | 4 | 1 | 3 | | | | | |

TABLE B-continued

| Ex. No. | Rate kg/ha | Yens | Anbg | Sejg | Dobr | Bygr | Mogl | Cobu | Vele | Inmu | Wibw | Cath | Colq | Pesw | Rhqg | Rhjg |
|---|---|---|---|---|---|---|---|---|---|---|---|---|---|---|---|---|
| 42 | 11.2100 | 1 | 2 | 1 | 0 | 1 | 1 | 1 | 3 | 1 | 3 | | | | | |
| 43 | 11.2100 | 0 | 0 | 1 | 0 | 0 | 1 | 1 | 3 | 1 | 3 | | | | | |
| 44 | 11.2100 | 0 | 2 | 3 | 3 | 3 | 2 | 1 | 2 | 0 | 2 | | | | | |
| 45 | 11.2100 | 2 | 1 | 3 | 1 | 3 | 3 | 4 | 4 | 0 | 3 | | | | | |
| 46 | 11.2100 | 0 | 4 | 4 | 3 | 4 | 3 | 3 | 4 | 2 | 3 | | | | | |
| 47 | 11.2100 | 0 | 3 | 2 | 1 | 3 | 3 | 2 | 4 | 2 | 4 | | | | | |
| 48 | 11.2100 | 0 | 1 | 3 | 3 | 3 | 3 | 3 | 4 | 0 | 4 | | | | | |
| 49 | 11.2100 | 0 | 1 | 2 | 0 | 3 | 3 | 1 | 4 | 1 | 4 | | | | | |
| 50 | 11.2100 | 0 | 0 | 2 | 0 | 3 | 1 | 1 | 3 | 1 | 3 | | | | | |
| 51 | 11.2100 | 0 | 1 | 2 | 0 | 1 | 2 | 1 | 1 | 0 | 1 | | | | | |
| 52 | 11.2100 | 1 | 0 | 2 | 0 | 2 | 3 | 4 | 4 | 2 | 2 | | | | | |
| 53 | 11.2100 | 0 | 0 | 2 | 1 | 1 | 3 | 1 | 2 | 0 | 3 | | | | | |
| 54 | 11.2100 | 1 | 1 | 3 | 0 | 2 | 3 | 1 | 3 | 0 | 3 | | | | | |
| 55 | 11.2100 | 0 | 0 | 3 | 0 | 3 | 3 | 1 | 3 | 0 | 4 | | | | | |
| 56 | 11.2100 | 0 | 0 | 1 | 0 | 1 | 2 | 1 | 1 | 1 | 3 | | | | | |
| 57 | 11.2100 | 0 | 1 | 1 | 0 | 3 | 3 | 2 | 3 | 1 | 3 | | | | | |
| 58 | 11.2100 | 0 | 0 | 0 | 0 | 0 | 0 | 0 | 0 | 0 | 1 | | | | | |
| 59 | 11.2100 | 0 | 0 | 1 | 0 | 0 | 0 | 0 | 0 | 0 | 2 | | | | | |
| 60 | 11.2100 | 0 | 0 | 2 | 0 | 1 | 3 | 1 | 3 | 2 | 3 | | | | | |
| 61 | 11.2100 | 0 | 1 | 2 | 1 | 1 | 2 | 1 | 2 | 2 | 3 | | | | | |
| 62 | 11.2100 | 0 | 1 | 2 | 0 | 2 | 2 | 1 | 2 | 1 | 3 | | | | | |
| 63 | 11.2100 | 1 | 0 | 0 | 0 | 1 | 0 | 0 | 0 | 0 | 1 | | | | | |
| 64 | 11.2100 | 0 | 3 | 2 | 3 | 3 | 3 | 3 | 4 | 0 | 3 | | | | | |
| 65 | 11.2100 | 0 | 2 | 2 | 1 | 2 | 3 | 2 | 4 | 1 | 4 | | | | | |
| 66 | 11.2100 | 1 | 1 | 2 | 1 | 3 | 2 | 1 | 3 | 1 | 3 | | | | | |
| 67 | 11.2100 | 0 | 0 | 0 | 0 | 1 | 2 | 3 | 3 | 1 | 1 | | | | | |
| 68 | 11.2100 | 1 | 0 | 3 | 0 | 4 | 4 | 4 | 4 | 1 | 3 | | | | | |
| 69 | 11.2100 | 0 | 1 | 3 | 1 | 4 | 3 | 3 | 4 | 0 | 3 | | | | | |
| 70 | 11.2100 | 0 | 3 | 3 | 3 | 4 | 3 | 4 | 4 | 0 | 3 | | | | | |
| 71 | 11.2100 | 1 | 1 | 4 | 1 | 3 | 3 | 3 | 4 | 0 | 2 | | | | | |
| 72 | 11.2100 | 2 | 3 | 4 | 4 | 3 | 3 | 3 | 4 | 1 | 3 | | | | | |
| 73 | 11.2100 | 1 | 3 | 4 | 3 | 3 | 4 | 3 | 4 | 1 | 3 | | | | | |
| 74 | 11.2100 | 2 | 2 | 3 | 1 | 3 | 3 | 4 | 4 | 1 | 4 | | | | | |
| 75 | 11.2100 | 1 | 2 | 3 | 3 | 4 | 3 | 1 | 3 | 1 | 3 | | | | | |
| 76 | 11.2100 | 0 | 1 | 3 | 2 | 3 | 3 | 1 | 2 | 0 | 4 | | | | | |
| 77 | 11.2100 | 0 | 0 | 1 | 0 | 1 | 1 | 1 | 1 | 0 | 1 | | | | | |
| 78 | 11.2100 | 1 | 1 | 3 | 1 | 3 | 3 | — | 4 | 2 | 4 | | | | | |
| 79 | 11.2100 | 1 | 0 | 2 | 1 | 1 | 2 | 1 | 1 | 0 | 3 | | | | | |
| 80 | 11.2100 | 1 | 1 | 2 | 0 | 1 | 1 | 1 | 2 | 0 | 3 | | | | | |
| 81 | 11.2100 | 0 | 0 | 0 | 0 | 0 | 1 | 0 | 1 | 0 | 1 | | | | | |
| 82 | 11.2100 | 0 | | | 0 | 0 | 0 | 0 | 0 | | | 0 | 0 | 0 | 0 | 0 |
| 83 | 11.2100 | 0 | 0 | 1 | 0 | 1 | 3 | 1 | 1 | 0 | 1 | | | | | |
| 84 | 11.2100 | 0 | 0 | 0 | 0 | 1 | 1 | 0 | 0 | 0 | 3 | | | | | |
| 85 | 11.2100 | 0 | 0 | 1 | 0 | 1 | 0 | 0 | 0 | 1 | 3 | | | | | |
| 86 | 11.2100 | 0 | 0 | 1 | 0 | 1 | 1 | 0 | 0 | 0 | 1 | | | | | |

PRE-EMERGENCE ACTIVITY ON WEEDS AND CROPS

In another set of tests, the pre-emergence activity of compounds of this invention was tested on weeds in the presence of crop plants. In these test the following procedure was used.

Topsoil is sieved to pass through a ½ inch (1.27 cm) screen. Fertilizer is added to the topsoil in some of the tests, while in testing other compounds the fertilizer is omitted. The mixture is then sterilized.

The topsoil mixture is placed in an aluminum pan compacted to a depth of about 1.27 cm. from the top of the pan. On the top of the soil is placed a predetermined number of seeds of each of several mono-cotyledonous and dicotyledonous plant species and where noted vegetative propagules of various perennial plant species. The soil required to level fill a pan after seeding or adding vegetative propagules is weighed into another pan. A known amount of the active ingredient is dissolved or suspended in acetone or a suitable organic solvent as a 1% solution or suspension and applied to the cover soil using a sprayer at the desired rate. The spray is thoroughly mixed with this cover soil, and the herbicide/soil mixture is used as a cover layer for the previously prepared pan. Untreated soil is used as a cover layer for control pans. Alternatively, the pans may be covered with the soil layer and the spray solution uniformly applied to the soil surface. When this latter method is used, the statement "surface application" accompanies the test data. In Table C below the amount of active ingredient applied is a kg/ha shown in the Table. The test results are given as percent inhibition of each plant species. After the treatment, the pans are moved to a greenhouse bench. Moisture is supplied to each pan as needed for germination and growth. Growth of each species is observed and corrective measures (greenhouse fumigation, insecticide treatment and the like) are applied as needed.

Approximately 10–14 days (usually 13 days) after seeding and treating, the pans are observed and the results recorded. In some instances, a second observation is made (usually 24–28 days after seeding and treating, although this time interval is at the discretion of the observer), and these observations are indicated in the following tables by a "pound" sign (#) immediately following the Example number.

The pre-emergence data for weeds in the presence of crop plants is shown in the following Table C. In these tests, the plants are identified according to the following column headings:

| | |
|---|---|
| SOBE-Soybean | VELE-Velvetleaf |
| SUBE-Sugarbeet | DOBR-Downy Brome |
| WHEZ-Wheat | PRMI-Proso Millet |
| RICE-Rice | BYGR-Barnyardgrass |
| GRSO-Grain Sorghum | LACG-Large Crabgrass |
| COBU-Cocklebur | GRFT-Green Foxtail |
| WIBW-Wild Buckwheat | CORN-Corn |
| MOGL-Morningglory | COTZ-Cotton |
| HESE-Hemp Sesbanie | RAPE-Oilseed Rape |
| COLQ-Common Lambsquarters | JIWE-Jimsonweed |
| PESW-Pennsylvania Smartweed | COCW-Common Chickweed |

TABLE C

| Ex. No. | Rate kg/ha | Sobe | Cotz | Rape | Cobu | Wibw | Mogl | Hesc | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| 1 | 0.0175 | N | | | 0 | 0 | 0 | 20 | | 0 | 0 | 0 | 0 | 0 | 0 | 0 | 0 | 0 | 0 | 30 | 50 | 35 | |
| | 5.6050 | 70 | 55 | 100 | N | 100 | 90 | 95 | | 100 | 95 | 30 | 90 | 45 | 100 | 100 | 100 | 100 | 100 | 95 | 100 | 100 | |
| | 4.5961 | 90 | 40 | 30 | 75 | 100 | 100 | 100 | 100 | 100 | 100 | 30 | 99 | 99 | 100 | 100 | 100 | 100 | 100 | | | | |
| | 1.1210 | 80 | | | 100 | 100 | 100 | 100 | 100 | 45 | 20 | 55 | 70 | 99 | 100 | 100 | 100 | 100 | 100 | 98 | 100 | 100 | |
| | 1.1210 | 90 | 0 | | 100 | 100 | N | 98 | | 100 | 90 | 10 | 90 | 40 | 100 | 85 | N | 80 | N | 95 | 100 | 100 | |
| | 0.5605 | 40 | | 35 | 100 | 70 | 30 | 30 | | 60 | 0 | 10 | 5 | 30 | 90 | 70 | 80 | 100 | 100 | 99 | 100 | 100 | |
| | 0.2803 | 60 | | | 50 | 100 | 90 | 99 | 75 | 95 | 30 | 5 | 15 | 25 | 55 | 100 | 100 | 100 | 100 | 99 | 100 | 100 | |
| 2 | 5.6050 | 90 | | | 85 | 98 | 85 | 95 | | 98 | 100 | 0 | 95 | 95 | 95 | 70 | 100 | 100 | 99 | 95 | 100 | 100 | |
| | 1.1210 | 85 | | | 60 | 100 | 55 | 95 | | 90 | 85 | 20 | 90 | 65 | 75 | 100 | 100 | 30 | 100 | 70 | 90 | 100 | |
| | 0.5605 | 35 | | | 90 | 35 | 30 | 50 | | 65 | 40 | 10 | 50 | 30 | 80 | 90 | 98 | 60 | 100 | 35 | 90 | 100 | |
| | 0.2803 | 30 | | | 35 | 20 | 10 | 0 | | 35 | 25 | 25 | 35 | 10 | 0 | 85 | 75 | 30 | 100 | 25 | 95 | 90 | |
| | 0.1401 | 20 | | 60 | 80 | N | 0 | 30 | | 25 | 0 | 10 | 30 | 5 | 0 | 80 | 80 | 95 | 80 | 10 | 20 | 95 | |
| | 0.0701 | 30 | 10 | | N | 20 | 90 | 0 | | 0 | 0 | 20 | 0 | 0 | 90 | 0 | 0 | 0 | 0 | 95 | 100 | 95 | |
| | 0.0350 | N | | 0 | 0 | 90 | N | 60 | | 65 | 10 | 0 | 5 | 20 | 70 | 30 | 35 | 65 | 0 | 30 | 30 | 30 | |
| | 0.2803 | 45 | N | | 35 | 0 | 30 | 0 | 20 | 20 | 0 | 0 | 20 | 10 | 0 | 95 | 70 | 50 | 25 | 0 | 50 | 40 | 75 |
| | 0.1401 | 40 | 0 | | 0 | 30 | N | 50 | | 35 | 0 | 35 | 0 | 15 | 0 | 0 | 35 | 20 | 0 | 0 | N | 0 | 50 |
| | 0.0701 | 45 | | | 0 | 0 | 0 | 0 | | 0 | 10 | 0 | 0 | 15 | 0 | 40 | 0 | 0 | 0 | 0 | 0 | 0 | |
| | 0.0701 | 20 | 10 | | 0 | 25 | 0 | 0 | | 35 | 0 | 0 | 0 | 0 | 85 | 30 | 35 | 0 | 95 | 0 | 0 | 40 | |
| | 0.0175 | 0 | N | | N | 0 | N | 0 | 0 | 20 | 0 | 0 | 0 | 0 | 0 | 0 | 0 | 0 | 25 | 0 | 0 | 0 | |
| | 0.0087 | 20 | 0 | | 0 | 30 | 0 | 50 | 0 | 35 | 0 | 30 | 0 | 0 | 0 | 85 | 0 | 85 | 0 | 0 | 0 | 0 | |
| 3 | 5.6050 | 10 | 80 | 95 | 70 | 100 | 95 | 100 | 100 | 100 | 65 | 95 | 90 | 10 | 85 | 85 | 70 | 85 | 95 | 0 | | 0 | |
| | 1.1210 | 15 | 35 | 75 | 85 | 55 | 80 | 90 | 55 | 100 | 0 | 50 | 0 | 15 | 0 | 0 | 0 | 0 | 25 | 0 | | | |
| | 0.2803 | 0 | 10 | 45 | 55 | 40 | 70 | 95 | 25 | 75 | 0 | 15 | 0 | 15 | 0 | 0 | 0 | 0 | 0 | 0 | | | |
| | 0.0701 | 0 | 0 | 0 | 0 | 0 | 0 | 70 | 0 | 45 | 0 | 50 | 0 | 0 | 10 | 65 | 20 | 95 | 60 | 0 | | | |
| | 0.0175 | 65 | 10 | 30 | 10 | 70 | 0 | 0 | 20 | 0 | 0 | 35 | 5 | 30 | 0 | 30 | 0 | 65 | 5 | 0 | | | |
| 4 | 5.6050 | 0 | 25 | 0 | 25 | 50 | 0 | 55 | 55 | 100 | 0 | 15 | 0 | 25 | 9 | 30 | 0 | 40 | 30 | 0 | 0 | 0 | |
| | 1.1210 | 0 | 0 | 40 | 0 | 100 | 95 | 90 | 25 | 20 | 0 | 50 | 55 | 70 | 80 | 30 | 20 | 100 | 100 | 0 | 35 | 0 | |
| 5 | 5.6050 | 90 | 25 | 30 | 25 | 98 | 80 | 95 | 20 | 40 | 45 | 20 | 35 | 80 | 35 | 25 | 65 | 75 | 90 | 0 | 35 | 0 | |
| | 1.1210 | 30 | 0 | 30 | 0 | 50 | 0 | 40 | 0 | 100 | 40 | 25 | 20 | 20 | 15 | N | Z | N | 0 | 0 | 0 | 0 | 0 |
| | 0.2803 | 40 | 0 | 0 | 0 | 60 | 0 | 0 | | 80 | 0 | 0 | 0 | 10 | 0 | 0 | 0 | Z | 0 | 0 | N | 0 | 0 |
| | 0.0701 | 0 | 0 | 0 | Z | N | 0 | Z | | 0 | 0 | 25 | 0 | 25 | 9 | 0 | 0 | N | 0 | 0 | 0 | 0 | 0 |
| | 0.0175 | 0 | 0 | | N | 40 | 0 | N | | N | 0 | N | 0 | 0 | N | Z | 0 | Z | 0 | 0 | 0 | 0 | 0 |
| | 0.0087 | 10 | Z | | Z | 80 | 0 | 90 | | 40 | 0 | 35 | 0 | 30 | 25 | 0 | 0 | 100 | 100 | 0 | 0 | 0 | 0 |
| 7 | 5.6050 | 80 | N | | 25 | 100 | 95 | 100 | | 95 | 95 | 35 | 95 | 70 | 90 | 100 | 95 | 100 | 100 | 100 | 60 | 100 | |
| | 5.6050 | 25 | | | 0 | 0 | 90 | 0 | | 100 | 35 | 15 | 35 | 75 | 70 | 90 | 80 | 100 | 90 | 100 | 100 | 99 | |
| | 1.1210 | 10 | | | 0 | 25 | 60 | 40 | | 60 | 15 | 40 | 40 | 25 | 50 | 90 | 90 | 40 | 20 | 90 | 0 | 98 | |
| | 1.1210 | 10 | | | 0 | 0 | 60 | 60 | | 80 | 70 | 0 | 75 | 10 | 15 | 90 | 90 | 0 | 95 | 80 | 35 | 100 | |
| | 0.5605 | 0 | | | 0 | 25 | 100 | 0 | | 10 | 35 | 0 | 35 | 25 | 35 | 85 | 20 | 20 | 95 | 85 | 0 | 95 | |
| | 0.5605 | 0 | | | 0 | 0 | 90 | 25 | | 80 | 0 | 0 | 0 | 5 | 25 | 30 | 0 | 0 | 80 | 35 | N | 85 | |
| | 0.2803 | 0 | | | Z | 0 | 80 | 35 | | 0 | 20 | 20 | 35 | 0 | 0 | 70 | 0 | 0 | 0 | 0 | 0 | 50 | |
| | 0.2803 | 10 | | | Z | 0 | 30 | 20 | | 15 | 0 | 0 | 10 | 0 | 0 | 70 | 0 | 0 | 0 | 0 | 0 | 30 | |
| | 0.2803 | 0 | | | N | 0 | 60 | 0 | | 0 | 0 | 0 | 5 | 0 | 50 | 90 | 0 | 30 | 0 | 70 | 0 | 100 | |
| | 0.1401 | 0 | Z | | Z | 0 | 20 | 0 | | 15 | 10 | 20 | 20 | 0 | 0 | 25 | 0 | 0 | 0 | 0 | 0 | 10 | |
| | 0.1401 | N | Z | | 0 | 25 | 40 | 0 | | 0 | 0 | 0 | 0 | 0 | 0 | 0 | 0 | 0 | 0 | 0 | 0 | 70 | |
| | 0.1401 | 0 | | | 0 | 0 | 20 | 0 | | 20 | 0 | 15 | 0 | 0 | 0 | 0 | 0 | 0 | Z | 0 | 0 | 80 | |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
|  | 0.0701 | 0 |  |  | 0 | N | N | N |  | 20 | 0 | 0 | 0 | 0 | 0 | 15 | 0 | 0 | 0 | 10 | 0 | 50 |  |
|  | 0.0701 | 0 |  |  | 0 | 0 | N | 0 |  | 0 | 5 | N | 0 | 0 | 0 | 0 | 0 | 0 | 0 | 0 | 0 | 0 |  |
|  | 0.0701 | N |  |  | 0 | 0 | 0 | 0 |  | N | 0 | 0 | 0 | 10 | 0 | 0 | 0 | 0 | 0 | 40 | 0 | 25 |  |
|  | 0.0350 | 0 |  |  | N | 25 | 0 | 20 |  | 15 | 0 | 0 | 0 | 0 | 0 | 0 | 0 | 0 | 0 | 0 | 0 | 50 |  |
|  | 0.0350 | 0 |  |  | 0 | 0 | N | 0 |  | 0 | 0 | 0 | 0 | 0 | 0 | 0 | 0 | 0 | 0 | 30 | 25 | 80 |  |
|  | 0.0175 | 0 |  |  | 0 | 0 | 0 | 0 |  | 0 | 0 | 0 | 0 | 0 | 0 | 0 | 0 | 0 | 0 | 0 | 0 | 0 |  |
|  | 0.0175 | 20 |  |  | N | 0 | N | 0 |  | 0 | 0 | 0 | 0 | 0 | 0 | 0 | 0 | 0 | 0 | 0 | 0 | 0 |  |
|  | 0.0175 | 5 |  |  | 0 | 0 | N | 0 |  | 0 | 0 | 0 | 0 | 0 | 0 | 0 | 0 | 0 | 0 | 0 | 0 | 0 |  |
|  | 0.0087 | 0 |  |  | N | 0 | 0 | 0 |  | 0 | 0 | 0 | 0 | 0 | 0 | 0 | 0 | 0 | 0 | 0 | 0 | 0 |  |
|  | 0.0087 | 15 |  |  | 0 | 0 | 0 | 25 |  | 30 | 0 | 25 | 20 | 15 | 0 | 20 | 0 | 0 | 0 | 30 | 0 | 75 |  |
| 8 | 5.6050 | 40 | 60 | 100 | 95 | 100 | 95 | 100 |  | 100 | 55 | 80 | 98 | 40 | N | 75 | 95 | 70 | 100 |  |  |  | 90 |
|  | 1.1210 | 45 | 25 | 100 | 90 | 90 | 85 | 100 |  | 100 | 0 | 25 | 85 | 0 | 80 | 0 | 70 | 0 | 85 |  |  |  | 20 |
|  | 0.2803 | 45 | 15 | 80 | 0 | 60 | 60 | 95 |  | 95 | 0 | 20 | 0 | 0 | 40 | 0 | 0 | 0 | 25 |  |  |  | 0 |
|  | 0.0701 | 0 | 0 | 25 | 0 | 35 | 30 | 90 |  | 40 | 0 | 0 | 0 | 10 | 0 | 0 | 0 | 0 | 0 |  |  |  | 20 |
|  | 0.0175 | N | 0 | 35 | N | 30 | 0 | 80 |  | 0 | 0 | 0 | 0 | 0 | 0 | 0 | 0 | 0 | 0 |  |  |  | 0 |
|  | 0.0087 | 0 | 0 | 0 | 0 | 0 | 0 | 45 |  | 20 | 0 | 0 | 0 | 0 | 0 | 0 | 0 | 0 | 0 |  |  |  | 0 |
| 10 | 5.6050 | 40 | 50 | 100 | 50 | 100 | 90 | 100 |  | 100 | 85 | 70 | 95 | 85 | 100 | 100 | 100 | 100 | 100 |  |  |  | 90 |
|  | 1.1210 | 30 | 35 | 90 | 25 | 90 | 50 | 70 |  | 90 | 25 | 25 | 85 | 20 | 95 | 90 | 90 | 95 | 95 |  |  |  | 45 |
|  | 0.2803 | 0 | 20 | 0 | 0 | 100 | 0 | 0 |  | 50 | 20 | 40 | 60 | 0 | 70 | 60 | 40 | 85 | 70 |  |  |  | 30 |
|  | 0.0701 | 0 | 0 | 30 | 0 | 50 | 0 | N |  | 25 | 0 | 15 | 60 | 15 | 40 | 10 | 0 | 30 | 40 |  |  |  | 45 |
|  | 0.0175 | 0 | 0 | 0 | 0 | 0 | 0 | 0 |  | 0 | 0 | 25 | 0 | 0 | 0 | 0 | 0 | 0 | 0 |  |  |  | 0 |
|  | 0.0087 | 30 | 35 | 15 | 0 | 60 | 35 | 65 |  | 60 | 0 | 25 | 45 | 40 | 35 | 45 | 30 | 95 | 70 |  |  |  | 30 |
| 11 | 5.6050 | 15 | 40 | 30 | 0 | 70 | 40 | 50 |  | 25 | 0 | 70 | 40 | 0 | 0 | 0 | 0 | 85 | 0 |  |  |  | N |
|  | 1.1210 | 30 | 20 | 35 | 0 | 60 | 0 | 25 |  | 25 | 0 | 0 | 0 | 20 | 0 | 0 | 30 | 30 | 70 |  |  |  | 40 |
| 12 | 5.6050 | 90 | 60 | 100 | 90 | 100 | 100 | 100 |  | 100 | 90 | 95 | 100 | 100 | 100 | 100 | 100 | 100 | 100 |  |  |  | 95 |
|  | 1.1210 | 35 | 35 | 70 | 65 | 100 | 90 | 95 |  | 90 | 40 | 90 | 90 | 90 | 100 | 95 | 95 | 100 | 100 |  |  |  | 10 |
|  | 0.2803 | 10 | 25 | 35 | 0 | 100 | 75 | 90 |  | 90 | 10 | 90 | 75 | 55 | 90 | 90 | 40 | 85 | 90 |  |  |  | 0 |
|  | 0.0701 | 0 | 20 | 0 | 0 | 15 | 0 | 60 |  | 0 | 0 | 40 | 45 | 30 | 30 | 35 | 15 | 20 | 40 |  |  |  | 0 |
|  | 0.0175 | 5 | 0 | 0 | 0 | 0 | 0 | 0 |  | 0 | 0 | N | 15 | 5 | 20 | 30 | 0 | 0 | 0 |  |  |  | 0 |
| 15 | 5.6050 | 95 | 90 | 100 | 90 | 100 | 100 | 100 |  | 100 | 95 | 80 | 95 | 90 | 100 | 100 | 100 | 100 | 100 |  |  | 0 | 100 |
|  | 1.1210 | 55 | 55 | 95 | 80 | 100 | 100 | 98 |  | 100 | 75 | 75 | 95 | 30 | 95 | 100 | 100 | 100 | 100 |  |  |  | 90 |
|  | 0.2803 | 45 | 30 | 25 | 0 | 75 | 65 | 75 |  | 80 | 15 | 30 | 40 | 10 | 70 | 70 | 90 | 100 | 80 |  |  |  | 0 |
|  | 0.0701 | 20 | 50 | 25 | 0 | 0 | 55 | 25 |  | 25 | 5 | 5 | 5 | 0 | 10 | 10 | 25 | 0 | 30 |  |  |  | 0 |
|  | 0.0175 | 25 | 60 | 25 | 0 | 0 | 30 | N |  | N | 5 | 0 | 5 | 5 | 0 | 10 | 0 | 25 | 20 |  |  |  | 0 |
| 16 | 5.6050 | 95 | 65 | 95 | 55 | 100 | 100 | 100 |  | 100 | 60 | 95 | 98 | 90 | 95 | 100 | 98 | 100 | 100 |  |  |  | 100 |
|  | 1.1210 | 70 | 70 | 99 | 45 | 100 | 100 | 98 | 100 | 100 | 25 | 85 | 90 | 50 | 35 | 95 | 95 | 95 | 95 |  |  |  | 90 |
|  | 0.2803 | 30 | 20 | 70 | 0 | 70 | 75 | 55 | 90 | 95 | 0 | 10 | 45 | 30 | 0 | 75 | 55 | 55 | 10 |  |  |  | 0 |
|  | 0.0701 | 0 | 20 | 10 | 0 | 20 | 40 | 50 | 25 | 45 | 0 | 0 | 15 | 5 | 0 | 40 | 10 | 10 | 20 |  |  |  | 0 |
|  | 0.0175 | 20 | 30 | 20 | 0 | 15 | 20 | N | 0 | 5 | 0 | 0 | 0 | 10 | 0 | 15 | 0 | 20 | 10 |  |  | 0 | 0 |
| 18 | 5.6050 | 70 | 15 | 0 | 45 | 100 | 95 | 100 | 0 | 100 | 90 | 80 | 50 | 90 | 100 | 100 | 100 | 100 | 100 |  |  |  | 90 |
|  | 1.1210 | 10 | 65 | 90 | 0 | 95 | 45 | 99 | 0 | 100 | 60 | 0 | 15 | 30 | 75 | 75 | 95 | 35 | 80 |  |  |  | 40 |
|  | 0.2803 | N | 10 | 30 | 0 | 100 | 20 | 0 | 0 | 20 | 30 | 0 | 0 | 25 | 0 | 10 | 55 | 0 | 10 |  |  |  | 0 |
|  | 0.0701 | 40 | 0 | 0 | 0 | 0 | 0 | 0 | 0 | 0 | 0 | N | 0 | 0 | 0 | 0 | 10 | 0 | 0 |  |  |  | 0 |
|  | 0.0175 | 0 | 0 | 0 | 0 | 0 | 0 | 0 | 0 | 0 | 0 | 0 | 0 | 0 | 0 | 0 | 0 | 0 | 0 |  |  |  | 0 |
|  | 0.0087 | N | 0 | 0 | 0 | 0 | 0 | 0 | 0 | 0 | 0 | 0 | 0 | 0 | 0 | 0 | 0 | 0 | 0 |  |  |  | 0 |
| 19 | 5.6050 | 60 | 40 | 95 | 90 | 100 | 100 | 100 | 100 | 100 | 85 | 65 | 90 | 70 | 100 | 100 | 100 | 100 | 100 |  |  |  | 0 |
|  | 1.1210 | 90 | 0 | 65 | 40 | 100 | 85 | 100 | 95 | 100 | 35 | 55 | 80 | 30 | 75 | 100 | 100 | 100 | 100 |  |  |  | 0 |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| 20 | 0.2803 | 10 | N | 20 | 0 | 90 | 30 | 90 | 45 | 40 | 35 | 0 | 45 | 45 | 55 | 60 | 55 | 95 | 95 | | | | |
| | 0.0701 | 20 | 0 | 0 | 0 | 30 | 0 | 0 | 0 | 0 | 0 | 0 | 10 | 10 | 0 | 0 | 0 | 60 | 30 | | | | |
| | 0.0175 | 15 | 10 | N | N | 0 | 0 | 0 | 0 | 0 | 0 | 30 | 90 | 0 | 70 | 95 | 100 | 90 | 100 | | | | |
| | 5.6050 | 75 | 65 | 100 | 100 | 85 | 100 | 100 | 100 | 100 | 90 | 80 | 15 | 45 | 20 | 100 | 85 | 30 | 100 | | | 30 | |
| | 1.1210 | 50 | 30 | 95 | 90 | 80 | 100 | 85 | 95 | 100 | 20 | 70 | 0 | 25 | 0 | 80 | 45 | 0 | 60 | | | 10 | |
| | 0.2803 | 30 | 40 | 90 | 70 | 20 | 40 | 100 | 85 | 90 | 25 | 50 | 0 | 0 | 0 | 90 | 0 | 0 | 0 | | | | |
| | 0.0701 | 20 | 15 | 0 | 0 | 0 | 0 | 40 | 0 | 70 | 10 | 20 | 0 | 0 | 0 | 70 | 0 | 0 | 0 | | 50 | | |
| | 0.0175 | 0 | 10 | 0 | 0 | 0 | 0 | 0 | 0 | 0 | 0 | 0 | 0 | 0 | 0 | 0 | 0 | 0 | 0 | | | | |
| | 0.0087 | 0 | 0 | | | 0 | 0 | 0 | | 0 | 0 | 0 | 0 | 0 | 0 | 0 | 0 | 0 | 0 | | | | |
| 21 | 5.6050 | 55 | 20 | 35 | 20 | 95 | 100 | 100 | | 100 | 85 | 40 | 85 | 90 | 95 | 100 | 100 | 100 | 100 | 98 | 100 | 100 | 100 |
| | 5.6050 | 45 | 0 | 0 | 10 | 100 | 95 | 100 | | 100 | 95 | 30 | 90 | 95 | 100 | 100 | 99 | 75 | 99 | | | | |
| | 1.1210 | 5 | | | 0 | 95 | 70 | 20 | | 60 | 20 | 0 | 35 | 60 | 75 | 75 | 30 | 65 | 50 | 90 | 25 | 98 | |
| | 1.1210 | 0 | 0 | | N | 40 | 95 | 80 | | 40 | 25 | 0 | 85 | 40 | 65 | 95 | 90 | 80 | 85 | 20 | 30 | 80 | 50 |
| | 0.5605 | 0 | 0 | | Z | 25 | 35 | 30 | | 30 | 10 | 0 | 30 | 20 | 30 | 85 | 25 | 40 | 75 | 0 | 0 | 85 | 100 |
| | 0.2803 | 0 | 0 | 0 | 10 | 20 | 90 | 30 | | 30 | 0 | 0 | 50 | 10 | 50 | 80 | 0 | 60 | 60 | 0 | 35 | | 85 |
| | 0.1401 | 0 | 15 | | 15 | 0 | 50 | 10 | | 45 | 5 | 0 | 0 | 0 | 0 | 35 | 0 | 10 | 0 | 0 | 0 | 90 | 0 |
| | 0.0701 | 0 | 35 | | 35 | 0 | 10 | 0 | | 0 | 0 | 0 | 15 | 20 | 0 | 20 | 0 | 0 | 0 | 0 | 0 | 0 | 0 |
| 22 | 5.6050 | 0 | 0 | 100 | 70 | 100 | 100 | 100 | | 100 | 25 | 0 | 90 | 45 | 10 | 40 | 90 | 90 | 100 | 98 | 100 | | |
| | 1.1210 | 85 | 50 | 90 | 10 | 95 | 95 | 95 | | 100 | 15 | 35 | 70 | 25 | 25 | 0 | 75 | 95 | 75 | 90 | 100 | | |
| | 0.2803 | 20 | 0 | 50 | 0 | 25 | 35 | 30 | | 45 | 20 | 70 | 0 | 0 | 0 | 0 | 35 | 25 | 0 | 20 | 100 | N | |
| | 0.0701 | 25 | 15 | 0 | 0 | 0 | 30 | 25 | | 20 | 0 | 0 | 0 | 0 | 0 | 0 | 25 | 30 | 0 | 0 | 100 | N | |
| 24 | 5.6050 | 10 | | | 0 | 100 | 90 | 95 | | 98 | 90 | 0 | 90 | 40 | 100 | 100 | 100 | 100 | 100 | 0 | 100 | N | |
| | 1.1210 | 10 | | | 90 | 95 | 65 | 100 | | 90 | 85 | 10 | 90 | 65 | 98 | 95 | 90 | 100 | 98 | 0 | 100 | N | |
| | 0.5605 | 0 | | | N | 99 | 30 | 85 | | 30 | 10 | 10 | 35 | 20 | 100 | 90 | 55 | 100 | 90 | 55 | 100 | N | |
| | 0.2803 | 0 | | | 0 | 20 | 30 | 55 | | 35 | 60 | 10 | 15 | 20 | 98 | 90 | 85 | 100 | 90 | 40 | 100 | N | |
| | 0.1401 | 0 | | | 0 | 35 | 60 | 80 | | 25 | 0 | 0 | 35 | 15 | 70 | 55 | 30 | 30 | 25 | 90 | 85 | N | 90 |
| | 0.1401 | 0 | 35 | | 35 | 35 | 0 | 30 | | 0 | 35 | 0 | 0 | 0 | 35 | 30 | 20 | 45 | 0 | 0 | 90 | N | 0 |
| | 0.0701 | N | Z | | N | Z | Z | 40 | | 25 | 0 | Z | 0 | 0 | 0 | 0 | 0 | 60 | 0 | 30 | 0 | N | 0 |
| | 0.0701 | 30 | 0 | 0 | 0 | 0 | 70 | 0 | | 0 | 0 | 0 | 0 | 0 | 0 | 0 | 0 | 20 | 0 | 35 | 30 | N | 0 |
| 25 | 5.6050 | N | 30 | 60 | 35 | 0 | 50 | 75 | | 100 | 90 | 70 | 90 | 20 | 100 | 100 | 100 | 100 | 100 | 0 | 50 | N | 90 |
| | 1.1210 | 50 | 10 | 0 | 0 | 25 | 95 | 0 | | 65 | 45 | 40 | 55 | 35 | 90 | 75 | 90 | 75 | 95 | 35 | 0 | Z | 0 |
| | 0.2803 | 50 | 10 | 20 | 0 | 0 | 0 | 0 | | 0 | 0 | 70 | 40 | 20 | 30 | 60 | 55 | 20 | 70 | 0 | 0 | Z | 0 |
| | 0.0701 | 0 | Z | 0 | 0 | 0 | 40 | 0 | | 0 | 0 | Z | 15 | 0 | 0 | 45 | 10 | 0 | 25 | 0 | 30 | Z | 0 |
| | 0.0175 | 0 | 0 | 100 | 0 | 25 | 15 | 0 | | 25 | 0 | 35 | 0 | 30 | 0 | 0 | 20 | 0 | 0 | 30 | 0 | Z | 0 |
| 26 | 5.6050 | 90 | 55 | 75 | 75 | 99 | 100 | 100 | 10 | 100 | 0 | 90 | 95 | 90 | 98 | 100 | 100 | 100 | 100 | 35 | 100 | Z | 99 |
| | 1.1210 | 60 | 30 | 60 | 60 | 0 | 95 | 25 | 10 | 40 | 40 | 25 | 50 | 70 | 60 | 65 | 90 | 75 | 95 | 0 | 85 | Z | 70 |
| | 0.2803 | 15 | 15 | 20 | 0 | 0 | 65 | N | 0 | 25 | 45 | Z | 25 | 15 | 35 | 15 | 70 | 10 | 75 | 35 | 90 | Z | 5 |
| | 0.0701 | 5 | 30 | 0 | 0 | 25 | 35 | 15 | 0 | 25 | 20 | 25 | 25 | 15 | 15 | 45 | 10 | 95 | 60 | 0 | 0 | Z | 0 |
| 27 | 5.6050 | 20 | 0 | 15 | 0 | 0 | 15 | 0 | 0 | 40 | 15 | 5 | 0 | 5 | 20 | 35 | 0 | 10 | 0 | 65 | 30 | Z | 0 |
| | 1.1210 | 0 | 5 | 0 | 0 | 0 | 0 | 0 | 0 | 25 | 0 | 10 | 5 | 10 | 65 | 10 | 20 | 75 | 0 | 0 | 0 | Z | 0 |
| | 0.2803 | 0 | 0 | 0 | 0 | 0 | 0 | 0 | 0 | 25 | 0 | 15 | 0 | 5 | 15 | 45 | 0 | 20 | 0 | 0 | 50 | | |
| | 0.0701 | 0 | 0 | 0 | 0 | 0 | 0 | 0 | 0 | 0 | 0 | N | 0 | 0 | 0 | 0 | 0 | 0 | 0 | 0 | | | |
| | 0.0175 | 0 | 0 | 0 | 0 | 0 | 0 | 0 | 0 | 0 | 0 | 0 | 0 | 0 | 0 | 0 | 0 | 0 | 0 | 0 | | | |
| 28 | 5.6050 | 95 | | | 20 | 100 | 90 | 100 | | 100 | 70 | 90 | 100 | 85 | 90 | 100 | 100 | 100 | 100 | 100 | 100 | 100 | |
| | 1.1210 | 10 | | | 0 | 100 | 80 | 95 | | 100 | 0 | 30 | 50 | 0 | 90 | 80 | 100 | 80 | 99 | 100 | 100 | 100 | |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
|  | 0.5605 | N | | | 0 | 70 | 50 | 60 | | 70 | 0 | 20 | 40 | 0 | 0 | 100 | 100 | 20 | 100 | 99 | 100 | 100 | |
|  | 0.2803 | 0 | | | 0 | N | 10 | 0 | | 40 | 0 | 30 | 10 | 0 | 0 | 95 | 30 | 0 | 40 | 70 | 90 | 100 | |
|  | 0.1401 | 0 | | | 0 | 30 | 0 | 10 | | 0 | 0 | 0 | 0 | 0 | 0 | 50 | 0 | 0 | 0 | 75 | 80 | 100 | |
|  | 0.0701 | 0 | | | 0 | N | 0 | 0 | | 0 | 0 | 0 | 0 | 0 | 0 | 0 | 0 | 0 | 0 | 50 | 70 | 80 | |
|  | 0.0350 | 0 | | | 0 | N | 0 | 0 | | 0 | 0 | 0 | 0 | 0 | 0 | 0 | 0 | 0 | 0 | 0 | 60 | 50 | |
| 29 | 5.6050 | 80 | 50 | 100 | 0 | 100 | 100 | 100 | 100 | 100 | 55 | 25 | 90 | 95 | 85 | 100 | 100 | 100 | 95 | | | | 90 |
|  | 1.1210 | 40 | 0 | 80 | 30 | 100 | 80 | 98 | 80 | 100 | 0 | 0 | 20 | 40 | 0 | 0 | 70 | 0 | 80 | | | | 10 |
|  | 0.2803 | 40 | 0 | 50 | 0 | 80 | 0 | 70 | 0 | 90 | 25 | 0 | 0 | 20 | N | 0 | 0 | 0 | 20 | | | | 45 |
|  | 0.0701 | 0 | N | 30 | 35 | 25 | 0 | 0 | 0 | 0 | 0 | 15 | 0 | 10 | 40 | 30 | 0 | 0 | 30 | | | | 40 |
|  | 0.0175 | 0 | 0 | 40 | 0 | 35 | 0 | 0 | 0 | 0 | 0 | 25 | 0 | 5 | 0 | N | 0 | 0 | 0 | | | | 0 |
|  | 0.0087 | 0 | 0 | 0 | 0 | 0 | 0 | 0 | | 0 | 0 | 15 | 0 | 0 | 0 | 0 | 0 | 0 | 0 | | | | |
| 30 | 5.6050 | 60 | 30 | 35 | 10 | 100 | 95 | 85 | | 90 | 40 | 20 | 75 | 70 | 85 | 30 | 100 | 20 | 100 | | | | 100 |
|  | 1.1210 | 35 | 10 | 40 | 30 | 100 | 80 | 30 | | 30 | 15 | 10 | 25 | 25 | 40 | N | 70 | 100 | 90 | | | | 70 |
|  | 0.2803 | 0 | 45 | 30 | 0 | 100 | 10 | 35 | | N | 30 | 25 | 15 | 20 | 0 | 40 | 30 | 95 | 20 | | | | 0 |
|  | 0.0701 | 20 | N | 0 | 15 | 40 | 30 | 10 | | 15 | 0 | 0 | 0 | 10 | 0 | 15 | 0 | 60 | 15 | | | | 10 |
|  | 0.0175 | 10 | 25 | 0 | N | 0 | 30 | 0 | | 0 | 0 | 25 | 15 | 0 | 0 | 20 | 0 | 0 | 0 | | | | 0 |
| 34 | 5.6050 | 95 | 95 | 85 | N | 100 | 100 | 100 | 10 | 100 | 65 | 95 | 95 | 100 | 100 | 100 | 100 | 100 | 100 | | | | 100 |
|  | 1.1210 | 90 | 25 | 60 | N | 100 | 95 | 100 | 100 | 100 | 75 | 90 | 90 | 95 | 85 | 100 | 98 | 90 | 95 | | | | 100 |
|  | 0.2803 | 40 | 10 | 0 | N | 100 | 85 | 90 | 90 | 85 | 30 | 80 | 30 | 65 | 25 | 0 | 80 | 30 | 50 | | | | 65 |
|  | 0.0701 | 10 | 0 | 20 | Z | 60 | 85 | 0 | 0 | 25 | 0 | 0 | 10 | 20 | 0 | 0 | 10 | 0 | 0 | | | | 0 |
|  | 0.0175 | 0 | 0 | 0 | N | 40 | 0 | 0 | 25 | 0 | 0 | 10 | 0 | 0 | 0 | 0 | 10 | 10 | 0 | | | | 0 |
|  | 0.0087 | N | 15 | N | N | 45 | N | 0 | | 0 | 0 | N | N | N | 0 | 0 | 0 | 0 | 0 | | | | 100 |
| 35 | 5.6050 | 75 | 65 | 70 | 90 | 100 | 100 | 100 | | 100 | 55 | 70 | 90 | 85 | 100 | 100 | 100 | 100 | 100 | | | | 100 |
|  | 1.1210 | 10 | 15 | 40 | 70 | 100 | 95 | 90 | | 55 | 25 | 40 | 55 | 45 | 40 | 95 | 95 | 90 | 100 | | | | 65 |
|  | 0.2803 | 10 | 0 | 0 | 0 | 80 | 30 | 65 | | 30 | 0 | 0 | 25 | 20 | 0 | 35 | 30 | 65 | 75 | | | | 0 |
|  | 0.0701 | 30 | 25 | 0 | 0 | 0 | 0 | 0 | | 0 | 0 | 10 | 0 | 20 | 0 | 5 | 0 | 0 | 5 | | | | 0 |
|  | 0.0175 | 10 | 25 | 0 | 15 | 0 | 30 | 0 | | 15 | 0 | 30 | 15 | 0 | 0 | 0 | 0 | 0 | 90 | | | | 100 |
| 36 | 5.6050 | 65 | 60 | 55 | 65 | 98 | 100 | 98 | | 100 | 80 | 65 | 45 | 45 | 85 | 60 | 90 | 100 | 100 | | | | 70 |
|  | 1.1210 | 15 | 15 | 10 | 35 | 75 | 30 | 65 | | 20 | 20 | 45 | 40 | 55 | 40 | 30 | 60 | 75 | 90 | | | | 0 |
|  | 0.2803 | 25 | 0 | 0 | 0 | 0 | 0 | 0 | | 0 | 0 | 10 | 0 | 10 | 0 | 0 | 0 | 20 | 15 | | | | 10 |
|  | 0.0701 | 35 | N | 20 | 0 | 25 | 30 | 30 | | 15 | 20 | 10 | 0 | 20 | 30 | 0 | 0 | 20 | 0 | | | | 0 |
|  | 0.0175 | 0 | 0 | 0 | 0 | 0 | 0 | 0 | | 0 | 0 | 0 | 0 | 0 | 0 | 0 | 0 | 0 | 0 | | | | 0 |
| 37 | 5.6050 | 65 | 55 | 20 | 70 | 100 | 100 | 95 | | 100 | 30 | 60 | 70 | 60 | 90 | 95 | 100 | 100 | 100 | | | | 100 |
|  | 1.1210 | 30 | 0 | 20 | 55 | 50 | 90 | 80 | | 40 | 10 | 15 | 35 | 40 | 25 | 40 | 55 | 90 | 95 | | | | 30 |
|  | 0.2803 | 15 | 0 | 15 | 0 | 0 | 30 | 0 | | 0 | 0 | 25 | 30 | 25 | 0 | 10 | 10 | 40 | 0 | | | | 80 |
|  | 0.0701 | 30 | Z | N | 0 | 100 | 0 | N | | 0 | 0 | 55 | 0 | 20 | N | 10 | 0 | 30 | 15 | | | | 40 |
|  | 0.0175 | 0 | 0 | 0 | 0 | 0 | 0 | 0 | | 0 | 0 | 20 | 0 | 20 | 0 | 60 | 0 | 0 | 0 | | | | 0 |
| 38 | 5.6050 | 60 | 0 | 0 | 50 | 100 | 100 | 100 | | 100 | 60 | 85 | 70 | 50 | 98 | 100 | 95 | 100 | 100 | | | | 100 |
|  | 1.1210 | 20 | 0 | 55 | 0 | 95 | 90 | 45 | | 25 | 30 | 20 | 25 | 20 | 50 | 100 | 55 | 100 | 75 | | | | 95 |
|  | 0.2803 | 0 | Z | 10 | 0 | 0 | 0 | 0 | | 0 | 0 | 55 | 25 | 35 | 0 | 40 | 15 | 40 | 40 | | | | 30 |
|  | 0.0701 | N | 0 | 0 | 0 | 0 | 0 | 0 | | 0 | 0 | 20 | 0 | 65 | 0 | 10 | 0 | 100 | 15 | | | | 80 |
| 39 | 5.6050 | 70 | 80 | 95 | 75 | 100 | 100 | 100 | | 100 | 90 | 85 | 85 | 90 | 100 | 100 | 100 | 100 | 100 | | | | 40 |
|  | 1.1210 | 30 | 80 | 75 | 55 | 100 | 90 | 100 | | 35 | 80 | 95 | 70 | 80 | 100 | 100 | 99 | 100 | 80 | | | | 0 |
|  | 0.2803 | 20 | 75 | 50 | 0 | 100 | 50 | 70 | | 0 | 10 | N | 35 | 65 | 35 | 40 | 65 | 90 | 70 | | | | 100 |
|  | 0.0701 | 0 | 40 | 55 | 60 | 90 | 0 | 95 | | 15 | 20 | 25 | 0 | 20 | N | 50 | 10 | 55 | 0 | | | | 30 |
| 0.0175 | N | 0 | N | 0 | 0 | 20 | 0 | 0 | N | 0 | 35 | 0 | 0 | 10 | 0 | 20 | 35 | 0 | 0 | | N | | 0 |
| 40 | 0.0087 | 0 | 0 | 35 | 25 | 95 | 65 | 0 | | 95 | 0 | 80 | 5 | 0 | 85 | 75 | 0 | 95 | 0 | | | | 95 |
|  | 5.6050 | 70 | 85 | 75 | 0 | 0 | Z | 0 | | 0 | 35 | N | 0 | 10 | N | 0 | 25 | 25 | 70 | | | | N |
|  | 0.2803 | 35 | 30 | 35 | 90 | N | 0 | 100 | | 100 | 0 | 80 | 5 | N | 70 | 100 | 10 | 75 | 25 | | | | 70 |
| 41 | 5.6050 | 95 | 95 | 100 | 90 | 95 | 100 | 100 | | 100 | 25 | 55 | 95 | 65 | 70 | 100 | 90 | 100 | 100 | | | | 90 |
|  | 1.1210 | 20 | 50 | 90 | 10 | 100 | 95 | 100 | | 100 | 35 | 45 | 40 | 5 | 30 | 65 | 75 | 90 | 90 | | | | |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
|  | 0.2803 | 15 | N | 45 | 40 | 95 | 40 | 100 |  | 90 | 40 | N | 0 | 20 | N | 45 | 0 | 75 | 10 |  |  |  | 85 |
|  | 0.0701 | 35 | 35 | 35 | 0 | 85 | N | 70 |  | 45 | 0 | 60 | 0 | 20 | N | 55 | 0 | 25 | 40 |  |  |  | 60 |
|  | 0.0175 | 25 | 30 | N | 0 | 40 | 60 | 0 |  | 0 | 0 | N | 10 | 0 | 0 | 0 | 40 | 0 | 40 |  |  |  | 0 |
|  | 0.0087 | N | N | 35 | 0 | N | 45 | 25 |  | N | 0 | N | 0 | 0 | 30 | 0 | 0 | 25 | 35 |  |  |  | N |
| 42 | 5.6050 | 90 | 35 | 100 | 30 | 100 | 90 | 90 |  | 100 | 95 | 50 | 100 | 90 | 100 | 100 | 100 | 100 | 100 |  |  |  | 30 |
|  | 1.1210 | 90 | 20 | 95 | 30 | 100 | 90 | 95 |  | 100 | 40 | 15 | 35 | 25 | 35 | 60 | 25 | 85 | 95 |  |  |  | 0 |
|  | 0.2803 | 80 | 0 | 65 | 0 | 75 | 40 | 50 |  | 70 | 20 | 0 | 10 | 15 | N | 0 | 0 | N | 70 |  |  |  | 0 |
|  | 0.0701 | 25 | N | 15 | 0 | N | 0 | N |  | 0 | 0 | N | 0 | 10 | 0 | 0 | 0 | 0 | 0 |  |  |  | N |
|  | 0.0175 | 15 | 0 | N | 0 | 0 | 0 | 0 |  | 10 | 0 | 0 | 0 | 0 | 0 | 0 | 0 | 0 | 0 |  |  |  | 30 |
|  | 0.0087 | 20 | 15 | N | 0 | 0 | 0 | 0 |  | 0 | 0 | 0 | 0 | 0 | 0 | 0 | 0 | 0 | 0 |  |  |  | 0 |
| 43 | 5.6050 | 55 | 5 | 70 | 65 | 100 | 95 | 100 |  | 100 | 65 | 40 | 70 | 55 | 100 | 95 | 95 | 100 | 100 |  |  |  | 35 |
|  | 1.1210 | 80 | 30 | 65 | 40 | 95 | 75 | 0 |  | 55 | 30 | 0 | 20 | 40 | 45 | 0 | 70 | 90 | 70 |  |  |  | 0 |
|  | 0.2803 | 25 | 20 | 60 | 0 | 20 | 70 | 0 |  | 0 | 35 | 25 | 20 | 5 | 0 | 35 | 40 | 20 | 90 |  |  |  | 0 |
|  | 0.0701 | 35 | 35 | 0 | 0 | 0 | 70 | 0 |  | 40 | 40 | 0 | 40 | 35 | 0 | 30 | 50 | 0 | 55 |  |  |  | 75 |
| 44 | 5.6050 | 30 | 55 | 35 | 30 | 90 | 60 | 40 |  | 40 | 30 | 40 | 20 | 5 | 70 | 0 | 25 | 95 | 70 |  |  |  | 75 |
|  | 1.1210 | N | 10 | 35 | 0 | 85 | N | N |  | 50 | 30 | N | 0 | 5 | 35 | 0 | 20 | 90 | 0 |  |  |  | 0 |
|  | 0.2803 | N | 0 | 0 | N | 0 | 0 | 0 |  | 0 | N | 0 | 0 | N | 0 | 0 | 0 | 0 | 0 |  |  |  | 0 |
|  | 0.0701 | 30 | 0 | N | 0 | 0 | N | 0 |  | 0 | 0 | 0 | 0 | 20 | 0 | 0 | 0 | 0 | 0 | |  |  | 80 |
| 45 | 5.6050 | 20 | 85 | 95 | 100 | 100 | 100 | 100 |  | 100 | 25 | 75 | 35 | 0 | 30 | 90 | 70 | 75 | 70 |  |  |  | 75 |
|  | 1.1210 | N | 90 | 75 | 50 | 70 | 100 | 100 |  | 95 | 25 | 70 | 0 | 20 | N | 60 | 0 | 70 | 15 |  |  |  | 0 |
|  | 0.2803 | 40 | 0 | 40 | 0 | 0 | 90 | 0 |  | 0 | 25 | 0 | 0 | 20 | 0 | 0 | 0 | 0 | 0 |  |  |  | 100 |
|  | 0.0701 | N | 0 | 0 | N | 0 | 0 | 0 |  | 0 | 0 | 0 | 0 | 0 | 0 | 0 | 0 | 0 | 0 |  |  |  | 100 |
| 46 | 5.6050 | 95 | 70 | 100 | 55 | 100 | 100 | 100 |  | 100 | 45 | 85 | 90 | 90 | 95 | 100 | 100 | 100 | 100 |  |  |  | 70 |
|  | 1.1210 | 30 | 55 | 90 | 90 | 100 | 90 | 95 |  | 100 | 15 | 65 | 30 | 60 | 75 | 65 | 80 | 70 | 95 |  |  |  | 55 |
|  | 0.2803 | 0 | 25 | 35 | 30 | 65 | 70 | 75 |  | 30 | 0 | N | 0 | 10 | 0 | 35 | 35 | 85 | 15 |  |  |  | 35 |
|  | 0.0701 | 5 | 35 | 40 | 0 | 85 | 0 | 85 |  | 25 | 30 | N | 0 | 25 | N | 40 | 40 | 35 | 25 |  |  |  | 0 |
|  | 0.0175 | 30 | 15 | 35 | 0 | 75 | 0 | 40 |  | 0 | 15 | N | 0 | 30 | 25 | 0 | 0 | 0 | 0 |  |  |  | 100 |
|  | 0.0087 | 35 | 95 | 0 | 0 | 35 | 0 | 35 |  | 0 | 30 | 30 | 0 | 25 | 100 | 40 | 30 | 0 | 35 |  |  |  | 90 |
| 47 | 5.6050 | 95 | 95 | 100 | 95 | 100 | 100 | 100 |  | 100 | 90 | 95 | 100 | 95 | 100 | 100 | 100 | 100 | 100 |  |  |  | 35 |
|  | 1.1210 | 100 | 75 | 75 | 70 | 100 | 100 | 100 |  | 100 | 80 | 90 | 95 | 90 | 95 | 95 | 95 | 95 | 95 |  |  |  | 25 |
|  | 0.2803 | 60 | 5 | 10 | 40 | 95 | 100 | 90 |  | 90 | 25 | 70 | 70 | 65 | 40 | 80 | 0 | 90 | 90 |  |  |  | 20 |
|  | 0.0701 | 30 | 10 | 0 | 0 | 95 | 90 | 90 |  | 65 | 25 | 55 | 0 | 35 | 10 | 65 | 0 | 15 | 60 |  |  |  | 0 |
|  | 0.0175 | 15 | 0 | 0 | 0 | 70 | 0 | 0 |  | 30 | 0 | 25 | 0 | 5 | 0 | 0 | 0 | 35 | 5 |  |  |  | 0 |
|  | 0.0087 | 5 | 20 | 45 | 0 | 0 | 0 | 0 |  | 0 | 30 | 0 | 0 | 0 | 0 | 0 | 0 | 0 | 0 |  |  |  | 85 |
| 48 | 5.6050 | 20 | 25 | 10 | 95 | 100 | 70 | 100 |  | 95 | 15 | 85 | 90 | 90 | 85 | 100 | 90 | 90 | 95 |  |  |  | 0 |
|  | 1.1210 | 0 | 0 | 0 | 0 | 55 | 35 | 95 |  | 40 | 0 | 60 | 25 | 25 | 35 | 0 | 50 | 40 | 60 |  |  |  | 0 |
|  | 0.2803 | 0 | 5 | 0 | 0 | 0 | 25 | 0 |  | 0 | 0 | 40 | 5 | 20 | 0 | 40 | 0 | 15 | 5 |  |  |  | 0 |
|  | 0.0701 | 0 | 0 | 0 | 0 | 0 | 0 | 0 |  | 0 | 0 | 15 | 0 | 0 | 0 | 0 | 0 | 0 | 0 |  |  |  | 0 |
| 49 | 5.6050 | 70 | 40 | 50 | 55 | 100 | 100 | 99 |  | 100 | 55 | 95 | 90 | 90 | 100 | 95 | 95 | 100 | 100 |  |  |  | 95 |
|  | 1.1210 | 25 | 30 | 10 | 20 | 100 | 100 | 95 |  | 100 | 15 | 70 | 75 | 35 | 85 | 100 | 45 | 100 | 60 |  |  |  | 30 |
|  | 0.2803 | 0 | 15 | 0 | 0 | 100 | 100 | 85 |  | 25 | 0 | 45 | 10 | 30 | 10 | 60 | 25 | 55 | 25 |  |  |  | 0 |
|  | 0.0701 | 10 | 0 | 0 | 25 | 100 | 75 | 65 |  | 0 | 0 | 0 | 0 | 0 | 50 | 0 | 0 | 35 | 0 |  |  |  | 0 |
| 50 | 5.6050 | 65 | 75 | 45 | 50 | 100 | 100 | 99 |  | 100 | 90 | 85 | 90 | 90 | 100 | 100 | 95 | 100 | 95 |  |  |  | 90 |
|  | 1.1210 | 35 | 35 | 40 | 20 | 95 | 85 | 95 |  | 99 | 55 | 70 | 75 | 65 | 90 | 75 | 75 | 100 | 70 |  |  |  | 35 |
|  | 0.2803 | 0 | 20 | 0 | 0 | 0 | 0 | 65 |  | 65 | 15 | 45 | 10 | 30 | 65 | 25 | 15 | 90 | 10 |  |  |  | 10 |
|  | 0.0701 | 0 | N | 0 | 0 | 0 | 0 | 0 |  | 0 | 0 | 0 | 0 | 0 | 0 | 0 | 0 | 0 | 0 |  |  |  | 0 |
|  | 0.0175 | 0 | 0 | 0 | 0 | 0 | 0 | 0 |  | 0 | 5 | 0 | 0 | 0 | 0 | 0 | 0 | 0 | 0 |  |  |  | 0 |
|  | 0.0087 | 0 | 50 | 0 | 5 | 100 | 45 | 90 |  | 70 | 5 | 10 | 5 | 0 | 95 | 55 | 50 | 100 | 85 |  |  |  | 30 |
| 51 | 5.6050 | 0 | 50 | 0 | 5 | 100 | 45 | 90 |  | 70 | 5 | 10 | 5 | 0 | 95 | 55 | 50 | 100 | 85 |  |  |  | 30 |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| 52 | 1.1210 | 0 | 40 | 0 | 0 | 30 | 10 | 10 | | 25 | 0 | 5 | 5 | 0 | 10 | 0 | 0 | 55 | 0 | | | | 50 |
|  | 0.2803 | 0 | 25 | 0 | 0 | 5 | 0 | 0 | | 0 | 0 | 0 | 0 | 0 | 0 | 0 | 0 | 15 | 55 | | | | 20 |
|  | 5.6050 | 35 | 50 | 100 | 55 | 90 | 100 | 100 | | 100 | 25 | 30 | 15 | 45 | 45 | 25 | 65 | 0 | 0 | | | | 100 |
|  | 1.1210 | 10 | 5 | 55 | 20 | 85 | 95 | 85 | | 100 | 0 | 10 | 0 | 30 | 20 | 25 | 5 | N | 0 | | | | 90 |
|  | 0.2803 | 5 | 25 | 10 | 15 | 80 | 65 | 30 | | 65 | 10 | 0 | 0 | 5 | 20 | 15 | 0 | 5 | 0 | | | | 10 |
|  | 0.0175 | 25 | 10 | 0 | 15 | 100 | 30 | 95 | | 95 | 0 | 25 | 0 | 0 | 30 | N | 0 | 20 | 0 | | | | N |
| 53 | 5.6050 | 15 | 5 | 0 | 0 | 0 | 30 | N | | 0 | 15 | 40 | 15 | 10 | 30 | 0 | 55 | 0 | 0 | | | | 0 |
|  | 1.1210 | 30 | 40 | 65 | 55 | 100 | 95 | 100 | | 65 | 25 | 35 | 0 | 15 | 0 | 15 | 30 | 75 | 90 | | | | 85 |
|  | 0.2803 | 30 | 10 | 35 | 30 | 100 | 60 | 100 | | 35 | 35 | 25 | 15 | 5 | 30 | 25 | 20 | 55 | 0 | | | | 90 |
|  | 0.0701 | 10 | 10 | 35 | 0 | 75 | 10 | 100 | | N | 10 | N | 0 | 5 | 0 | 20 | 0 | 20 | 25 | | | | 30 |
| 54 | 5.6050 | N | N | 0 | 0 | N | 0 | N | | N | 40 | 10 | 0 | 5 | N | N | 30 | N | 0 | | | | N |
|  | 1.1210 | 55 | 10 | 95 | 70 | 100 | 100 | 100 | | 100 | 25 | 10 | 65 | 55 | 75 | 100 | 100 | 95 | 100 | | | | 75 |
|  | 0.2803 | 20 | 10 | 35 | 0 | 100 | 10 | 100 | | 95 | 10 | N | 15 | 20 | 75 | 90 | 65 | 100 | 95 | | | | N |
|  | 0.0701 | 10 | 10 | 35 | 0 | 0 | 0 | N | | 0 | 0 | 0 | 0 | 10 | 0 | 0 | 10 | 0 | 80 | | | | 0 |
| 55 | 5.6050 | N | 0 | 20 | 0 | N | 0 | N | | N | 30 | N | 0 | N | N | 0 | 10 | N | 10 | | | | N |
|  | 1.1210 | 60 | 25 | 95 | 10 | 100 | 100 | 100 | | 100 | 10 | 0 | 70 | 25 | 25 | 100 | 70 | 100 | 90 | | | | 90 |
|  | 0.2803 | 70 | 70 | 85 | 0 | 95 | 100 | 80 | | 75 | 30 | 0 | 35 | 15 | 25 | 80 | 60 | 70 | 75 | | | | 45 |
|  | 0.0701 | 45 | 25 | 75 | 0 | 90 | 100 | 80 | | 10 | 10 | N | 15 | 10 | 20 | 35 | 10 | 70 | 35 | | | | 35 |
| 56 | 5.6050 | 35 | 0 | 45 | 10 | 70 | 30 | 35 | | 30 | 15 | 0 | N | 25 | 0 | 0 | 0 | 0 | 45 | | | | 0 |
|  | 1.1210 | 10 | N | N | 0 | 65 | N | N | | 100 | 65 | 40 | 80 | 20 | 0 | 85 | 30 | 90 | N | | | | N |
|  | 0.2803 | 80 | 25 | 90 | 0 | 95 | 100 | 100 | | 100 | 20 | 50 | 25 | 85 | 0 | 75 | 95 | 95 | 100 | | | | 35 |
|  | 0.0701 | 30 | 30 | 95 | 90 | 100 | 100 | 95 | | N | 60 | N | 0 | 30 | 0 | 55 | 40 | 85 | 75 | | | | 40 |
| 57 | 5.6050 | 35 | 65 | 50 | 30 | 90 | 10 | 90 | | 60 | 30 | N | 55 | 20 | N | 0 | 0 | 55 | 15 | | | | N |
|  | 1.1210 | 30 | 10 | 90 | 0 | 100 | 95 | 100 | | 100 | 45 | 70 | 30 | 5 | 35 | 95 | 100 | 100 | 100 | | | | 80 |
|  | 0.2803 | 25 | 30 | 30 | 0 | 100 | 90 | 25 | | 30 | 20 | 25 | 15 | 60 | 100 | 40 | 55 | 95 | 75 | | | | 100 |
|  | 0.0701 | 20 | 15 | 0 | 0 | 75 | 90 | 0 | | 35 | 20 | 40 | 30 | 25 | 45 | 60 | 30 | 60 | 30 | | | | 35 |
| 58 | 5.6050 | 15 | 10 | 0 | 0 | 40 | 0 | 65 | 10 | 0 | 0 | 55 | 15 | 25 | 35 | 0 | 0 | 10 | 0 | | | | 0 |
|  | 1.1210 | 0 | 0 | 70 | 0 | 0 | 0 | 50 | 0 | 35 | 0 | 25 | 0 | 20 | 0 | 0 | 0 | 0 | 0 | | | | 0 |
|  | 1.1210 | 0 | N | 15 | 40 | 0 | 0 | 30 | 0 | 0 | 0 | 25 | 0 | 25 | 0 | 0 | 0 | 0 | 0 | | | | 0 |
|  | 0.2803 | 95 | N | 10 | 0 | 0 | 0 | 0 | 0 | 60 | 0 | 0 | 0 | 25 | 0 | 0 | 0 | 0 | 0 | | | | |
|  | 0.0701 | | | 0 | 0 | 0 | 0 | 0 | 0 | 15 | 0 | 0 | 0 | 0 | 0 | 0 | 0 | 0 | 0 | | | | |
|  | 0.0701 | 25 | | 0 | | 0 | 0 | 0 | | 0 | 0 | 0 | 0 | 0 | 0 | 0 | 0 | 0 | 0 | | | | |
|  | 0.0175 | 10 | N | 0 | 10 | 0 | 0 | 0 | 0 | 0 | 0 | 0 | 0 | 0 | 0 | 0 | 0 | 0 | 0 | | | | |
|  | 0.0087 | 0 | | 0 | 0 | 0 | 0 | 0 | 0 | 0 | 0 | 0 | 0 | 0 | 0 | 0 | 0 | 0 | 0 | | | | |
| 59 | 5.6050 | 0 | N | 0 | 50 | 0 | 0 | 80 | 40 | 75 | 0 | 70 | 55 | 5 | 0 | 85 | 0 | 0 | 0 | | | | |
|  | 1.1210 | 30 | | 0 | | 0 | 0 | 80 | 0 | 0 | 0 | 25 | 30 | 25 | 45 | 75 | 100 | 95 | 100 | | | | 80 |
|  | 1.1210 | 15 | | 0 | | 0 | 0 | 15 | 0 | 0 | 0 | 40 | 15 | 25 | 35 | 55 | 55 | 60 | 75 | | | | 100 |
|  | 0.2803 | | N | 35 | 0 | 0 | 0 | 40 | 0 | 0 | 0 | 55 | 0 | 25 | 0 | 60 | 30 | 10 | 30 | | | | 35 |
|  | 0.0701 | 0 | | 10 | 0 | 0 | 0 | 0 | 0 | 0 | 0 | 25 | 0 | 0 | 0 | 0 | 0 | 0 | 0 | | | | 0 |
|  | 0.0175 | 0 | N | 0 | 0 | 0 | 0 | 0 | 0 | 0 | 0 | 0 | 0 | 0 | 0 | 0 | 0 | 0 | 0 | | | | 0 |
| 60 | 5.6050 | 90 | N | 100 | 100 | 0 | 0 | 100 | 100 | 100 | 0 | | | | | | | | | | | | |
|  | 1.1210 | | N | 95 | 100 | 0 | 0 | 100 | 98 | 99 | 0 | | | | | | | | | | | | |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
|  | 1.1210 | 35 |  | 100 |  | 0 |  | 90 |  |  | 0 |  |  |  |  |  |  |  |  |  |  |  |  |
|  | 0.2803 | 20 |  | 95 |  | 0 |  | 10 |  |  | 0 |  |  |  |  |  |  |  |  |  |  |  |  |
|  | 0.0701 |  | N | 30 | 99 | 0 | 0 | 60 | 40 | 50 | 0 |  |  |  |  |  |  |  |  |  |  |  |  |
|  | 0.0175 |  | N | 5 | 60 | 0 | 0 | 25 | 0 | 0 | 0 |  |  |  |  |  |  |  |  |  |  |  |  |
|  | 0.0175 |  |  | 60 |  |  |  | 0 |  |  | 0 |  |  |  |  |  |  |  |  |  |  |  |  |
|  | 0.0175 |  |  | 55 |  |  |  | 0 |  |  | 0 |  |  |  |  |  |  |  |  |  |  |  |  |
|  | 0.0175 |  |  | 0 | 0 |  |  | 0 | 5 | 0 | 0 |  |  |  |  |  |  |  |  |  |  |  |  |
| 61 | 5.6050 | 100 |  | 100 |  | 0 |  | 100 |  |  | 0 |  |  |  |  |  |  |  |  |  |  |  |  |
|  | 5.6050 |  | N | 100 | 99 | 0 | 0 | 90 | 95 | 90 | 0 |  |  |  |  |  |  |  |  |  |  |  |  |
|  | 1.1210 |  | N | 98 | 98 | 0 | 0 | 40 | 90 | 20 | 0 |  |  |  |  |  |  |  |  |  |  |  |  |
|  | 1.1210 | 60 |  | 85 |  |  |  | 20 |  |  | 0 |  |  |  |  |  |  |  |  |  |  |  |  |
|  | 0.2803 | 10 |  | 30 |  |  |  | 0 |  |  | 0 |  |  |  |  |  |  |  |  |  |  |  |  |
|  | 0.2803 |  | N | 15 | 70 |  |  | 0 | N | 0 | 0 |  |  |  |  |  |  |  |  |  |  |  |  |
|  | 0.0701 |  |  | 0 | 30 |  |  | 0 | 0 | 0 | 0 |  |  |  |  |  |  |  |  |  |  |  |  |
|  | 0.0701 | 0 |  | 0 |  |  |  | 0 |  |  | 0 |  |  |  |  |  |  |  |  |  |  |  |  |
|  | 0.0175 | 0 |  | 0 |  |  |  | 0 |  |  | 0 |  |  |  |  |  |  |  |  |  |  |  |  |
|  | 0.0175 |  | N | 0 | 20 |  |  | 0 | 0 | 95 | 0 |  |  |  |  |  |  |  |  |  |  |  |  |
| 62 | 5.6050 | 95 |  | 100 |  |  |  | 100 |  |  | 0 |  |  |  |  |  |  |  |  |  |  |  |  |
|  | 5.6050 |  | N | 100 | 100 |  |  | 100 | 90 | 95 | 0 |  |  |  |  |  |  |  |  |  |  |  |  |
|  | 1.1210 |  | N | 98 | 100 |  |  | 99 | 85 | 0 | 0 |  |  |  |  |  |  |  |  |  |  |  |  |
|  | 1.1210 | 30 |  | 90 |  |  |  | 20 |  |  | 0 |  |  |  |  |  |  |  |  |  |  |  |  |
|  | 0.2803 | 1 |  | 55 |  |  |  | 0 |  |  | 0 |  |  |  |  |  |  |  |  |  |  |  |  |
|  | 0.2803 |  | N | 80 | 60 |  |  | 50 | 10 | 0 | 0 |  |  |  |  |  |  |  |  |  |  |  |  |
|  | 0.0701 |  |  | 0 | 10 |  |  | 15 | 10 | 0 | 0 |  |  |  |  |  |  |  |  |  |  |  |  |
|  | 0.0701 | 0 |  | 0 |  |  |  | 0 |  |  | 0 |  |  |  |  |  |  |  |  |  |  |  |  |
|  | 0.0175 | 0 |  | 0 |  |  |  | 15 |  |  | 0 |  |  |  |  |  |  |  |  |  |  |  |  |
|  | 0.0175 |  | N | 0 | 0 |  |  | 0 | 0 | 0 | 0 |  |  |  |  |  |  |  |  |  |  |  |  |
|  | 0.0044 |  | N | 0 | 0 |  |  | 0 | 0 | 0 | 0 |  |  |  |  |  |  |  |  |  |  |  |  |
|  | 0.0044 | 0 |  | 0 |  |  |  | 0 |  |  | 0 |  |  |  |  |  |  |  |  |  |  |  |  |
| 63 | 5.6050 | 90 | 30 | 90 | 45 | 100 | 90 | 99 |  | 100 | 90 | 55 | 95 | 90 | 90 | 100 | 95 | 100 | 100 |  |  |  | 40 |
|  | 1.1210 | 45 | 20 | 30 | 10 | 95 | 75 | 85 |  | 90 | 40 | 40 | 75 | 60 | 70 | 90 | 90 | 98 | 95 |  |  |  | 0 |
|  | 0.2803 | 20 | 0 | 15 | 0 | 40 | 20 | 0 |  | 20 | 10 | 0 | 30 | 50 | 15 | 50 | 20 | 70 | 50 |  |  |  | 10 |
|  | 0.0701 | 0 | 0 | 10 | 0 | 0 | 0 | 0 |  | 0 | 10 | 0 | 10 | 0 | 0 | 10 | 20 | 10 | 10 |  |  |  | 0 |
|  | 0.0175 | 0 | 0 | 0 | 0 | 0 | 0 | 0 |  | 0 | 0 | 0 | 0 | 0 | 0 | 0 | 0 | 0 | 0 |  |  |  | 15 |
|  | 0.0087 | 0 | 0 | 0 | 0 | 0 | 15 | 0 |  | 0 | 25 | 85 | 10 | 95 | 100 | 99 | 0 | 100 | 0 |  |  |  | 0 |
| 64 | 5.6050 | 85 | 35 | 50 | 20 | 100 | 100 | 100 |  | 100 | 25 | 55 | 75 | 85 | 100 | 95 | 95 | 90 | 99 |  |  |  | 95 |
|  | 1.1210 | 50 | 25 | 35 | 0 | 100 | 100 | 95 |  | 98 | 25 | 30 | 55 | 10 | 90 | 65 | 50 | 95 | 15 |  |  |  | 85 |
|  | 0.2803 | 40 | 10 | 10 | 0 | 75 | 50 | 70 |  | 50 | 0 | 25 | 10 | 15 | 35 | 15 | 10 | 10 | 10 |  |  |  | 15 |
|  | 0.0701 | 10 | 15 | 0 | 10 | 65 | 0 | 45 |  | 25 | 10 | 10 | 0 | 20 | 60 | 0 | 10 | 0 | 0 |  |  |  | 35 |
|  | 0.0175 | 0 | 0 | 10 | 0 | 25 | 0 | 0 |  | 0 | 0 | 50 | 45 | 85 | 50 | 75 | 98 | 100 | 98 |  |  |  | 100 |
| 65 | 5.6050 | 90 | 15 | 30 | 0 | 100 | 100 | 98 |  | 100 | 20 | 0 | 35 | 70 | 20 | 20 | 85 | 98 | 75 |  |  |  | 10 |
|  | 1.1210 | 10 | 5 | 30 | 0 | 98 | 65 | 98 |  | 65 | 25 | 15 | 5 | 15 | 60 | 0 | 50 | 0 | 40 |  |  |  | 70 |
|  | 0.2803 | 10 | 10 | 0 | 0 | 100 | 0 | 55 |  | 25 | 10 | 15 | 0 | 5 | 20 | 0 | 0 | 0 | 15 |  |  |  | 0 |
|  | 0.0701 | 10 | 20 | 0 | 0 | 55 | 0 | 45 |  | 10 | 10 | 10 | 0 | 0 | 0 | 0 | 0 | 0 | 20 |  |  |  | 0 |
|  | 0.0175 | 0 | 15 | 0 | 0 | 0 | 0 | 0 |  | 0 | 10 | 70 | 0 | 0 | 0 | 0 | 0 | 100 | 10 |  |  |  | 40 |
|  | 0.0087 | 0 | 20 | 0 | 0 | 100 | 0 | 0 |  | 0 | 10 | 70 | 25 | 70 | 95 | 95 | 95 | 100 | 95 |  |  |  | 99 |
| 66 | 5.6050 | 35 | 60 | 10 | 20 | 100 | 70 | 99 |  | 90 | 10 | 25 | 25 | 50 | 85 | 70 | 40 | 55 | 75 |  |  |  | 60 |
|  | 1.1210 | 40 | 75 | 10 | 0 | 85 | 35 | 70 |  | 15 | 20 | 25 | 10 | 60 | 10 | 0 | 10 | 0 | 20 |  |  |  | 40 |
|  | 0.2803 | 0 | 0 | 0 | 0 | 15 | 10 | 10 |  | 0 | 10 | 25 | 25 | 0 | 35 | 15 | 0 | 15 | 0 |  |  |  | 40 |
|  | 0.0701 | 0 | 30 | 0 | 0 | 70 | 0 | 15 |  | 15 | 20 | 10 | 25 | 0 | 55 | 10 | 0 | 0 | 0 |  |  |  | 0 |
|  | 0.0175 | 0 | 0 | 0 | 0 |  | 0 | 15 |  |  | 0 |  |  |  |  |  |  |  |  |  |  |  | 35 |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| 67 | 5.6050 | 20 | 5 | 60 | 65 | 95 | 80 | 50 | | 100 | 5 | 25 | 5 | 0 | 0 | 35 | 80 | 90 | 100 | | | | 90 |
|  | 1.1210 | 0 | 30 | 0 | 25 | 95 | 10 | 75 | | 60 | 0 | 30 | 5 | 20 | 15 | N | 55 | 95 | 80 | | | | 20 |
|  | 0.2803 | 20 | 35 | 0 | 0 | 15 | 65 | 60 | | 65 | 0 | 35 | 0 | 10 | 10 | 50 | 0 | 65 | 0 | | | | 0 |
|  | 0.0701 | 55 | N | 95 | 35 | 15 | 15 | 15 | | 70 | 55 | N | 65 | 0 | 0 | 55 | 0 | 50 | 0 | | | | 10 |
| 68 | 5.6050 | 0 | 70 | 50 | 95 | 95 | 95 | 100 | | 100 | 10 | 50 | 10 | 75 | 95 | 100 | 80 | 95 | 100 | | | | 100 |
|  | 1.1210 | 0 | 35 | 10 | 55 | 95 | 55 | 90 | | 100 | 0 | 30 | 5 | 10 | 25 | 90 | 5 | 80 | 45 | | | | 95 |
|  | 0.2803 | 0 | 20 | 0 | 0 | 20 | 80 | 95 | | 80 | 0 | 10 | 0 | 5 | 5 | 55 | 0 | 55 | 0 | | | | 50 |
|  | 0.0701 | 20 | N | 0 | N | 25 | 0 | 60 | | 50 | 10 | 15 | 0 | 5 | 30 | 55 | 5 | 50 | 0 | | | | 10 |
|  | 0.0175 | 0 | 25 | 0 | 20 | 40 | 35 | 10 | | 0 | 0 | 0 | 0 | 0 | 15 | 50 | 0 | 55 | 0 | | | | N |
|  | 0.0087 | 5 | 5 | 0 | 0 | 10 | 30 | 65 | | 0 | 10 | 15 | 0 | 15 | 55 | 30 | 90 | 75 | 0 | | | | 10 |
| 69 | 5.6050 | 0 | 10 | 80 | 65 | 80 | 90 | 70 | | 100 | 15 | 75 | 30 | 20 | 45 | 55 | 0 | 60 | 99 | | | | 95 |
|  | 1.1210 | 5 | 25 | 10 | 0 | 70 | 10 | 55 | | 85 | 15 | 60 | 5 | 10 | 0 | 45 | 20 | 55 | 20 | | | | 80 |
|  | 0.2803 | 20 | 0 | 0 | 0 | 0 | 0 | 0 | | 60 | 35 | 10 | 10 | 20 | 10 | 0 | 10 | 0 | 45 | | | | 0 |
|  | | 10 | 10 | 0 | 0 | 15 | 5 | 50 | | 0 | 15 | 35 | 15 | 50 | 25 | 40 | 20 | 35 | 15 | | | | 0 |
|  | 0.0175 | 15 | 15 | 10 | 0 | 35 | 0 | 60 | | 10 | 15 | 35 | 0 | 40 | 50 | 0 | 10 | 70 | 10 | | | | 20 |
|  | 0.0087 | 0 | 0 | 0 | 0 | 35 | 5 | 45 | | 0 | 35 | 15 | 15 | 50 | 60 | 20 | 80 | 70 | 0 | | | | 10 |
| 70 | 5.6050 | 20 | 45 | 95 | 80 | 95 | 100 | 100 | | 100 | 20 | 55 | 40 | 20 | 60 | 75 | 80 | 70 | 95 | | | | 95 |
|  | 1.1210 | 10 | 10 | 60 | 15 | 75 | 65 | 95 | | 98 | 25 | 50 | 15 | 50 | 60 | 45 | 25 | 70 | 70 | | | | 90 |
|  | 0.2803 | 15 | 15 | 15 | 0 | 30 | 55 | 85 | | 60 | 0 | 75 | 0 | 20 | 60 | 20 | 0 | 50 | 0 | | | | 55 |
|  | 0.0701 | 10 | 30 | 0 | 0 | 40 | 20 | 40 | | 40 | 25 | 15 | 0 | 0 | 50 | 15 | 0 | 15 | 10 | | | | 50 |
|  | 0.0175 | 20 | 15 | 20 | 0 | 15 | 35 | 60 | | 30 | 0 | 15 | 0 | 0 | 50 | 0 | 0 | 0 | 10 | | | | 45 |
|  | 0.0087 | 0 | 0 | 15 | 0 | 0 | 0 | 35 | | 0 | 10 | 15 | 0 | N | 0 | 65 | 0 | 15 | 10 | | | | 0 |
| 71 | 5.6050 | 25 | 10 | 70 | 70 | 95 | 100 | 70 | | 100 | 35 | 65 | 30 | 35 | 70 | 65 | 95 | 98 | 99 | | | | 95 |
|  | 1.1210 | 35 | 15 | 20 | 10 | 35 | 85 | 55 | | 85 | 20 | 50 | 5 | 10 | 40 | 10 | 0 | 25 | 10 | | | | 75 |
|  | 0.2803 | 30 | 15 | 15 | 0 | 5 | 40 | 55 | | 5 | 15 | 15 | 25 | 20 | 25 | 10 | 5 | 15 | 10 | | | | 20 |
|  | 0.0701 | 0 | 20 | 0 | 0 | 0 | 0 | 45 | | 0 | 25 | 15 | 0 | 0 | 10 | 0 | 0 | 55 | 15 | | | | 25 |
|  | 0.0175 | 10 | 0 | 20 | 0 | 10 | 0 | 30 | | 30 | 0 | 15 | 0 | 20 | 50 | 30 | 0 | 15 | 15 | | | | 40 |
|  | 0.0087 | 20 | 20 | 15 | 0 | 50 | 0 | 25 | | 0 | 0 | 0 | 0 | 0 | 100 | 0 | 0 | 25 | 15 | | | | 20 |
| 72 | 5.6050 | 100 | 98 | 100 | 95 | 100 | 100 | 100 | | 100 | 75 | 90 | 90 | 85 | 50 | 100 | 100 | 100 | 100 | | | | 100 |
|  | 1.1210 | 75 | 90 | 90 | 25 | 100 | 85 | 100 | | 100 | 20 | 75 | 50 | 30 | 100 | 100 | 90 | 100 | 95 | | | | 100 |
|  | 0.2803 | 20 | 45 | 70 | 15 | 90 | 55 | 100 | | 85 | 25 | 30 | 25 | 15 | 99 | 70 | 25 | 85 | 90 | | | | 90 |
|  | 0.0701 | 20 | 65 | 10 | 0 | 50 | 35 | 50 | | 15 | 10 | 0 | 10 | 10 | 70 | 20 | 15 | 20 | 75 | | | | 15 |
|  | 0.0175 | 20 | 15 | 0 | 15 | 0 | 45 | 40 | | 15 | 15 | 0 | 0 | 0 | 20 | 0 | 0 | 60 | 0 | | | | 10 |
|  | 0.0087 | 0 | 15 | 0 | 0 | 0 | 0 | 0 | | 0 | 40 | 0 | 0 | 20 | 0 | 20 | 0 | 60 | 0 | | | | 100 |
| 73 | 5.6050 | 90 | 90 | 100 | 70 | 100 | 90 | 100 | | 100 | 15 | 45 | 50 | 0 | 70 | 85 | 90 | 100 | 100 | | | | 90 |
|  | 1.1210 | 15 | 30 | 50 | 30 | 95 | 40 | 100 | | 100 | 40 | 35 | 0 | 20 | 0 | 35 | 20 | 80 | 65 | | | | 90 |
|  | 0.2803 | 0 | 40 | 20 | 0 | 75 | 0 | 90 | | 75 | 15 | 35 | 0 | 0 | 25 | 20 | 10 | 30 | 0 | | | | 15 |
|  | 0.0701 | N | 50 | 0 | 0 | 0 | 0 | 0 | | 15 | 0 | 10 | 0 | 5 | 0 | 0 | 0 | 20 | 0 | | | | 10 |
|  | 0.0175 | 15 | 0 | 0 | 15 | 10 | 0 | 10 | | 0 | 15 | 0 | 0 | 0 | 15 | 0 | 0 | 20 | 0 | | | | 25 |
|  | 0.0087 | 20 | 0 | 0 | 0 | 0 | 15 | 100 | | 75 | 85 | 50 | 0 | 55 | 50 | 0 | 10 | 100 | 0 | | | | 100 |
| 74 | 5.6050 | 40 | 60 | 50 | 40 | 75 | 90 | 0 | | 100 | 40 | 50 | 60 | 20 | 90 | 95 | 95 | 100 | 65 | | | | 98 |
|  | 1.1210 | 55 | 15 | 65 | 0 | 55 | 10 | 85 | | 100 | 35 | 35 | 50 | 0 | 55 | 40 | 30 | 99 | 0 | | | | 75 |
|  | 0.2803 | 10 | 20 | 50 | 0 | 50 | 0 | 80 | | 75 | 0 | 50 | 10 | 0 | 0 | 10 | 0 | 45 | 0 | | | | 20 |
|  | 0.0701 | 20 | 0 | N | 0 | 75 | 10 | 40 | | 15 | 0 | 0 | 0 | 0 | 15 | 0 | 0 | 35 | 0 | | | | 0 |
|  | 0.0175 | 0 | 0 | 0 | 0 | 0 | 10 | 30 | | 0 | 15 | 0 | 0 | 15 | 0 | 0 | 0 | 10 | 0 | | | | 0 |
|  | 0.0087 | 20 | 0 | 0 | 0 | 0 | 0 | 0 | | 0 | 0 | 0 | 0 | 10 | 0 | 0 | 0 | 0 | 0 | | | | 90 |
| 75 | 5.6050 | 60 | 60 | 45 | 50 | 100 | 70 | 85 | | 90 | 15 | 75 | 60 | 0 | 100 | 95 | 98 | 98 | 100 | | | | 10 |
|  | 1.1210 | 50 | 30 | 15 | 0 | 75 | 55 | 80 | | 50 | 85 | 70 | 30 | 40 | 80 | 75 | 40 | 98 | 60 | | | | 0 |
|  | 0.2803 | 15 | 20 | 0 | 0 | 55 | 0 | 40 | | 0 | 50 | 55 | 10 | 15 | 10 | 20 | 0 | 0 | 25 | | | | 0 |
|  | 0.0701 | 0 | 25 | 0 | 0 | 50 | 0 | 30 | | 15 | 15 | 30 | 0 | 0 | N | 25 | 0 | 0 | 10 | | | | 40 |
|  | 0.0175 | 20 | 10 | 30 | 50 | 75 | 10 | 10 | | 25 | 15 | 50 | 10 | 10 | N | 35 | 0 | 0 | 25 | | | | 20 |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| 76 | 5.6050 | 50 | 30 | 80 | 50 | 100 | 90 | 100 | | 90 | 35 | 60 | 90 | 75 | 90 | 99 | 100 | 100 | 100 | | | | 100 |
| | 1.1210 | 50 | 0 | 0 | 0 | 90 | 85 | 40 | | 40 | 30 | 25 | 25 | 35 | 40 | 30 | 90 | 100 | 90 | | | | 85 |
| | 0.2803 | 0 | 0 | N | 0 | 60 | 0 | 0 | | 10 | 0 | 0 | 10 | 0 | 10 | 0 | 20 | 90 | 90 | | | | 50 |
| | 0.0701 | 0 | 0 | 0 | 0 | 0 | 15 | 0 | | 0 | 0 | 0 | 0 | 0 | 0 | 0 | 0 | 0 | 55 | | | | 10 |
| | 0.0175 | 0 | 0 | 0 | 100 | 0 | 0 | 0 | | 60 | 10 | | | | | | | 10 | 25 | | | | |
| 78 | 5.6050 | 90 | 0 | 99 | 99 | | | 100 | 20 | 0 | 25 | | | | | | | | | | | | |
| | 1.1210 | 25 | 0 | 100 | 60 | | | 95 | 0 | 0 | 25 | | | | | | | | | | | | |
| | 1.1210 | | | 90 | | | | 80 | 0 | 100 | 10 | | | | | | | | | | | | |
| | 0.2803 | 0 | 0 | 50 | 25 | | | 95 | 0 | 0 | 0 | 25 | | | | | | | | | | | |
| | 0.2803 | 0 | 0 | 20 | 100 | | | 50 | 90 | 0 | 25 | | | | | | | | | | | | |
| | 0.0701 | | | 65 | 100 | | | 10 | 30 | 100 | 10 | | | | | | | | | | | | |
| | 0.0701 | | | 0 | 100 | | | 0 | 0 | 100 | 25 | | | | | | | | | | | | |
| 79 | 5.6050 | 98 | 0 | 100 | 100 | | | 20 | 90 | 80 | 10 | | | | | | | | | | | | |
| | 1.1210 | 70 | 0 | 100 | 100 | | | 100 | 40 | 40 | 10 | | | | | | | | | | | | |
| | 1.1210 | | | 100 | 100 | | | 100 | 0 | 0 | 10 | | | | | | | | | | | | |
| | 0.2803 | | | 99 | 99 | | | 100 | 15 | 75 | 25 | | | | | | | | | | | | |
| | 0.2803 | 25 | 0 | 98 | | | | 98 | | | 10 | | | | | | | | | | | | |
| | 0.0701 | 15 | 0 | 70 | 95 | | | 50 | 10 | 60 | 10 | | | | | | | | | | | | |
| | 0.0701 | | | 60 | 60 | | | 90 | 0 | 0 | 10 | | | | | | | | | | | | |
| | 0.0175 | | | 100 | 20 | | | 95 | 0 | 60 | 25 | | | | | | | | | | | | |
| | 0.0175 | 0 | 0 | 10 | 0 | | | 20 | 0 | 0 | 25 | | | | | | | | | | | | |
| | 0.0044 | 0 | 0 | 0 | 0 | | | 0 | 0 | 0 | 10 | | | | | | | | | | | | |
| | 0.0044 | | | 0 | 0 | | | 0 | 0 | 55 | 10 | | | | | | | | | | | | |
| 80 | 5.6050 | 98 | 0 | 100 | 0 | | | 100 | 0 | 0 | 10 | | | | | | | | | | | | |
| | 5.6050 | 35 | 0 | 100 | 100 | | | 100 | 100 | 100 | 25 | | | | | | | | | | | | |
| | 1.1210 | | | 99 | 99 | | | 95 | 50 | 75 | 25 | | | | | | | | | | | | |
| | 1.1210 | | | 10 | 0 | | | 100 | 0 | 0 | 10 | | | | | | | | | | | | |
| | 0.2803 | 0 | 0 | 99 | 0 | | | 20 | 0 | 0 | 25 | | | | | | | | | | | | |
| | 0.2803 | 0 | 0 | 10 | 20 | | | 0 | 0 | 0 | 10 | | | | | | | | | | | | |
| | 0.0701 | | | 80 | 0 | | | 0 | 0 | 0 | 10 | | | | | | | | | | | | |
| | 0.0175 | 0 | 0 | 10 | 0 | | | 0 | 0 | 0 | 25 | | | | | | | | | | | | |
| | 0.0175 | 0 | 0 | 0 | 0 | | | 0 | 0 | 0 | 25 | | | | | | | | | | | | |
| | 0.0044 | | | 0 | 0 | | | 0 | 0 | 0 | 10 | | | | | | | | | | | | |
| | 0.0044 | | | 0 | 0 | | | 0 | 0 | 0 | 10 | | | | | | | | | | | | |
| 81 | 5.6050 | 15 | 30 | 25 | 40 | 100 | 100 | 90 | 0 | 0 | 15 | 55 | 20 | 25 | 60 | 20 | 10 | 100 | 25 | | | | 95 |
| | 1.1210 | 0 | 15 | 20 | 60 | 90 | 85 | 100 | 65 | 0 | 30 | 40 | 20 | 0 | 30 | 0 | 0 | 60 | 0 | | | | 35 |
| | 0.2803 | 0 | 30 | 0 | 0 | 70 | 90 | 70 | 35 | 0 | 0 | 0 | 0 | 0 | 25 | 15 | 0 | 0 | 0 | | | | 0 |
| | 0.0701 | 0 | 0 | 0 | 0 | N | 0 | 0 | 0 | 0 | 0 | 0 | 0 | 0 | 0 | 0 | 0 | 0 | 0 | | | | 0 |
| | 0.0175 | 0 | 15 | 0 | 0 | 80 | 80 | 70 | 0 | 45 | 5 | 0 | 10 | 10 | 0 | 10 | 5 | 95 | 75 | | | | 20 |
| | 0.0175 | 0 | 10 | 0 | 0 | 30 | 25 | 60 | 0 | 50 | 0 | 0 | 0 | 0 | 0 | 35 | 0 | 75 | 10 | | | | 20 |
| 84 | 0.2803 | N | N | 10 | 20 | 15 | 45 | 25 | 0 | 50 | 0 | 0 | 20 | 10 | 15 | 0 | 20 | 80 | 10 | | | | 15 |

TABLE C-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Colq | Pesw | Cocw |
|---|---|---|---|---|---|---|---|---|---|---|---|---|---|---|---|---|---|---|---|---|---|---|---|
| 85 | 0.0701 | 0 | N | 0 | 0 | N | 0 | N | | 50 | 0 | 0 | 0 | 15 | 0 | 0 | 0 | 0 | 0 | | | | 30 |
| | 5.6050 | 15 | 10 | 15 | 0 | 100 | 15 | 95 | | 100 | 20 | 10 | 15 | 0 | 90 | 70 | 50 | 100 | 90 | | | | 99 |
| | 1.1210 | 0 | 5 | 40 | 0 | 70 | 0 | 15 | | 10 | 10 | 0 | 10 | 0 | 0 | 0 | 15 | 65 | 85 | | | | 0 |
| | 0.2803 | 10 | 0 | 25 | 0 | 10 | 20 | 0 | | 0 | 20 | 0 | 0 | 0 | 0 | 0 | 0 | 15 | 15 | | | | 0 |
| | 0.0701 | 0 | 0 | 15 | 0 | 10 | 0 | 35 | | 0 | 10 | 10 | 0 | 0 | 0 | 10 | 20 | 0 | 10 | | | | 0 |
| 86 | 5.6050 | 35 | 5 | 80 | 0 | 100 | 50 | 45 | | 45 | 10 | 0 | 35 | 0 | 0 | 0 | 65 | 95 | 99 | | | | 95 |
| | 1.1210 | 0 | 0 | 15 | 0 | 60 | 0 | 0 | | 0 | 0 | 0 | 10 | 0 | 0 | 0 | 30 | 85 | 70 | | | | 15 |
| | 0.2803 | 50 | 0 | 0 | 0 | 0 | 0 | 0 | | 0 | 0 | 0 | 0 | 10 | 0 | 0 | 0 | 0 | 15 | | | | 0 |
| | 0.0701 | 0 | 10 | 0 | 0 | 0 | 0 | 10 | | 0 | 0 | 15 | 0 | 0 | 0 | 0 | 0 | 0 | 20 | | | | 0 |

POST-EMERGENCE ACTIVITY ON WEEDS AND CROPS

Compounds of this invention were tested for herbicidal activity on weed plants in the presence of crop plants according to the following procedure.

Topsoil is sieved through a screen having 1.27 cm openings. In some of the tests the soil was mixed with fertilizer, while in other tests the fertilizer was omitted. This mixture is sterilized and then placed in pans having holes in the bottom. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered and the pans are then placed on a greenhouse bench and watered as needed. After the plants reach the desired stage, 10 to 14 days, 1 to 3 true leaf stage, each pan (except the control pans) is removed to a spraying chamber and sprayed by means of an atomizer, operating at a spray pressure of 170.3 kPa (10 psig) at the application rates noted in Table D. In the spray solution is an amount of an emulsifying agent mixture to give a spray solution or suspension which contains about 0.4% by volume of the emulsifier. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered from below and the injury to the plants as compared to the control pans is observed at approximately 10–14 days (usually 11 days) and in some instances observed again at 24–28 days (usually 25 days) after spraying. These latter observations are designated by a "pound" sign (#) following the column of example numbers in the Table.

In the following Table D the legends used to identify the plant species are the same as those used in the preceeding Table C.

TABLE D

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Pesw | Cocw |
|---|---|---|---|---|---|---|---|---|---|---|---|---|---|---|---|---|---|---|---|---|---|---|
| 2 | 5.6050 | 75 | | | 80 | 100 | 100 | 90 | | 100 | 70 | 10 | 99 | 100 | 70 | 90 | 100 | 100 | 100 | 95 | 100 | 99 |
| | 1.1210 | 60 | | | 50 | 95 | 85 | 75 | | 100 | 25 | 20 | 55 | 60 | 10 | 75 | 90 | N | 75 | 95 | 99 | 80 |
| | 0.2803 | 50 | | | 10 | 80 | 60 | 30 | | 60 | 10 | 5 | 35 | 55 | 5 | 20 | 70 | 10 | 60 | 45 | 90 | 50 |
| | 0.1401 | 10 | | | 0 | 75 | 25 | 20 | | 25 | 0 | 0 | 10 | 15 | 0 | 30 | 50 | 5 | 20 | 60 | 95 | 60 |
| | 0.0701 | 10 | | | 0 | 60 | 30 | 10 | | 30 | 0 | 0 | 10 | 40 | 0 | 5 | 10 | 5 | 20 | 35 | 50 | 25 |
| 1 | 5.6050 | 99 | 100 | | 80 | 99 | 100 | 99 | 100 | 100 | 40 | 50 | 75 | 80 | 75 | 99 | 100 | 100 | 100 | 100 | 100 | 100 |
| | 5.6050 | 95 | 75 | 80 | 70 | 100 | 100 | 100 | 99 | 100 | 35 | 35 | 40 | 80 | 75 | 90 | 100 | 99 | 95 | 95 | 90 | 95 |
| | 1.1210 | 50 | | 50 | 40 | 95 | 80 | 95 | | 100 | 20 | 10 | 30 | 60 | 35 | 60 | 80 | 95 | 75 | 70 | 75 | 65 |
| | 1.1210 | 60 | | | 65 | 95 | 80 | 80 | | 100 | 15 | 5 | 45 | 65 | 15 | 70 | 75 | 25 | 75 | 60 | 55 | 65 |
| | 0.5605 | 65 | | | 60 | 75 | 95 | 80 | | 95 | 10 | 0 | 25 | 45 | 0 | 10 | 70 | 20 | 95 | 40 | | |
| | 0.2803 | 50 | | 5 | 20 | 70 | 75 | 80 | | 90 | 5 | 0 | 30 | 25 | 5 | 35 | 25 | 85 | 70 | | | 35 |
| | 0.2803 | 10 | 75 | 0 | 25 | 85 | 70 | 99 | | 90 | 10 | 0 | 25 | 40 | 0 | 25 | 30 | 20 | 35 | 40 | 60 | 20 |
| | 0.1401 | 15 | 60 | | 30 | 70 | 70 | 70 | | 75 | 0 | 0 | 30 | 10 | 5 | 20 | 10 | 10 | 60 | 35 | 20 | 10 |
| | 0.0701 | 10 | | | 0 | 95 | 60 | 75 | 85 | 70 | 5 | 0 | 60 | 30 | 0 | 10 | 0 | 45 | 20 | 25 | 40 | |
| | 0.0701 | 5 | | 0 | N | 40 | 40 | 50 | | 50 | 0 | 0 | 10 | 5 | 5 | 20 | 10 | 0 | 10 | | | |
| | 0.0350 | 5 | | 0 | 10 | 20 | 35 | 30 | | 25 | 0 | 0 | 25 | 0 | 0 | 20 | 0 | 98 | 90 | | | |
| 3 | 5.6050 | 50 | 100 | 100 | 100 | 100 | 100 | 100 | | 100 | 25 | 50 | 99 | 90 | 50 | 90 | 98 | 99 | 100 | | | |
| | 1.1210 | 10 | 100 | 90 | 100 | 100 | 100 | 100 | 100 | 100 | 15 | 25 | 50 | 60 | 25 | 50 | 75 | 20 | 40 | | | |
| | 0.2803 | 25 | 100 | 50 | 100 | 80 | 75 | 98 | 80 | 99 | 10 | 10 | 25 | 30 | 20 | 20 | 5 | 10 | 30 | | | |
| | 0.0701 | 5 | 90 | 25 | 40 | 30 | 40 | 98 | 95 | 90 | 5 | 5 | 5 | 5 | 10 | 5 | 0 | 5 | 0 | | | |
| | 0.0175 | 0 | 70 | 20 | 30 | 20 | 30 | 75 | 65 | 50 | 5 | 0 | 5 | 0 | 0 | 0 | 0 | 0 | 0 | | | |
| | 0.0044 | 0 | 40 | 25 | 75 | 20 | 10 | 5 | 65 | 30 | 0 | 5 | 5 | 0 | 0 | 5 | 5 | 0 | 0 | | | |
| 4 | 11.2100 | 65 | 100 | 100 | 98 | 100 | 100 | 100 | | 90 | 20 | 25 | 30 | 65 | 10 | 30 | 60 | 98 | 40 | | | |
| | 5.6050 | 30 | 75 | 80 | 60 | 90 | 70 | 75 | | 75 | 10 | 10 | 30 | 50 | 10 | 25 | 60 | 95 | 50 | | | |
| | 1.1210 | 25 | 50 | 50 | 30 | 60 | 50 | 50 | | 30 | 0 | Z | 40 | 50 | 0 | 0 | 35 | 75 | 20 | | | |
| | 0.2803 | 5 | 35 | 5 | 25 | 40 | 30 | 30 | | 30 | 0 | 10 | 20 | 25 | 0 | 5 | 10 | 40 | 0 | | | |
| | 0.0701 | 0 | 20 | 0 | 5 | 25 | 10 | 30 | | 0 | 0 | 0 | 20 | 25 | 0 | 0 | 10 | 20 | 0 | | | |
| 5 | 5.6050 | 70 | 100 | 60 | 70 | 99 | 100 | 80 | 100 | 100 | 20 | 20 | 80 | 70 | 35 | 70 | 95 | 95 | 65 | | | |
| | 1.1210 | 70 | 95 | 10 | 60 | 80 | 75 | 75 | 100 | 70 | 5 | 15 | 45 | 50 | 20 | 40 | 40 | N | 40 | | | |
| | 0.5605 | 35 | 75 | 0 | 65 | 99 | 100 | 60 | 80 | 95 | 5 | 5 | 40 | 55 | 15 | 25 | 30 | 80 | 15 | | | |
| | 0.2803 | 50 | 35 | 0 | 40 | 75 | 70 | 20 | 95 | 35 | 0 | 0 | 40 | 40 | 0 | 40 | 30 | 50 | 20 | | | |
| | 0.1401 | 25 | 50 | 0 | 20 | 50 | 75 | 10 | 65 | 30 | 5 | 20 | 25 | 25 | 0 | 25 | 25 | 20 | 0 | | | |
| | 0.0701 | 10 | 45 | 0 | 5 | 75 | 10 | 15 | 65 | 20 | 0 | 0 | 30 | 40 | 0 | 10 | 0 | 0 | 25 | | | |
| 8 | 5.6050 | 70 | 100 | 100 | 100 | 100 | 100 | 100 | | 100 | 25 | 25 | 50 | 99 | 40 | 50 | 60 | 40 | 75 | | | |
| | 1.1210 | 50 | 100 | 98 | 100 | 70 | 70 | 98 | | 75 | 10 | 30 | 25 | 50 | 25 | 25 | 20 | 10 | 40 | | | |
| | 0.2803 | 10 | 70 | 50 | 65 | 70 | 30 | 75 | | 30 | 5 | 5 | 20 | 5 | 5 | 5 | 5 | 5 | 25 | | | |
| | 0.0701 | 5 | 25 | 20 | 25 | 30 | 30 | 50 | | 70 | 0 | 0 | 50 | 10 | 0 | 0 | 10 | 5 | 0 | | | |
| | 0.0044 | 5 | 20 | 10 | 40 | 20 | 25 | 60 | | 20 | 5 | 0 | 10 | 5 | 0 | 0 | 5 | 5 | 0 | | | |
| 10 | 5.6050 | 50 | 5 | 30 | 5 | 0 | 10 | 25 | | 25 | 0 | 0 | 10 | 5 | 20 | 10 | 35 | 75 | 65 | | | |
| | 1.1210 | 25 | 98 | 80 | 80 | 99 | 100 | 99 | | 99 | 35 | 70 | 30 | 70 | 80 | 95 | 99 | 100 | 99 | | 0 | |
| | 0.2803 | 5 | 25 | 10 | 50 | 80 | 75 | 90 | | 60 | 25 | 75 | 60 | 45 | 65 | 75 | 75 | 90 | 70 | | | |
| | 0.0701 | 5 | 20 | 10 | 35 | 40 | 55 | 60 | | 50 | 20 | 25 | 45 | 25 | 15 | 25 | 60 | 65 | 50 | | | |
| | 0.0175 | 5 | 10 | 10 | 10 | 25 | 30 | 35 | | 40 | 5 | 20 | 40 | 40 | 5 | 10 | 20 | 50 | 10 | | | |
| 12 | 5.6050 | 95 | 20 | 75 | 80 | 100 | 90 | 99 | | 100 | 30 | 0 | 98 | 75 | 5 | 95 | 99 | 100 | 0 | | | 75 |
| | 1.1210 | 70 | 100 | 35 | 50 | 95 | 75 | 90 | | 95 | 25 | 15 | 60 | 45 | 80 | 75 | 75 | 90 | 99 | | | 75 |
| | 0.2803 | 25 | 75 | 10 | 35 | 80 | 55 | 60 | | 75 | 20 | 5 | 45 | 25 | 65 | 25 | 60 | 65 | 70 | | | 70 |
| | 0.0701 | 25 | 65 | 10 | 20 | 35 | 30 | 10 | | 40 | 5 | 0 | 40 | 40 | 15 | 5 | 20 | 50 | 50 | | | 50 |
| | 0.0175 | 5 | 40 | 10 | 10 | 35 | 5 | 10 | | 30 | 0 | 0 | 10 | 20 | 5 | 5 | 10 | 10 | 0 | | | 0 |
| 15 | 5.6050 | 70 | 100 | 100 | 80 | 100 | 100 | 100 | | 100 | 30 | 15 | 98 | 75 | 70 | 95 | 100 | 99 | 100 | | | 95 |
| | 1.1210 | 35 | 100 | 98 | 60 | 100 | 100 | 99 | | 98 | 10 | 10 | 60 | 35 | 25 | 25 | 75 | 90 | 90 | | | 30 |

TABLE D-continued

| Ex. No. | Rate kg/ha | Sobe | Cotz | Rape | Cobu | Wibw | Mogl | Hese | Jiwc | Vele | Whez | Rice | Grso | Corn | Dobr | Prmi | Bygr | Lacg | Grft | Sube | Pesw | Cocw |
|---|---|---|---|---|---|---|---|---|---|---|---|---|---|---|---|---|---|---|---|---|---|---|
| | 0.2803 | 20 | 95 | 75 | 40 | 98 | 75 | 80 | | 60 | 5 | 10 | 30 | 10 | 5 | 10 | 60 | 80 | 50 | | | 5 |
| | 0.0701 | 10 | 60 | 5 | 20 | 75 | 75 | 65 | | 25 | 0 | 5 | 25 | 20 | 0 | 0 | 10 | 50 | 5 | | | 0 |
| | 0.0175 | 5 | 25 | 0 | 10 | 50 | 50 | 25 | | 10 | 0 | 0 | 20 | 30 | 0 | 0 | 5 | 5 | 0 | | | 0 |
| | 0.0044 | 0 | 0 | 0 | 0 | 30 | 20 | 0 | | 0 | 0 | 0 | 20 | 5 | 0 | 0 | 0 | 10 | 0 | | | 0 |
| 16 | 5.6050 | 80 | 100 | 100 | 98 | 100 | 100 | 99 | | 100 | 10 | 20 | 60 | 60 | 25 | 50 | 70 | 95 | 75 | | | 30 |
| | 1.1210 | 30 | 100 | 80 | 60 | 99 | 100 | 90 | | 99 | 5 | 20 | 25 | 40 | 10 | 25 | 5 | 80 | 35 | | | 20 |
| | 0.2803 | 20 | 75 | 40 | 25 | 75 | 90 | 75 | | 60 | 0 | 0 | 20 | 20 | 5 | 5 | 5 | 25 | 10 | | | 0 |
| | 0.0701 | 10 | 50 | 0 | 20 | 75 | 50 | 60 | | 25 | 0 | 0 | 5 | 25 | 0 | 0 | 10 | 30 | 0 | | | 0 |
| | 0.0175 | 0 | 20 | 0 | 5 | 30 | 10 | 35 | | 5 | 0 | 0 | 5 | 5 | 5 | 0 | 5 | 25 | 0 | | | 0 |
| | 0.0044 | 0 | 0 | 0 | 10 | 30 | 5 | 0 | | 5 | 0 | 0 | 5 | 5 | 0 | 0 | 0 | 5 | 0 | | | 0 |
| | 5.6050 | 85 | 100 | 60 | 75 | 99 | 95 | 99 | 100 | 100 | 40 | 10 | 99 | 90 | 70 | 60 | 100 | 99 | 100 | | | |
| | 1.1210 | 60 | 100 | 15 | 30 | 75 | 65 | 100 | 100 | 90 | 10 | 5 | 75 | 80 | 60 | 20 | 65 | 95 | 75 | | | |
| | 0.2803 | 15 | 60 | 0 | 5 | 70 | 50 | 70 | 90 | 70 | 5 | 5 | 50 | 20 | 5 | 10 | 75 | 75 | 60 | | | |
| | 0.0701 | 5 | 60 | 0 | 0 | 35 | 25 | 65 | 75 | 70 | 0 | 5 | 25 | 0 | 0 | 0 | 30 | 55 | 25 | | | |
| | 0.0175 | 0 | 20 | 0 | 0 | 35 | 5 | 20 | 100 | 5 | 0 | 0 | 5 | 0 | 0 | 0 | 30 | 50 | 0 | | | |
| 19 | 5.6050 | 75 | 90 | 90 | 95 | 100 | 95 | 99 | 100 | 100 | 50 | 30 | 99 | 95 | 75 | 80 | 100 | 100 | 100 | | | |
| | 1.1210 | 60 | 90 | 70 | 65 | 99 | 65 | 95 | 100 | 95 | 15 | 10 | 75 | 85 | 60 | 40 | 95 | 95 | 95 | | | |
| | 0.2803 | 15 | 85 | 30 | 35 | 65 | 50 | 75 | 90 | 35 | 5 | 5 | 35 | 90 | 5 | 20 | 75 | 75 | 60 | | | |
| | 0.0701 | 5 | 40 | 0 | 0 | 55 | 25 | 75 | 75 | 30 | 0 | 5 | 25 | 5 | 0 | 10 | 30 | 70 | 50 | | | |
| | 0.0175 | 0 | 10 | 0 | 0 | 65 | 20 | 80 | 65 | N | 0 | 5 | 20 | 5 | 0 | 0 | 30 | 50 | 100 | | | |
| 20 | 5.6050 | 70 | 100 | 90 | 100 | 100 | 100 | 100 | 100 | 100 | 45 | 60 | 99 | 95 | 75 | 65 | 100 | 100 | 100 | | | |
| | 1.1210 | 15 | 100 | 65 | 95 | 70 | 95 | 100 | 100 | 100 | 15 | 10 | 85 | 75 | 10 | 10 | 85 | 75 | 85 | | | |
| | 0.2803 | 10 | 85 | 30 | 95 | 35 | 80 | 100 | 100 | 100 | 5 | 0 | 65 | 15 | 0 | 0 | 55 | 50 | 45 | | | |
| | 0.0701 | 10 | 50 | 0 | 60 | 10 | 60 | 70 | 65 | 50 | 5 | 0 | 20 | 0 | 0 | 0 | 10 | 20 | 10 | | | |
| | 0.0175 | 5 | 50 | 10 | 50 | 0 | 50 | 35 | 70 | 40 | 25 | 0 | 30 | 0 | 0 | 0 | 10 | 10 | 10 | | | |
| 22 | 5.6050 | 90 | 95 | 100 | 80 | 95 | 85 | 99 | | 95 | 25 | 45 | 40 | 90 | 20 | 40 | 95 | 65 | 70 | | | |
| | 1.1210 | 90 | 95 | 90 | 70 | 75 | 95 | 90 | | 99 | 30 | 15 | 50 | 60 | 25 | 45 | 60 | 75 | 65 | | | |
| | 0.2803 | 60 | 90 | 85 | 60 | 75 | 75 | 85 | | 75 | 20 | 35 | 30 | 70 | 35 | 50 | 70 | 65 | 35 | | | |
| | 0.0701 | 35 | 90 | 25 | 60 | 75 | 60 | 75 | | 60 | 15 | 20 | 25 | 25 | 15 | 30 | 10 | 75 | 45 | | | |
| | 0.0175 | 15 | 75 | 5 | 60 | 40 | 25 | 60 | | 50 | 10 | 15 | 20 | 30 | 10 | 15 | 15 | 10 | 20 | | | |
| | 0.0044 | 10 | 30 | 0 | 35 | 15 | 10 | 40 | | 20 | 0 | 20 | 10 | 25 | 0 | 10 | 5 | 10 | 10 | | | |
| 24 | 5.6050 | 45 | | | 70 | 100 | 100 | 85 | | 100 | 60 | 10 | 70 | 95 | 75 | 70 | 95 | 100 | 99 | | | |
| | 1.1210 | 20 | | | 40 | 100 | 99 | 60 | | 30 | N | 0 | 25 | 70 | 10 | 35 | 60 | 95 | 70 | | | 60 |
| | 0.5605 | 10 | | | 25 | 80 | 75 | 35 | | 20 | 0 | 0 | 15 | 30 | 0 | 30 | 40 | 40 | 60 | | | 60 |
| | 0.2803 | 10 | | | 10 | 60 | 85 | 60 | | 10 | 0 | 0 | 35 | 60 | 10 | 20 | 20 | 30 | 50 | | | 0 |
| | 0.1401 | 5 | | | 10 | 60 | 75 | 10 | | 5 | N | 0 | 10 | 25 | 10 | 20 | 10 | 10 | 15 | | | 0 |
| | 0.0701 | 5 | | | 5 | 30 | 15 | 0 | | 0 | 0 | 0 | 15 | 0 | 0 | 10 | 10 | 5 | 0 | | | |
| 25 | 5.6050 | 75 | 95 | 50 | 70 | 100 | 90 | 99 | | 100 | 40 | 35 | 85 | 95 | 65 | 90 | 95 | 99 | 95 | 99 | 100 | 40 |
| | 1.1210 | 35 | 60 | 25 | 45 | 80 | 75 | 80 | | 90 | 30 | 25 | 60 | 75 | 60 | 45 | 80 | 90 | 75 | 75 | 100 | 35 |
| | 0.2803 | 10 | 35 | 30 | 40 | 50 | 20 | 50 | | 60 | 5 | 10 | 40 | 30 | 10 | 15 | 40 | 70 | 35 | 75 | 75 | 20 |
| | 0.0701 | 5 | 15 | 0 | 10 | 15 | 10 | 15 | | 20 | 10 | 5 | 30 | 10 | 5 | 5 | 65 | 20 | 10 | N | 90 | 0 |
| | 0.0175 | 5 | 20 | 0 | 5 | 10 | 15 | 30 | 5 | 10 | 10 | 20 | 20 | 10 | 0 | 35 | 50 | 10 | 0 | 90 | 75 | 0 |
| 26 | 5.6050 | 65 | 100 | 98 | 80 | 100 | 98 | 99 | 0 | 99 | 10 | 20 | 60 | 50 | 35 | 20 | 35 | 98 | 75 | 75 | 50 | |
| | 1.1210 | 40 | 65 | 75 | 25 | 75 | 90 | 80 | 0 | 90 | 10 | 10 | 30 | 70 | 25 | 5 | 10 | 70 | 35 | | | |
| | 0.2803 | 15 | 35 | 40 | 30 | 60 | 40 | 65 | 5 | 20 | 10 | 5 | 20 | 10 | 20 | 35 | 10 | 30 | 20 | | | |
| | 0.0701 | 5 | 5 | 0 | 20 | 30 | 25 | 30 | 0 | 10 | 0 | 20 | 5 | 15 | 0 | 20 | 5 | 25 | 5 | | | |
| | 0.0175 | 0 | 0 | 0 | 25 | 20 | 5 | 25 | 0 | 10 | 0 | 10 | 10 | 5 | 0 | 0 | 5 | 10 | 0 | | | |
| 27 | 5.6050 | 5 | 25 | 0 | 0 | 0 | 0 | N | | 0 | 5 | 40 | 10 | 10 | 0 | 10 | 5 | 0 | 0 | | | |
| | 1.1210 | 5 | 0 | 10 | 0 | 0 | 0 | 10 | 0 | 0 | 0 | 10 | 5 | 15 | 0 | 0 | 5 | 0 | 0 | | | |
| | 0.2803 | 5 | 0 | 0 | 0 | 0 | 0 | 0 | 0 | 0 | 0 | 0 | 5 | 5 | 0 | 0 | 5 | 0 | 0 | | | |
| | 0.0701 | 0 | 0 | 0 | 0 | 0 | 0 | 20 | 5 | 0 | 0 | 0 | 0 | 0 | 0 | 0 | 0 | 0 | 0 | | | |

TABLE D-continued

| Ex. No. | Rate kg/ha | Sobe | Cotz | Rape | Cobu | Wibw | Mogl | Hese | Jiwe | Vele | Whcz | Rice | Grso | Corn | Dobr | Prmi | Bygr | Lacg | Grft | Sube | Pesw | Cocw |
|---|---|---|---|---|---|---|---|---|---|---|---|---|---|---|---|---|---|---|---|---|---|---|
| 29 | 0.0175 | 5 | 0 | 0 | 0 | 0 | 5 | 10 | 0 | 0 | 0 | 10 | 15 | 5 | 0 | 0 | 5 | 10 | 5 | | | |
| | 5.6050 | 90 | 95 | 10 | 40 | 99 | 95 | 75 | 100 | 100 | 15 | 25 | 40 | 50 | 10 | 70 | 25 | 20 | 50 | | | |
| | 1.1210 | 50 | 65 | 0 | 10 | 40 | 75 | 45 | 100 | 60 | 10 | 10 | 25 | 50 | 5 | 25 | 5 | 5 | 15 | | | |
| | 0.2803 | 15 | 25 | 0 | 10 | 60 | 50 | 30 | 75 | 20 | 5 | 0 | 20 | 30 | 0 | 15 | 0 | 10 | 5 | | | 80 |
| | 0.0701 | 0 | 10 | 0 | 0 | 0 | 0 | 5 | 10 | 5 | 0 | 0 | 5 | 0 | 0 | 5 | 0 | 0 | 5 | | | |
| 30 | 5.6050 | 80 | 90 | 99 | 75 | 100 | 95 | 95 | | 100 | 30 | 60 | 90 | 95 | 60 | 75 | 99 | 100 | 99 | | | |
| | 1.1210 | 20 | 95 | 35 | 40 | 70 | 80 | 75 | | 70 | 15 | 20 | 30 | 30 | 10 | 20 | 65 | 35 | 60 | | 40 | 20 |
| | 0.2803 | 10 | 65 | 5 | 30 | 75 | 30 | 55 | | 60 | 5 | 15 | 25 | 10 | 10 | 10 | 20 | 50 | 15 | | | 0 |
| | 0.0701 | 10 | 45 | 0 | 10 | 20 | 60 | 5 | | 35 | 5 | 5 | 30 | 25 | 5 | 5 | 5 | 5 | 10 | | | 20 |
| | 0.0175 | 5 | 15 | Z | 5 | 25 | 40 | 5 | | 5 | 0 | 10 | Z | 5 | 0 | 0 | 0 | 0 | 0 | | | |
| 34 | 5.6050 | 90 | 99 | 80 | 90 | 100 | 95 | 99 | 100 | 100 | 50 | 30 | 95 | 100 | 100 | 100 | 100 | 100 | 100 | | | 100 |
| | 1.1210 | 80 | 99 | 30 | 100 | 100 | 95 | 95 | 100 | 100 | 20 | 70 | 90 | 75 | 25 | 80 | 95 | 100 | 99 | | | 90 |
| | 0.2803 | 80 | 75 | 20 | 60 | 100 | 95 | 80 | 100 | 70 | 15 | 30 | 75 | 75 | 0 | 30 | 75 | 80 | 100 | | | 50 |
| | 0.0701 | 30 | 60 | 10 | 20 | 70 | 30 | 60 | 90 | 50 | 0 | 30 | 30 | 0 | 0 | 30 | 50 | 75 | 80 | | | 10 |
| | 0.0175 | 30 | 65 | 0 | 20 | 10 | 20 | 0 | | 20 | 0 | 5 | 10 | 0 | 5 | 5 | 30 | 0 | 20 | | | 0 |
| 35 | 5.6050 | 90 | 90 | 95 | 100 | 100 | 95 | 100 | | 75 | 60 | 10 | 75 | 85 | 35 | 80 | 95 | 85 | 90 | | | 70 |
| | 1.1210 | 60 | 95 | 60 | 80 | 90 | 80 | 95 | | 60 | 20 | 5 | 65 | 90 | 10 | 50 | 75 | 80 | 75 | | | 20 |
| | 0.2803 | 30 | 90 | 20 | 60 | 70 | 80 | 100 | | 75 | 10 | 5 | 40 | 50 | 0 | 10 | 30 | 70 | 40 | | | 0 |
| | 0.0701 | 30 | 65 | 10 | 30 | 10 | 30 | 80 | | 60 | 5 | 5 | 50 | 70 | 0 | 30 | 10 | 10 | 40 | | | 0 |
| | 0.0175 | 25 | 65 | 10 | 20 | 0 | 20 | 50 | | 20 | 0 | 0 | 10 | 40 | 0 | 5 | 5 | 0 | 10 | | | 0 |
| 36 | 5.6050 | 50 | 90 | 40 | 85 | 95 | 100 | 100 | | 75 | 20 | 10 | 75 | 85 | 35 | 80 | 95 | 95 | 90 | | | 70 |
| | 1.1210 | 50 | 80 | 10 | 30 | 75 | 80 | 75 | | 65 | 10 | 5 | 65 | 90 | 10 | 50 | 75 | 80 | 75 | | | 20 |
| | 0.2803 | 10 | 65 | 10 | 75 | 20 | 80 | 75 | | 55 | 5 | 5 | 40 | 50 | 10 | 10 | 30 | 70 | 40 | | | 0 |
| | 0.0701 | 5 | 70 | 5 | 30 | 10 | 30 | 35 | | 10 | 0 | 0 | 5 | 40 | 0 | 10 | 10 | 10 | 10 | | | 0 |
| | 0.0175 | 5 | 20 | 5 | 10 | 10 | 20 | 0 | | 0 | 0 | 0 | 0 | 0 | 0 | 0 | 0 | 0 | 0 | | | 0 |
| 37 | 5.6050 | 80 | 95 | 45 | 95 | 100 | 100 | 100 | | 100 | 50 | 50 | 98 | 99 | 95 | 95 | 100 | 100 | 100 | | | 100 |
| | 1.1210 | 55 | 80 | 20 | 70 | 75 | 75 | 95 | | 75 | 20 | 10 | 75 | 80 | 30 | 70 | 85 | 80 | 85 | | | 85 |
| | 0.2803 | 30 | 50 | 10 | 70 | 40 | 80 | 75 | | 50 | 5 | 5 | 50 | 60 | 10 | 20 | 60 | 75 | 60 | | | 65 |
| | 0.0701 | 10 | 30 | 5 | 10 | 0 | 60 | 40 | | 25 | 0 | 0 | 10 | 40 | 0 | 5 | 20 | 40 | 20 | | | 10 |
| | 0.0175 | 10 | 20 | 0 | 5 | 0 | 5 | 5 | | 0 | 0 | 0 | 5 | 25 | 0 | 0 | 5 | 0 | 0 | | | 10 |
| 38 | 5.6050 | 95 | 100 | 85 | 85 | 100 | 100 | 100 | | 100 | 30 | 10 | 85 | 95 | 95 | 95 | 95 | 100 | 100 | | | 50 |
| | 1.1210 | 80 | 100 | 95 | 75 | 75 | 90 | 95 | | 90 | 20 | 30 | 75 | 80 | 30 | 70 | 80 | 85 | 85 | | | 30 |
| | 0.2803 | 65 | 85 | 35 | 40 | 50 | 70 | 70 | | 60 | 10 | 5 | 75 | 60 | 20 | 20 | 70 | 75 | 80 | | | 15 |
| | 0.0701 | 15 | 60 | 20 | 10 | 40 | 30 | 75 | | 40 | 5 | N | 20 | 40 | 10 | 10 | 10 | 40 | 10 | | | 0 |
| | 0.0175 | 5 | 25 | 10 | 10 | 20 | 30 | N | | 25 | 0 | 5 | 10 | 10 | 0 | 0 | 10 | 0 | 10 | | | 0 |
| 39 | 5.6050 | 98 | 99 | 95 | 75 | 100 | 100 | 100 | | 100 | 25 | 75 | 95 | 100 | 70 | 90 | 100 | 99 | 100 | | | 75 |
| | 1.1210 | 40 | 99 | 50 | 50 | 80 | 95 | 99 | | 98 | 10 | 5 | 50 | 75 | 30 | 10 | 80 | 80 | 75 | | | 25 |
| | 0.2803 | 20 | 100 | 25 | 40 | 70 | 80 | 75 | | 70 | 5 | 10 | 25 | 50 | 5 | 10 | 30 | 30 | 70 | | | 5 |
| | 0.0701 | 5 | 60 | 0 | 25 | 50 | 10 | 65 | | 40 | 0 | 0 | 25 | 10 | 5 | 5 | 20 | 20 | 10 | | | 0 |
| | 0.0175 | 5 | 10 | 0 | 10 | 0 | 5 | 5 | | 30 | 0 | 0 | 10 | 25 | 0 | 0 | 5 | 5 | 0 | | | 0 |
| 40 | 5.6050 | 50 | 100 | 85 | 50 | 80 | 100 | 90 | | 75 | 15 | 10 | 85 | 40 | 10 | 75 | 95 | 60 | 90 | | | 30 |
| | 1.1210 | 60 | 75 | 75 | 75 | 75 | 100 | 70 | | 65 | 5 | 30 | 75 | 65 | 70 | 95 | 80 | 40 | 50 | | | 20 |
| | 0.2803 | 20 | 95 | 50 | 40 | 50 | 70 | 75 | | 40 | 5 | 5 | 20 | 25 | 30 | 50 | 70 | 25 | 25 | | | 10 |
| | 0.0701 | 10 | 35 | 25 | 10 | 40 | 40 | N | | 25 | 5 | N | 10 | 30 | 10 | 10 | 10 | 40 | 10 | | | 5 |
| | 0.0175 | 5 | 10 | 10 | 10 | 10 | 30 | 100 | | 100 | 0 | 75 | 10 | 40 | 5 | Z | 5 | 0 | 10 | | | 0 |
| 41 | 5.6050 | 60 | 100 | 75 | 50 | 90 | 100 | 100 | | 100 | 25 | 5 | 25 | 100 | 5 | 90 | 100 | 99 | 100 | | | 75 |
| | 1.1210 | 25 | 99 | 75 | 50 | 70 | 95 | 99 | | 80 | 10 | 10 | 25 | 50 | 0 | 10 | 80 | 50 | 70 | | | 25 |
| | 0.2803 | 10 | 100 | 50 | 40 | 50 | 70 | 75 | | 40 | 5 | 10 | 25 | 30 | 5 | 5 | 60 | 40 | 70 | | | 5 |
| | 0.0701 | 10 | 95 | 25 | 10 | 40 | 40 | 95 | | 25 | 5 | 0 | 20 | 60 | 0 | 5 | 30 | 25 | 10 | | | 0 |
| | 0.0175 | 10 | 15 | 5 | 10 | 10 | 10 | 75 | | 100 | 0 | 5 | 5 | 30 | 0 | 5 | 5 | 40 | 10 | | | 30 |
| 42 | 11.2100 | 100 | 100 | 95 | 90 | 95 | 100 | 95 | | 100 | 10 | 100 | 40 | 50 | 25 | 40 | 100 | 99 | 80 | | | 20 |
| | 5.6050 | 70 | 100 | 70 | 60 | 90 | 100 | 90 | | 80 | 5 | 0 | 25 | 60 | 25 | 5 | 40 | 50 | 50 | | | 10 |
| | 1.1210 | 30 | 60 | 25 | 30 | 70 | 95 | 50 | | 98 | 5 | 5 | 25 | 60 | 5 | 5 | 20 | 40 | 20 | | | 0 |

TABLE D-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Pesw | Cocw |
|---|---|---|---|---|---|---|---|---|---|---|---|---|---|---|---|---|---|---|---|---|---|---|
| 43 | 0.2803 | 20 | 75 | 5 | 25 | 50 | 75 | 40 | | 75 | 0 | 5 | 25 | 5 | 0 | 5 | 10 | 30 | 5 | | | 0 |
|  | 11.2100 | 50 | 95 | 60 | 50 | 99 | 100 | 75 | | 100 | 10 | 10 | 50 | 25 | 25 | 25 | 70 | 95 | 75 | | | 10 |
|  | 5.6050 | 20 | 75 | 70 | 50 | 95 | 100 | 65 | | 50 | 5 | 5 | 35 | 60 | 20 | 25 | 40 | 90 | 50 | | | 5 |
|  | 1.1210 | 10 | 60 | 20 | 25 | 80 | 65 | 30 | | 60 | 0 | 5 | 30 | 40 | 5 | 5 | 25 | 70 | 25 | | | 0 |
|  | 0.2803 | 5 | 60 | 5 | 50 | 60 | 90 | 50 | | 60 | 5 | 0 | 20 | 25 | 0 | 0 | 20 | 20 | 20 | | | 0 |
| 44 | 5.6050 | 20 | 80 | 70 | 50 | 75 | 98 | 65 | | 60 | 0 | 75 | 25 | 65 | 10 | 40 | 35 | 75 | 40 | | | 0 |
|  | 1.1210 | 5 | 25 | 5 | 20 | 5 | 70 | 20 | | 10 | 0 | 20 | 10 | 60 | 0 | 0 | 20 | 10 | 5 | | | 95 |
|  | 0.2803 | 0 | 20 | 0 | 10 | 0 | 0 | 0 | | 0 | 0 | N | 20 | 25 | 0 | 0 | 10 | 0 | 0 | | | 0 |
|  | 0.0175 | 0 | N | 30 | 0 | 0 | 0 | 0 | | 0 | 0 | 10 | 0 | 5 | 0 | 0 | 20 | 0 | 0 | | | 0 |
| 45 | 5.6050 | 25 | 100 | 100 | 100 | 98 | 100 | 100 | | 100 | 20 | 75 | 80 | 70 | 30 | 75 | 90 | 75 | 100 | | | 80 |
|  | 1.1210 | 35 | 100 | 100 | 100 | 75 | 100 | 100 | | 100 | 10 | 20 | 70 | 75 | 5 | 30 | 80 | 30 | 80 | | | 10 |
|  | 0.2803 | 10 | 70 | 50 | 100 | 75 | 100 | 100 | | 80 | 5 | 25 | 40 | 75 | 0 | 20 | 70 | 35 | 40 | | | 0 |
|  | 0.0701 | 5 | 70 | 0 | 100 | 70 | 75 | 70 | | 65 | 5 | 10 | 25 | 60 | 0 | 10 | 35 | 30 | 35 | | | 0 |
|  | 0.0175 | 10 | 30 | 5 | 65 | 40 | 50 | 65 | | 60 | 5 | N | 25 | 35 | 0 | 5 | 25 | 30 | 20 | | | N |
| 46 | 5.6050 | 80 | 100 | 100 | 99 | 100 | 100 | 100 | | 100 | 25 | 99 | 80 | 65 | 40 | 75 | 90 | 100 | 100 | | | 75 |
|  | 1.1210 | 80 | 100 | 100 | 100 | 98 | 100 | 100 | | 100 | 20 | 95 | 70 | 65 | 25 | 80 | 90 | 98 | 100 | | | 98 |
|  | 0.2803 | 70 | 75 | 80 | 75 | 90 | 90 | 99 | | 95 | 10 | 10 | 25 | 40 | 10 | 25 | 25 | 40 | 60 | | | 35 |
|  | 0.0701 | 20 | 70 | 60 | 60 | 60 | 75 | 80 | | 75 | 5 | 5 | 25 | 25 | 5 | 10 | 5 | 50 | 35 | | | 0 |
|  | 0.0175 | 10 | 30 | 20 | 35 | 35 | 75 | 75 | | 60 | 0 | 5 | 35 | 35 | 0 | 5 | 5 | 30 | 5 | | | 0 |
| 47 | 5.6050 | 99 | 100 | 100 | 99 | 100 | 99 | 100 | | 100 | 25 | 25 | 95 | 95 | 98 | 99 | 100 | 100 | 100 | | | 98 |
|  | 1.1210 | 95 | 70 | 90 | 70 | 99 | 100 | 99 | | 100 | 15 | 20 | 70 | 70 | 40 | 75 | 99 | 99 | 98 | | | 60 |
|  | 0.2803 | 50 | 80 | 60 | 40 | 98 | 95 | 80 | | 100 | 5 | 5 | 20 | 50 | 25 | 35 | 90 | 90 | 40 | | | 50 |
|  | 0.0701 | 20 | 75 | 20 | 35 | 75 | 95 | 80 | | 98 | 5 | 5 | 20 | 75 | 10 | 30 | 30 | 50 | 10 | | | 20 |
|  | 0.0175 | 5 | 40 | 0 | 20 | 35 | 40 | 75 | | 60 | 0 | 0 | 20 | 50 | 5 | 20 | 10 | 40 | 0 | | | 0 |
| 48 | 5.6050 | 50 | 98 | 60 | 100 | 100 | 100 | 99 | | 99 | 20 | 35 | 75 | 95 | 90 | 95 | 99 | 99 | 100 | | | 75 |
|  | 1.1210 | 20 | 75 | 10 | 100 | 98 | 98 | 60 | | 75 | 5 | 5 | 35 | 65 | 10 | 50 | 80 | 90 | 95 | | | 25 |
|  | 0.2803 | 10 | 50 | 0 | 50 | 65 | 95 | 50 | | 50 | 10 | 5 | 25 | 25 | 25 | 20 | 25 | 35 | 35 | | | 10 |
|  | 0.0701 | 5 | 25 | 0 | 20 | 25 | 20 | 20 | | 25 | 0 | 0 | 10 | 35 | 10 | 5 | 5 | 20 | 0 | | | 0 |
|  | 0.0175 | 0 | 5 | 0 | 10 | 5 | 0 | 20 | | 20 | 5 | 0 | 5 | 10 | 5 | 0 | 5 | 5 | 0 | | | 0 |
| 49 | 5.6050 | 20 | 70 | 10 | 50 | 75 | 60 | 80 | | 70 | 10 | 10 | 35 | 60 | 25 | 20 | 70 | 80 | 75 | | | 20 |
|  | 1.1210 | 15 | 80 | 5 | 50 | 80 | 98 | 75 | | 60 | 0 | 25 | 30 | 25 | 20 | 25 | 60 | 80 | 65 | | | 10 |
|  | 0.2803 | 10 | 80 | 5 | 35 | 75 | 95 | 75 | | 40 | 10 | 0 | 25 | 70 | 10 | 10 | 30 | 80 | 50 | | | 5 |
|  | 0.0701 | 5 | 40 | 0 | 25 | 40 | 60 | 50 | | 30 | 0 | 0 | 20 | 50 | 5 | 0 | 20 | 50 | 25 | | | 0 |
|  | 0.0175 | 0 | 25 | 5 | 10 | 0 | 10 | 25 | | 40 | 10 | 20 | 10 | 40 | 5 | 0 | 10 | 20 | 0 | | | 0 |
| 50 | 5.6050 | 75 | 80 | 80 | 80 | 100 | 100 | 98 | | 100 | 0 | 0 | 65 | 65 | 35 | 75 | 80 | 99 | 80 | | | 50 |
|  | 1.1210 | 25 | 75 | 35 | 50 | 75 | N | 80 | | 98 | 20 | 20 | 50 | 40 | 10 | 20 | 35 | 60 | 30 | | | 10 |
|  | 0.2803 | 20 | 70 | 30 | 25 | 70 | 70 | 75 | | 80 | 5 | 5 | 40 | 35 | 5 | 5 | 25 | 70 | 25 | | | 0 |
| 52 | 5.6050 | 40 | 100 | 100 | 100 | 100 | 100 | 100 | | 100 | 10 | 30 | 70 | 60 | 10 | 20 | 70 | 40 | 60 | | | 98 |
|  | 1.1210 | 30 | 75 | 75 | 100 | 75 | 95 | 100 | | 75 | 5 | 10 | 30 | 20 | 5 | 5 | 50 | 25 | 40 | | | 75 |
|  | 0.2803 | 10 | 60 | 40 | 50 | 50 | 75 | 100 | | 75 | 0 | 5 | 25 | 10 | 5 | 5 | 10 | 25 | 40 | | | 25 |
|  | 0.0701 | 5 | 25 | 25 | 10 | 20 | 70 | 75 | | 40 | 10 | 20 | 5 | 10 | 0 | 5 | 5 | 5 | 0 | | | 5 |
|  | 0.0175 | 5 | 5 | 10 | 5 | 5 | 5 | 35 | | 25 | 5 | 0 | 5 | 10 | 0 | 0 | 5 | 5 | 0 | | | 0 |
| 53 | 5.6050 | 50 | 100 | 90 | 95 | 100 | 100 | 100 | | 98 | 25 | 15 | 80 | 60 | 25 | 25 | 20 | 50 | 30 | | | 50 |
|  | 1.1210 | 40 | 99 | 40 | 80 | 90 | 95 | 99 | | 75 | 10 | 0 | 40 | 20 | 0 | 5 | 10 | 25 | 35 | | | 10 |
|  | 0.2803 | 20 | 60 | 25 | 35 | 50 | 75 | 90 | | 40 | 5 | 20 | 5 | 30 | 20 | 40 | 10 | 10 | 35 | | | 0 |
|  | 0.0701 | 5 | 25 | 10 | 10 | 20 | 70 | 35 | | 40 | 20 | 0 | 20 | 10 | 0 | 5 | 10 | 95 | 10 | | | 30 |
| 54 | 5.6050 | 70 | 95 | 90 | 95 | 100 | 100 | 99 | | 98 | 5 | 15 | 80 | 60 | 30 | 70 | 80 | 95 | 80 | | | 65 |
|  | 1.1210 | 60 | 99 | 60 | 60 | 90 | 100 | 99 | | 75 | 10 | 10 | 40 | 80 | 10 | 65 | 60 | 80 | 70 | | | 50 |
|  | 0.2803 | 25 | 50 | 35 | 10 | 75 | 100 | 80 | | 50 | 5 | 5 | 25 | 35 | 5 | 20 | 20 | 50 | 40 | | | 5 |

TABLE D-continued

| Ex. No. | Rate kg/ha | Sobe | Cotz | Rape | Cobu | Wibw | Mogl | Hese | Jiwe | Vele | Whcz | Rice | Grso | Corn | Dohr | Prmi | Bygr | Lacg | Grft | Sube | Pesw | Cocw |
|---|---|---|---|---|---|---|---|---|---|---|---|---|---|---|---|---|---|---|---|---|---|---|
| 55 | 0.0701 | 10 | 65 | 25 | 20 | 30 | 70 | 70 |  | 20 | 0 | 0 | 10 | 20 | 0 | 5 | 10 | 25 | 25 |  |  | 0 |
|    | 5.6050 | 95 | 100 | 99 | 60 | N | 100 | 100 |  | 100 | 20 | 75 | 60 | 40 | 35 | 60 | 60 | 98 | 80 |  |  | 99 |
|    | 1.1210 | 70 | 100 | 75 | 35 | 100 | 100 | N |  | 75 | 5 | 70 | 40 | 50 | 10 | 60 | 25 | 80 | 50 |  |  | 65 |
|    | 0.2803 | 30 | 70 | 40 | 30 | 90 | 100 | 90 |  | 50 | 5 | 40 | 25 | 50 | 0 | 25 | 25 | 75 | 25 |  |  | 10 |
|    | 0.0701 | 30 | 65 | 25 | 25 | N | 70 | 70 |  | 40 | 0 | N | 25 | 50 | 0 | 35 | 25 | 75 | 25 |  |  | 0 |
| 56 | 11.2100 | 95 | 100 | 100 | 60 | 100 | 100 | N |  | 80 | 10 | 60 | 50 | 60 | 25 | 75 | 60 | 98 | 70 |  |  | 70 |
|    | 5.6050 | 40 | 100 | 75 | 30 | 95 | 100 | 95 |  | 60 | 5 | 80 | 25 | 35 | 20 | 60 | 30 | 65 | 25 |  |  | 60 |
|    | 1.1210 | 50 | 90 | 75 | 30 | 80 | 99 | 75 |  | 60 | 10 | 50 | 60 | 50 | 0 | 40 | 25 | 75 | 25 |  |  | 50 |
|    | 0.2803 | 40 | 75 | 75 | 25 | N | 95 | 75 |  | N | 5 | 20 | 25 | 30 | 30 | 20 | 20 | N | 35 |  |  | 0 |
| 57 | 5.6050 | 65 | 100 | 100 | 100 | 100 | 100 | 100 |  | 100 | 25 | 20 | 90 | 99 | 25 | 70 | 99 | 95 | 100 |  |  | 20 |
|    | 1.1210 | 35 | 99 | 100 | 75 | 95 | 100 | 95 |  | 90 | 10 | 20 | 75 | 40 | 10 | 40 | 80 | 90 | 80 |  |  | 50 |
|    | 0.2803 | 20 | 75 | 80 | 50 | 75 | 80 | 75 |  | 65 | 10 | 10 | 35 | 60 | 0 | 10 | 60 | 70 | 40 |  |  | 0 |
|    | 0.0701 | 5 | 75 | 30 | 25 | 40 | 75 | 60 |  | 50 | 0 | 5 | 25 | 25 | 0 | 0 | 25 | 20 | 25 |  |  | 0 |
|    | 0.0175 | 0 | 20 | 10 | 10 | 20 | 10 | 50 |  | 30 | 0 | 0 | 5 | 25 | 0 | 0 | 20 | 35 | 20 |  |  | 0 |
| 60 | 5.6050 | 25 |  |  |  |  |  |  |  |  | 5 |  |  |  |  |  |  |  |  |  |  |  |
|    | 5.6050 |  | 10 | 10 | 80 | 0 | 5 | 90 | 60 | 90 | 10 |  |  |  |  |  |  |  |  |  |  |  |
|    | 1.1210 |  | 10 | 10 | 60 | 5 | 5 | 40 | 20 | 70 | 10 |  |  |  |  |  |  |  |  |  |  |  |
|    | 0.2803 | 25 |  |  |  |  |  |  |  |  | 5 |  |  |  |  |  |  |  |  |  |  |  |
|    | 0.2803 | 5 | 10 | 55 | 30 | 5 | 5 | 5 | 5 | 35 | 10 |  |  |  |  |  |  |  |  |  |  |  |
|    | 0.0701 |  | 10 | 10 | 30 | 0 | 5 | 25 | 0 |  | 5 |  |  |  |  |  |  |  |  |  |  |  |
|    | 0.0175 | 0 | 0 | 0 | 20 | 5 | 5 | 20 | 5 | 25 | 5 |  |  |  |  |  |  |  |  |  |  |  |
|    | 0.0175 | 0 |  | 15 |  | 0 | 5 | 0 | 0 |  | 5 |  |  |  |  |  |  |  |  |  |  |  |
| 61 | 5.6050 | 20 |  | 0 | 20 | 5 | 5 | 0 | 5 | 5 | 5 |  |  |  |  |  |  |  |  |  |  |  |
|    | 1.1210 |  | 10 | 60 | 80 | 0 | 5 | 10 | 90 | 95 | 10 |  |  |  |  |  |  |  |  |  |  |  |
|    | 0.2803 |  | 10 | 10 | 50 | 5 | 5 | 40 | 30 | 75 | 10 |  |  |  |  |  |  |  |  |  |  |  |
|    | 0.2803 | 10 |  | 5 |  | 5 | 5 | 15 |  |  | 5 |  |  |  |  |  |  |  |  |  |  |  |
|    | 0.0701 | 0 |  | 20 |  | 0 | 5 | 0 |  |  | 5 |  |  |  |  |  |  |  |  |  |  |  |
| 62 | 0.2803 |  | 10 | 10 | 30 | 0 | 5 | 50 | 10 | 70 | 10 |  |  |  |  |  |  |  |  |  |  |  |
|    | 0.0701 |  | 10 | 10 | 25 | 5 | 5 | 10 | 0 | 30 | 5 |  |  |  |  |  |  |  |  |  |  |  |
|    | 0.0701 | 0 |  | 10 | 95 | 0 | 5 | 0 | 65 | 95 | 10 |  |  |  |  |  |  |  |  |  |  |  |
|    | 5.6050 | 25 |  |  |  |  |  |  |  |  | 5 |  |  |  |  |  |  |  |  |  |  |  |
| 64 | 5.6050 | 75 | 100 | 95 | 65 | 100 | 100 | 100 | 10 | 30 | 40 | 40 | 35 | 100 | 80 | 60 | 75 | 99 | 99 |  |  | 75 |
|    | 1.1210 | 65 | 100 | 65 | 80 | 98 | 100 | 100 |  | 100 | 40 | 20 | 40 | 60 | 35 | 20 | 50 | 65 | 60 |  |  | 60 |
|    | 0.2803 | 30 | 100 | 10 | 70 | 98 | 60 | 95 |  | 99 | 20 | 20 | 30 | 80 | 25 | 10 | 25 | 30 | 30 |  |  | 20 |
|    | 0.0701 | 35 | 75 | 0 | 40 | 75 | 50 | 65 |  | 70 | 10 | 30 | 25 | 65 | 25 | 20 | 40 | 40 | 0 |  |  | 0 |
|    | 0.0175 | 5 | 80 | 0 | 25 | 100 | 20 | 60 |  | 40 | 5 | 5 | 25 | 100 | 10 | 0 | 10 | 40 | 0 |  |  | 0 |
| 65 | 5.6050 | 100 | 100 | 95 | 20 | 100 | 100 | 100 |  | 35 | 30 | 35 | 50 | 100 | 75 | 60 | 80 | 95 | 95 |  |  | 80 |
|    | 1.1210 | 95 | 100 | 65 | 75 | 100 | 100 | 95 |  | 99 | 10 | 30 | 40 | 80 | 35 | 35 | 40 | 50 | 75 |  |  | 25 |
|    | 0.2803 | 60 | 70 | 30 | 40 | 100 | 75 | 75 |  | 75 | 20 | 20 | 35 | 60 | 25 | 15 | 35 | 40 | 40 |  |  | 20 |
|    | 0.0701 | 20 | 70 | 10 | 35 | 75 | 50 | 80 |  | 40 | 5 | 5 | 40 | 70 | 10 | 5 | 10 | 40 | 35 |  |  | 10 |
|    | 0.0175 | 15 | 70 | 5 | 30 | 75 | 40 | 75 |  | 35 | 5 | 5 | 15 | 20 | 10 | 50 | 10 | 20 | 20 |  |  | 0 |
| 66 | 5.6050 | 70 | 100 | 75 | 100 | 100 | 100 | 100 |  | 100 | 25 | 70 | 70 | 100 | 35 | 50 | 70 | 75 | 75 |  |  | 30 |

TABLE D-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Pesw | Cocw |
|---|---|---|---|---|---|---|---|---|---|---|---|---|---|---|---|---|---|---|---|---|---|---|
| 67 | 1.1210 | 70 | 100 | 40 | 70 | 100 | 80 | 95 |  | 70 | 10 | 25 | 40 | 90 | 20 | 35 | 40 | 50 | 70 |  |  | 10 |
|  | 0.2803 | 35 | 100 | 25 | 60 | 99 | 60 | 100 |  | 50 | 10 | 15 | 40 | 60 | 10 | 20 | 30 | 65 | 35 |  |  | 5 |
|  | 0.0701 | 25 | 75 | 10 | 30 | 75 | 40 | 70 |  | 35 | 5 | 5 | 35 | 60 | 5 | 5 | 25 | 40 | 40 |  |  | 0 |
| 68 | 5.6050 | 25 | 100 | 75 | 100 | 50 | 100 | 80 |  | 100 | 5 | 20 | 25 | 90 | 5 | 5 | 20 | 40 | 70 |  |  | 60 |
|  | 1.1210 | 20 | 100 | 75 | 60 | 20 | 75 | 75 |  | 75 | 5 | 5 | 35 | 65 | 0 | 0 | 10 | 30 | 60 |  |  | 25 |
|  | 0.2803 | 10 | 95 | 50 | 40 | 10 | 75 | 50 |  | 70 | 0 | 0 | 20 | 50 | 0 | 0 | 5 | 35 | 25 |  |  | 5 |
|  | 0.0701 | 0 | 50 | 40 | 40 | 10 | 75 | 25 |  | 40 | 5 | 0 | 5 | 40 | 0 | 0 | 5 | 40 | 25 |  |  | 5 |
| 69 | 5.6050 | 70 | 100 | 100 | 100 | 100 | 100 | 100 |  | 100 | 30 | 70 | 100 | 99 | 65 | 100 | 100 | 98 | 100 |  |  | 0 |
|  | 1.1210 | 60 | 100 | 100 | 100 | 98 | 100 | 100 |  | 100 | 10 | 30 | 95 | 80 | 25 | 80 | 100 | 70 | 100 |  |  | 99 |
|  | 0.2803 | 25 | 100 | 70 | 100 | 75 | 100 | 100 |  | 100 | 10 | 10 | 60 | 80 | 20 | 50 | 80 | 35 | 75 |  |  | 98 |
|  | 0.0701 | 10 | 100 | 20 | 50 | 40 | 100 | 70 |  | 100 | 5 | 5 | 25 | 75 | 5 | 5 | 30 | 25 | 40 |  |  | 50 |
|  | 0.0175 | 5 | 75 | 10 | 50 | 10 | 100 | 40 |  | 75 | 5 | 5 | 25 | 40 | 0 | 5 | 20 | 20 | 10 |  |  | 10 |
| 70 | 5.6050 | 50 | 100 | 99 | 100 | 100 | 100 | 100 |  | 100 | 10 | 75 | 95 | 90 | 30 | 95 | 100 | 99 | 100 |  |  | 0 |
|  | 1.1210 | 30 | 100 | 99 | 100 | 95 | 100 | 100 |  | 100 | 10 | 60 | 40 | 70 | 25 | 60 | 70 | 80 | 80 |  |  | 100 |
|  | 0.2803 | 25 | 100 | 30 | 100 | 60 | 99 | 100 |  | 80 | 5 | 20 | 35 | 90 | 10 | 35 | 75 | 50 | 75 |  |  | 70 |
|  | 0.0701 | 20 | 90 | 5 | 99 | 40 | 75 | 75 |  | 50 | 5 | 10 | 35 | 50 | 10 | 30 | 25 | 35 | 20 |  |  | 40 |
|  | 0.0175 | 5 | 80 | 0 | 40 | 40 | 75 | 60 |  | 60 | 5 | 5 | 25 | 50 | 0 | 0 | 20 | 40 | 10 |  |  | 40 |
| 71 | 5.6050 | 90 | 100 | 100 | 100 | 100 | 100 | 100 |  | 100 | 60 | 65 | 100 | 100 | 70 | 98 | 100 | 99 | 100 |  |  | 0 |
|  | 1.1210 | 60 | 100 | 65 | 100 | 100 | 100 | 100 |  | 100 | 25 | 35 | 90 | 90 | 40 | 90 | 95 | 99 | 95 |  |  | 99 |
|  | 0.2803 | 50 | 100 | 35 | 100 | 70 | 100 | 100 |  | 100 | 5 | 70 | 70 | 75 | 40 | 65 | 75 | 80 | 60 |  |  | 90 |
|  | 0.0701 | 40 | 100 | 30 | 70 | 65 | 80 | 100 |  | 70 | 25 | 10 | 25 | 60 | 10 | 20 | 50 | 35 | 35 |  |  | 75 |
|  | 0.0175 | 5 | 98 | 10 | 99 | 75 | 90 | 100 |  | 40 | 5 | 10 | 30 | 50 | 5 | 5 | 20 | 10 | 10 |  |  | 30 |
| 72 | 5.6050 | 65 | 100 | 80 | 100 | 99 | 100 | 100 |  | 100 | 5 | 40 | 80 | 80 | 35 | 90 | 99 | 99 | 99 |  |  | 75 |
|  | 1.1210 | 35 | 75 | 50 | 80 | 100 | 80 | 70 |  | 95 | 5 | 40 | 40 | 65 | 20 | 35 | 80 | 90 | 65 |  |  | 70 |
|  | 0.2803 | 10 | 50 | 35 | 40 | 90 | 75 | 50 |  | 50 | 5 | 5 | 35 | 70 | 0 | 5 | 35 | 50 | 50 |  |  | 25 |
|  | 0.0701 | 0 | 35 | 25 | 95 | 35 | 100 | 70 |  | 35 | 5 | 0 | 10 | 40 | 0 | 0 | 10 | 5 | 30 |  |  | 70 |
|  | 0.0175 | 0 | 35 | 0 | 60 | 0 | 25 | 20 |  | 20 | 0 | 0 | 10 | 40 | 0 | 0 | 0 | 0 | 10 |  |  | 0 |
| 73 | 5.6050 | 90 | 100 | 100 | 100 | 100 | 100 | 100 |  | 100 | 25 | 70 | 90 | 20 | 100 | 98 | 100 | 100 | 100 |  |  | 100 |
|  | 1.1210 | 75 | 100 | 99 | 80 | 100 | 80 | 100 |  | 100 | 20 | 40 | 40 | 10 | 60 | 60 | 99 | 99 | 100 |  |  | 100 |
|  | 0.2803 | 35 | 95 | 99 | 40 | 100 | 75 | 100 |  | 99 | 10 | 5 | 25 | 10 | 20 | 20 | 80 | 40 | 95 |  |  | 80 |
|  | 0.0701 | 10 | 60 | 40 | 25 | 95 | 50 | 100 |  | 50 | 5 | 0 | 20 | 5 | 10 | 5 | 5 | 30 | 30 |  |  | 70 |
|  | 0.0175 | 5 | 40 | 25 | 40 | 75 | 25 | 75 |  | 25 | 5 | 0 | 10 | 5 | 5 | 5 | 0 | 25 | 10 |  |  | 35 |
|  | 0.0044 | 5 | 20 | 0 | 5 | 20 | 5 | 65 |  | 0 | 0 | 0 | 5 | 5 | 5 | 5 | 5 | 10 | 10 |  |  | 5 |
| 74 | 5.6050 | 90 | 100 | 100 | 100 | 99 | 100 | 100 |  | 100 | 20 | 40 | 25 | 20 | 30 | 30 | 50 | 80 | 99 |  |  | 90 |
|  | 1.1210 | 70 | 80 | 99 | 80 | 100 | 80 | 100 |  | 60 | 10 | 5 | 25 | 10 | 10 | 10 | 25 | 30 | 75 |  |  | 75 |
|  | 0.2803 | 35 | 100 | 40 | 40 | 90 | 75 | 100 |  | 40 | 5 | 0 | 25 | 5 | 10 | 5 | 50 | 20 | 50 |  |  | 60 |
|  | 0.0701 | 20 | 75 | 25 | 25 | 75 | 50 | 100 |  | 20 | 5 | 0 | 20 | 5 | 10 | 10 | 30 | 50 | 30 |  |  | 30 |
|  | 0.0175 | 10 | 70 | 10 | 40 | 50 | 25 | 75 |  | 10 | 5 | 0 | 10 | 5 | 5 | 5 | 10 | 40 | 20 |  |  | 5 |
| 75 | 5.6050 | 50 | 40 | 0 | 5 | 20 | 5 | 20 |  | 5 | 0 | 10 | 5 | 5 | 0 | 10 | 10 | 50 | 5 |  |  | 0 |
|  | 1.1210 | 50 | 100 | 50 | 70 | 100 | 100 | 99 |  | 100 | 25 | 35 | 98 | 100 | 98 | 100 | 100 | 100 | 100 |  |  | 98 |
|  | 0.2803 | 35 | 98 | 20 | 40 | 10 | 70 | 98 |  | 60 | 10 | 25 | 50 | 80 | 30 | 50 | 75 | 98 | 90 |  |  | 98 |
|  | 0.0701 | 10 | 75 | 5 | 25 | 75 | 25 | 90 |  | 35 | 5 | 20 | 30 | 70 | 5 | 20 | 70 | 75 | 80 |  |  | 75 |
|  | 0.0175 | 5 | 25 | 0 | 20 | 50 | 25 | 98 |  | 25 | 0 | 5 | 25 | 65 | 0 | 5 | 65 | 70 | 40 |  |  | 5 |
|  | 0.0044 | 0 | 70 | 0 | 10 | 50 | 5 | 80 |  | 100 | 0 | 0 | 25 | 25 | 0 | 0 | 40 | 60 | 30 |  |  | 0 |
| 76 | 5.6050 | 50 | 100 | 95 | 98 | 100 | 99 | 100 |  | 40 | 35 | 30 | 90 | 100 | 75 | 75 | 100 | 100 | 100 |  |  | 80 |
|  | 1.1210 | 70 | 99 | 75 | 98 | 100 | 100 | 70 |  | 40 | 20 | 25 | 90 | 99 | 30 | 30 | 75 | 80 | 75 |  |  | 65 |

TABLE D-continued

| Ex. No. | Rate kg/ha | Sobe | Cotz | Rape | Cobu | Wibw | Mogl | Hese | Jiwe | Vele | Whez | Rice | Grso | Corn | Dobr | Prmi | Bygr | Lacg | Grft | Sube | Pesw | Cocw |
|---|---|---|---|---|---|---|---|---|---|---|---|---|---|---|---|---|---|---|---|---|---|---|
| 79 | 0.2803 | 40 | 90 | 5 | 30 | 98 | 65 | 75 | | 60 | 10 | 25 | 40 | 70 | 20 | 20 | 75 | 75 | 75 | | | 35 |
| | 0.0701 | 10 | 75 | 5 | 30 | 75 | 50 | 60 | | 40 | 5 | 10 | 60 | 70 | 5 | 5 | 30 | 75 | 30 | | | 5 |
| | 5.6050 | | 10 | 100 | 100 | 70 | 30 | 100 | 60 | 95 | 75 | | | | | | | | | | | |
| | 5.6050 | 55 | | 98 | | 5 | | 70 | | | 30 | | | | | | | | | | | |
| | 1.1210 | 25 | | 80 | | 5 | | 50 | | | 30 | | | | | | | | | | | |
| | 1.1210 | | 10 | 75 | 100 | 70 | 30 | 100 | 20 | 90 | 75 | | | | | | | | | | | |
| | 0.2803 | | 10 | 25 | 100 | 70 | 30 | 100 | 20 | 75 | 75 | | | | | | | | | | | |
| | 0.2803 | 20 | | 60 | | 5 | | 20 | | | 30 | | | | | | | | | | | |
| | 0.0701 | 15 | | 40 | | 5 | | 10 | | | 30 | | | | | | | | | | | |
| | 0.0701 | | 10 | 5 | 35 | 70 | 30 | 10 | 5 | 30 | 75 | | | | | | | | | | | |
| | 0.0175 | | 10 | 5 | 25 | 70 | 30 | 10 | 0 | 25 | 75 | | | | | | | | | | | |
| | 0.0175 | 0 | | 20 | | 5 | | 0 | | | 30 | | | | | | | | | | | |
| 80 | 11.2100 | 35 | | 100 | | 5 | | 30 | | | 30 | | | | | | | | | | | |
| | 11.2100 | | 10 | 80 | 100 | 70 | 30 | 99 | 60 | 100 | 75 | | | | | | | | | | | |
| | 5.6050 | | 10 | 60 | 100 | 70 | 30 | 98 | 40 | 99 | 75 | | | | | | | | | | | |
| | 1.1210 | 25 | | 95 | | 5 | | 20 | | | 30 | | | | | | | | | | | |
| | 1.1210 | 20 | | 85 | | 5 | | 15 | | | 30 | | | | | | | | | | | |
| | 0.2803 | | 10 | 25 | 60 | 70 | 30 | 60 | 20 | 75 | 75 | | | | | | | | | | | |
| | 0.2803 | | 10 | 10 | 50 | 70 | 30 | 60 | 5 | 70 | 75 | | | | | | | | | | | |
| 81 | 11.2100 | 15 | 100 | 55 | 75 | 100 | 100 | 100 | | 95 | 10 | 15 | 40 | 65 | 25 | 50 | 75 | 75 | 100 | | | 40 |
| | 5.6050 | 50 | 100 | 80 | 70 | 98 | 99 | 100 | | 98 | 10 | 15 | 50 | 75 | 25 | 50 | 60 | 65 | 90 | | | 25 |
| | 1.1210 | 25 | 70 | 75 | 50 | 70 | 99 | 90 | | 70 | 5 | 0 | 25 | 75 | 5 | 30 | 20 | 40 | 60 | | | 10 |
| | 0.2803 | 20 | 90 | 20 | 20 | 60 | 75 | 75 | | 75 | 10 | 0 | 20 | 35 | 0 | 20 | 10 | 50 | 25 | | | 0 |
| 84 | 11.2100 | 10 | 90 | 0 | 20 | 70 | 100 | 99 | | 75 | 5 | 20 | 30 | 60 | 25 | 20 | 40 | 90 | 80 | | | 10 |
| | 5.6050 | 25 | 65 | 50 | 60 | 70 | 99 | 75 | | 60 | 10 | 5 | 25 | 60 | 20 | 25 | 35 | 90 | 70 | | | 0 |
| | 1.1210 | 25 | 60 | 35 | 40 | 75 | 75 | 99 | | 40 | 5 | 10 | 10 | 65 | 5 | 10 | 10 | 70 | 30 | | | 0 |
| | 0.2803 | 20 | 40 | 20 | 25 | 25 | 65 | 35 | | 20 | 0 | 0 | 5 | 65 | 0 | 5 | 5 | 35 | 25 | | | 0 |
| 85 | 11.2100 | 0 | 5 | 0 | 5 | 0 | 80 | 98 | | 70 | 35 | 40 | 35 | 99 | 20 | 35 | 70 | 60 | 50 | | | 0 |
| | 5.6050 | 40 | 99 | 100 | 60 | 100 | 65 | 70 | | 40 | 30 | 10 | 35 | 100 | 10 | 20 | 35 | 60 | 30 | | | 50 |
| | 1.1210 | 40 | 80 | 100 | 35 | 99 | 80 | 50 | | 70 | 10 | 40 | 30 | 65 | 20 | 25 | 40 | 50 | 25 | | | 50 |
| | 0.2803 | 40 | 60 | 99 | 30 | 95 | 60 | 70 | | 40 | 10 | 25 | 25 | 60 | 5 | 20 | 20 | 70 | 30 | | | |
| 86 | 11.2100 | 10 | 40 | 75 | 10 | 75 | 40 | 50 | | 25 | 10 | 30 | 60 | 70 | 20 | 10 | 20 | 60 | 10 | | | |
| | 5.6050 | 30 | 99 | 100 | 40 | 99 | 70 | 80 | | 30 | 10 | 25 | 30 | 100 | 5 | 35 | 35 | 40 | 35 | | | |
| | 1.1210 | 20 | 65 | 100 | 30 | 80 | 70 | 80 | | 30 | 5 | 30 | 20 | 65 | 5 | 5 | 60 | 40 | 30 | | | |
| | 0.2803 | 10 | 60 | 100 | 10 | 75 | 40 | 60 | | 50 | 10 | 25 | 20 | 50 | 5 | 35 | 20 | 40 | 20 | | | |
| | | 5 | 20 | 50 | 5 | 30 | 5 | 50 | | 10 | 0 | 25 | 25 | 50 | 0 | 30 | 20 | 75 | 20 | | | |

As can be seen from the data above, the compounds have good herbicidal activity and are safe on certain crops and can thus be used for selective control of weeds in these crops. Certain compounds of the present invention (Ex 1, 2 and 26) have high herbicidal activity at low application rates for resulting cost savings and lower pesticide load on the environment.

The herbicidal compositions of this invention, including concentrates suitable for transportation which require dilution prior to application, and dilute composition suitable for application generally in accordance with concentrations set forth below. Compositions may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, polymethylene bisnaphthalene sulfonate and polyethyleneoxide-polypropyleneoxide copolymers.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates which are suitable for transportation are usually solutions of active ingredient in water-immiscible or partially water-immiscible solvents together with a surface active agent. Suitable solvents for the active ingredient of this invention include dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compounds of the present invention appear to show the greatest activity when applied as a postemergence herbicide. Further, when applied as a preplant incorporated, the activity appears to decrease with increasing organic matter in the soil.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, dinitroanilines uracils, acetic acid or phenol derivatives, thiolcarbamates, triazoles, benzoic acids, nitriles, biphenyl ethers and the like such as:

Heterocyclic Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-α:2',1'-c)-pyrazidiinium salt 5-Bromo-3-isopropyl-6-methyluracil 1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

Ureas

N-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-1,3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)]benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate classic

Carbamates/Thiolcarbamates

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-ethyl-N,N-dipropylthiolcarbamate
S-propyl N,N-dipropylthiolcarbamate
S-2,3,3-trichloroallyl N,N-diisopropylthiolcarbamate
S-ethyl-N,N-diisobutylthiolcarbamate

Acetamides/Acetanilides/Anilines/Amides

2-Chloro-N,N-diallylacetamide
N,N-dimethyl-2,2-diphenylacetamide
N-(2,4-dimethyl-5-[[(trifluoromethyl)sulfonyl]amino]-phenyl]acetamide N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
α,α,α-Trifluoro-2,6-dinitro-N,N-dipropyl-p-toluidine
N-(1,1-dimethylpropynyl)-3,5-dichlorobenzamide

Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
Butyl 2-[4-[(5-(trifluoromethyl)-2-pyridinyl)oxy]-phenoxy]-propanoate
glyphosate

Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy) ethyl 5-[2-chloro-4-(trifluoromethyl)-phenoxy]-2-nitrobenzoate
Acifluorfen
Bifenox
Chloroxuron
Diclofop-methyl
Fluazifop-butyl

Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo- Sethoxydin
imazethapyr
imazaquin
imazapyr Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

I. Emulsifiable Concentrates

|   |   | Weight Percent |
|---|---|---|
| A. | Compound of Example No. 1 | 11.0 |
|   | Free acid of complex organic phosphate or aromatic or aliphatic hydrophobe base (e.g., GAFAC RE-610, registered trademark of GAF Corp.) | 5.59 |
|   | Polyoxyethylene/polyoxypropylene block copolymer with butanol (e.g., Tergitol XH, registered trademark of Union Carbide Corp.) | 1.11 |
|   | Phenol | 5.34 |
|   | Monochlorobenzene | 76.96 |
|   |   | 100.00 |
| B. | Compound of Example No. 1 | 25.00 |
|   | Free acid of complex organic phosphate of aromatic or aliphatic hydrophobe base (e.g., GAFAC RE-610) | 5.00 |
|   | Polyoxyethylene/polyoxypropylene block copolymer with butanol (e.g., Tergitol XH) | 1.60 |
|   | Phenol | 4.75 |
|   | Monochlorobenzene | 63.65 |
|   |   | 100.00 |

II. Flowables

|   |   | Weight Percent |
|---|---|---|
| A. | Compound of Example No. 1 | 25.00 |
|   | Methyl cellulose | 0.3 |
|   | Silica Aerogel | 1.5 |
|   | Sodium lignosulfonate | 3.5 |
|   | Sodium N-methyl-N-oleyl taurate | 2.0 |

-continued

| | | Weight Percent |
|---|---|---|
| | Water | 67.7 |
| | | 100.00 |
| B. | Compound of Example No. 1 | 45.0 |
| | Methyl cellulose | .3 |
| | Silica aerogel | 1.5 |
| | Sodium lignosulfonate | 3.5 |
| | Sodium N-methyl-N-oleyl taurate | 2.0 |
| | Water | 47.7 |
| | | 100.00 |

III. Wettable Powders

| | | Weight Percent |
|---|---|---|
| A. | Compound of Example No. 1 | 25.0 |
| | Sodium lignosulfonate | 3.0 |
| | Sodium N-methyl-N-oleyl-taurate | 1.0 |
| | Amorphous silica (synthetic) | 71.0 |
| | | 100.00 |
| B. | Compound of Example 1 | 80.00 |
| | Sodium dioctyl sulfosuccinate | 1.25 |
| | Calcium lignosulfonate | 2.75 |
| | Amorphous silica (synthetic) | 16.00 |
| | | 100.00 |
| C. | Compound of Example No. 1 | 10.0 |
| | Sodium lignosulfonate | 3.0 |
| | Sodium N-methyl-N-oleyl-taurate | 1.0 |
| | Kaolinite clay | 86.0 |
| | | 100.00 |

IV. Dusts

| | | Weight Percent |
|---|---|---|
| A. | Compound of Example No. 1 | 2.0 |
| | Attapulgite | 98.0 |
| | | 100.00 |
| B. | Compound of Example No. 1 | 30.0 |
| | Ethylene glycol | 1.0 |
| | Bentonite | 69.0 |
| | | 100.00 |

V. Granules

| | | Weight Percent |
|---|---|---|
| A. | Compound of Example No. 1 | 15.0 |
| | Granular attapulgite (20/40 mesh) | 85.0 |
| | | 100.00 |
| B. | Compound of Example No. 1 | 30.0 |
| | Diatomaceous earth (20/40) | 70.0 |
| | | 100.00 |
| C. | Compound of Example No. 1 | 1.0 |
| | Ethylene glycol | 5.0 |
| | Methylene blue | 0.1 |
| | Pyrophyllite | 93.9 |
| | | 100.00 |

When operating in accordance with the present invention, effective amounts of the compounds of this invention are applied to the soil containing the seeds, or vegetative propagules or may be incorporated into the soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective pre-emergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

the term "soil" is employed in its broadest sense to be inclusive of all conventional "soils" as defined in *Webster's New International Dictionary*, Second Edition, Unabridged (1961). Thus, the term refers to any substance or medium in which vegetation may take root and grow, and includes not only earth but also compost, manure, muck, humus, loam, silt, mire, clay, sand, and the like, adapted to support plant growth.

Although the invention is described with respect to specific modifications, the details thereof are not to be construed as limitations, for it will be apparent that various embodiments, changes and modifications may be resorted to without departing from the spirit and scope thereof and it is understood that such equivalent embodiments are intended to be included within the scope of this invention.

We claim:

1. A 3-phenoxypyrazole or agronomically acceptable salt thereof wherein: the phenyl ring has a para halo or cyano substituent and has a meta substituent having a molecular weight of less than 300 and selected from alkoxy, haloalkoxy, di(alkoxy), alkoxycarbonyl, alkoxycarbonylalkoxy, aminocarbonylalkoxy, alkylsulfonylaminocarbonylalkoxy, alkylamino, hydroxyalkylamino, alkoxyamino, alkoxyalkylamino, hydroxycarbonylalkylamino, and alkoxycarbonylalkoxyimino; and the pyrazole ring has a methyl, ethyl, halomethyl or haloethyl substituent in the 1-position; a halo or methyl substituent in the 4-position; and a chloro, cyano, halomethyl, haloethyl, methylthio, ethylthio, methylsulfinyl, ethylsulfinyl, methylsulfonyl, ethylsulfonyl or methoxymethyl substituent in the 5-position.

2. A herbicidal composition comprising an adjuvant and an effective amount of a 3-phenoxypyrazole or agronomically acceptable salt thereof wherein: the phenyl ring has a para halo or cyano substituent and has a meta substituent having a molecular weight of less than 300 and selected from alkoxy, haloalkoxy, di(alkoxy), alkoxycarbonyl, alkoxycarbonylalkoxy, aminocarbonylalkoxy, alkylsulfonylaminocarbonylalkoxy, alkylamino, hydroxyalkylamino, alkoxyamino, alkoxyalkylamino, hydroxycarbonylalkylamino, and alkoxycarbonylalkoxyimino; and the pyrazole ring has a methyl, ethyl, halomethyl or haloethyl substituent in the 1-position; a halo or methyl substituent in the 4-position; and a chloro, cyano, halomethyl, haloethyl, methylthio, ethylthio, methylsulfinyl, ethylsulfinyl, methylsulfonyl, ethylsulfonyl or methoxymethyl substituent in the 5-position.

3. A method of controlling the growth of undesirable vegetation comprising applying to the plant locus an effective amount of a 3-phenoxypyrazole or agronomically acceptable salt thereof wherein: the phenyl ring has a para halo or cyano substituent and has a meta substituent having a molecular weight of less than 300 and selected from alkoxy, haloalkoxy, di(alkoxy), alkoxycarbonyl, alkoxycarbonylalkoxy, aminocarbonylalkoxy, alkylsulfonylaminocarbonylalkoxy, alkylamino, hydroxyalkylamino, alkoxyamino, alkoxyalkylamino, hydroxycarbonylalkylamino, and alkoxycarbonylalkoxyimino; and the pyrazole ring has a methyl, ethyl, halomethyl or haloethyl substituent in the 1-position; a halo or methyl substituent in the 4-position; and a chloro, cyano, halomethyl, haloethyl, methylthio, ethylthio, methylsulfinyl, ethylsulfinyl, methylsulfonyl, ethylsulfonyl or methoxymethyl substituent in the 5-position.

* * * * *